(12) United States Patent
Oehrlein

(10) Patent No.: US 6,187,754 B1
(45) Date of Patent: Feb. 13, 2001

(54) SIALYL-LEWIS$^A$ AND SIALYL-LEWIS$^x$ EPITODE ANALOGUES

(75) Inventor: Reinhold Oehrlein, Rheinfelden (DE)

(73) Assignee: GlycoTech Corp., Rockville, MD (US)

( * ) Notice: Under 35 U.S.C. 154(b), the term of this patent shall be extended for 0 days.

(21) Appl. No.: 09/117,521

(22) PCT Filed: Jan. 17, 1997

(86) PCT No.: PCT/EP97/00223

§ 371 Date: Jan. 8, 1999

§ 102(e) Date: Jan. 8, 1999

(87) PCT Pub. No.: WO97/28174

PCT Pub. Date: Aug. 7, 1997

(30) Foreign Application Priority Data

Jan. 30, 1996 (CH) ........................................ 229/96

(51) Int. Cl.$^7$ .......................... A61K 31/70; C07H 15/00; C07H 17/00
(52) U.S. Cl. .................. 514/25; 514/54; 514/61; 514/62; 536/17.2; 536/18.7; 536/53; 536/55.2
(58) Field of Search ................... 514/25, 54, 61, 514/62; 536/17.2, 18.7, 53, 55.2

(56) References Cited

U.S. PATENT DOCUMENTS 4,925,796 * 5/1990 Bergh et al. ........................ 435/97

FOREIGN PATENT DOCUMENTS 94 26760 * 11/1994 (WO).
94 29477 * 12/1994 (WO).

OTHER PUBLICATIONS

Siuzdak et al. Chem. Sbstr. vol. 122, No. 17, Apr. 24, 1995, abstract No. 208092.*
Bioorg. Med. Chem. Lett. 1994, 4(24), 2863–2866.*
Hasegawa et al. Carbohydrate Research 1994, 257, 67–80.*
Hasegawa et al. Carbohydrate Research 1995, 274, 165–181.*

* cited by examiner

*Primary Examiner*—Kathleen K. Fonda
(74) *Attorney, Agent, or Firm*—Seed Intellectual Property Law Group PLLC

(57) ABSTRACT

Sialyl-Lewis$^a$ and sialyl-Lewis$^x$ epitope analogues, in which the natural N-acetyl group of the N-acetylglucosamine monomer is replaced by various hydroxylated aromatic substituents.

46 Claims, No Drawings

SIALYL-LEWIS$^A$ AND SIALYL-LEWIS$^X$ EPITODE ANALOGUES

This application is the U.S. national stage entry under 35 U.S.C. § 371 of PCT/EP97/00223, filed Jan. 17, 1997.

The invention relates to sialyl-Lewis$^a$ and sialyl-Lewis$^x$ epitope analogues, in which the natural N-acetyl group of the N-acetylglucosamine monomer is replaced by various hydroxylated aromatic substituents, to their preparation and use and to compositions which comprise these compounds.

Carbohydrate domains on cell surfaces are of importance in the therapy of many diseases, for example of viral and bacterial infections, inflammatory diseases, rheumatic arthritis, allergies, post-infarction syndromes, septic shock, stroke, acute and chronic organ rejections, sepsis and cancer (formation of metastases) [Witczak, Z. J., Current Med. Commun. 1:392–405 (1995)]. Carbohydrate epitopes on eukaryotic cells are used by viruses, bacteria and toxins as specific attachment sites [Edwards, M., Curr. Op. in Therapeutic Patents 1617–1630 (1991)]. Carbohydrate domains also function as receptors for peripatetic malignant cells [Muramatsu, T., Glycobiology 3:294–296 (1993)]. However, they also constitute specific binding epitopes for certain transmembrane proteins, for example E, P and L selectins. Selectins are present in the surface of endothelial cells and of circulating cells of the hematolymphoid system. They enter into specific interactions with carbohydrates [Lasky, L. A., Ann. Rev. Biochem. 64:113–139 (1995); Nelson, R. M., Dolich, S., Aruffo, A., Cecconi, O., Bevilacqua, M. P., J. Clin. Invest. 91:1157- (1993)].

Sialylated and/or fucosylated carbohydrate epitopes are in the main thought to be responsible for these adhesion phenomena [Varki, A., Glycobiology 3:97–130 (1993)]. A particular importance in pathogenic inflammatory processes is attributed to the two tetrasaccharide sialyl-Lewis$^a$ [αsia(2→3)βgal(1→3)[αfuc(1→4)]-βglcNAc-OR*] and sialyl-Lewis$^x$ [asia(2→3)βgal(1→4)[αfuc(1→3)]-βglcNAc-OR*] epitopes (with R* having to be an aglycone having at least one carbon atom) [Fukuda, M., Bioorg. Med. Chem. 3:207–215 (1995)].

Several routes have already been pursued for obtaining derivatives of these carbohydrate epitopes which have both better binding affinities than that of the natural ligand and an increased physiological stability. On the one hand, the native epitope has been modified to only a trivial extent. Thus, N-acetylglucosamine has been replaced by sugars such as glucosamine or glucose (WO 93/10 796) or by straight-chain or cyclic aliphatic residues (EP 671 408). On the other hand, as many of the sugar monomers of the epitope as possible have been replaced by other functional units [Allanson, N. M., Davidson, A. H., Floyd, C. D., Martin, F. M., Tetrahedron Assym. 5:2061–2076 (1994)]. However, none of these different approaches has so far resulted in epitope analogues having significantly higher binding affinities. WO 94/26 760 discloses that compounds having higher binding affinities for selectins can be obtained if the N-acetyl group of the N-acetylglucosamine, which group is not regarded as being relevant for binding (EP 671 408), is replaced by aromatic amides.

Surprisingly, the present invention makes available sialyl-Lewis$^x$ and sialyl-Lewis$^a$ epitope analogues having an improved binding affinity for the corresponding selectins, in which analogues the natural N-acetyl group of the N-acetylglucosamine monomer is replaced by various hydroxylated aromatic substituents.

Inter alia, the present invention provides compounds of the formula I or II

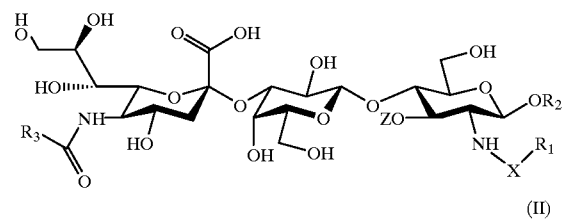

(I)

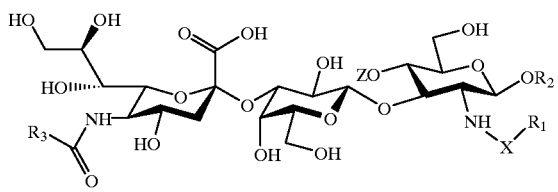

(II)

in which
Z is an α-bonded L-fucose of the formula III

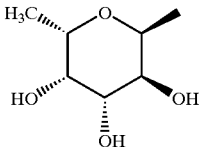

(III)

$R_1$ is a monocyclic or bicyclic $C_6$–$C_{10}$aryl or $C_2$–$C_9$heteroaryl which is substituted by at least one OH and can be substituted, once or more than once, by a substituent selected from the group comprising halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide;

$R_2$ is $C_1$–$C_{18}$alkyl, monosubstituted or polysubstituted $C_1$–$C_{18}$alkyl, $C_3$–$C_8$cycloalkyl or monosubstituted or polysubstituted $C_3$–$C_8$cycloalkyl, where one or more $CH_2$ groups in the alkyl and in the cycloalkyl can be replaced, independently of each other, by oxygen, sulfur or an imino group and the substituents are selected from the group comprising OH, SH, $NH_2$, carboxamide and C(O)OR, in which R is H or $C_1$–$C_{18}$alkyl;

$R_3$ is a methyl group or hydroxymethyl group; and

X is —C(O)—, —C(S)—, —S(O)$_2$—, —C(O)Y— or —C(S)Y—, where Y is NH, O, S, S-$C_1$–$C_6$alkylene, NH—$C_1$–$C_6$alkylene or O—$C_1$–$C_6$alkylene.

Within the scope of the present invention, the aryl or heteroaryl is a five-membered or six-membered ring or a bicycle formed from two fused six-membered or five-membered rings or one six-membered ring and one five-membered ring, with one or more heteroatoms, selected from the group comprising oxygen, nitrogen and sulfur atoms, being present in the heteroaryl. Examples are derived from benzene, pentalene, naphthalene, indene, furan, pyrrole, pyrazole, imidazole, isoxazole, oxazole, furazan, thiadiazole, thiophene, thiazole, oxadiazole, triazole, indole, indazole, purine, benzimidazole, benzoxazole, benzothiazole, pyran, pyridine, pyridazine, triazine, pyrimidine, pyrazine, isoquinoline, cinnoline, phthalazine, quinoline, quinazoline, pteridine, benzotriazine or quinoxaline.

OH as a substituent of aryl and heteroaryl in the definition of $R_1$ is preferably present once or twice. Both the C atoms and the heteroatoms can be substituted in the heteroaryl. The position(s) of the OH substituent(s) can be variable. If two OH substituents are present, it has then been found to be advantageous if they are in the ortho or meta positions relative to each other.

Halogen is preferably F, Cl or Br.

The previously mentioned alkyl and alkylene can be linear or branched. Some examples of alkyl, alkoxy, thioalkyl and alkylamino, which preferably contain from 1 to 12 C atoms, are methyl, ethyl and the isomers of propyl, butyl, pentyl, hexyl, heptyl, octyl, nonyl, decyl, undecyl and dodecyl, and also corresponding alkoxy, thioalkyl and alkylamino radicals. Preferred alkyl, alkoxy, thioalkyl and alkylamino radicals are methyl, ethyl, n- and i-propyl, n-, i- and t-butyl, methoxy, ethoxy, methylthio and ethylthio, aminomethyl and aminoethyl.

Within the scope of the present invention, those compounds of the formula I or II are preferred in which $R_1$ is (a) a monohydroxylated, dihydroxylated or trihydroxylated phenyl; (b) a monohydroxylated, dihydroxylated or trihydroxylated monocyclic heteroaryl, in which one or more CH units are replaced, independently of each other, by one or more nitrogen atoms, or (c) a hydroxylated heteroaryl consisting of two six-membered rings, in which one or more CH units is/are replaced, independently of each other, by one or more nitrogen atoms. Of these compounds, those are in particular preferred in which additionally a hydrogen atom on the aryl or heteroaryl nucleus is replaced by halogen, a nitro group, a trifluoromethyl group, an O—$C_1$–$C_8$alkyl group, a linear or branched $C_1$–$C_{18}$alkyl, an amino group, a sulfhydro group; NH—$C_1$–$C_{18}$alkyl, a dialkylamino group, an NH-phenyl or NH-benzyl residue, a thio-$C_1$–$C_{18}$alkyl or a carbamate group such as OC(O)NHalkyl or NHC(O) Oalkyl, with it being .possible for the alkyl, independently of each other, to be a linear or branched $C_1$–$C_{18}$alkyl.

Another group of preferred compounds comprises compounds of the formula I or II in which $R_1$ is a monocyclic aryl or heteroaryl which is substituted by at least one OH and can be substituted, once or more than once, by a substituent selected from the group comprising halogen, trifluoromethyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide. Those compounds are particularly preferred in which $R_1$ is a monocyclic aryl or heteroaryl which is substituted by at least one OH. Those compounds are in particular preferred in which $R_1$ is phenyl or pyrimidyl which is substituted once or twice by OH, very particularly preferably phenyl which is substituted once or twice by OH or pyrimidyl which is substituted twice by OH.

Those compounds of the formula I or II also form a preferred embodiment in which $R_1$ is a monocyclic or bicyclic $C_6$–$C_{10}$aryl or $C_2$–$C_9$heteroaryl, preferably $C_2$–$C_9$-N heteroaryl, which is substituted, once or twice, by a hydroxyl group and can be substituted, once or more than once, by a substituent which is selected from the group comprising $C_1$–$C_{18}$alkyl, $C_1$–$C_{18}$alkoxy, halogen, nitro and amino.

In this context, those compounds form a preferred subgroup in which $R_1$ is phenyl, pyrimidinyl, pyridinyl, quinolinyl or pteridinyl which is substituted once or twice by a hydroxyl group and can be substituted, once or more than once, by a substituent selected from the group comprising $C_1$–$C_{18}$alkyl, $C_1$–$C_{18}$alkoxy, halogen, nitro and amino. $R_1$ is particularly preferably phenyl which is substituted once or twice by a hydroxyl group and can be substituted, once or twice, by a substituent selected from the group comprising $C_1$–$C_{18}$alkyl, $C_1$–$C_{18}$alkoxy, halogen, nitro and amino; pyrimidinyl which is substituted twice by a hydroxyl group; quinolinyl which is substituted by one or two hydroxyl group(s), pyridinyl which is substituted once by a hydroxyl group; or pteridinyl which is substituted once by a hydroxyl group and can be substituted by an amino group.

Those compounds of the formula I or II form another preferred embodiment in which $R_1$ is 2-hydroxyphenyl; 2,4-dihydroxyphenyl; 3,4-dihydroxyphenyl; 3,5-dihydroxyphenyl; 4-hydroxy-3-methoxyphenyl; 4-hydroxy-3,5-dimethoxyphenyl; 3-fluoro-6-hydroxyphenyl; 2-hydroxy-5-methylphenyl; 3-hydroxy-4-nitrophenyl; 3-hydroxy-4-aminophenyl; 3,5-dihydroxypyrimidinyl; 3-(6-hydroxy)pyridinyl; 2-(8-hydroxy)quinolinyl; 6-(2-amino-8-hydroxy)pteridinyl; or 2-(4,8-dihydroxy)quinolinyl.

Those compounds are particularly preferred in which $R_1$ is 2,4-dihydroxyphenyl; 3,4-dihydroxyphenyl; 3,5-dihydroxyphenyl; 3-fluoro-6-hydroxyphenyl; 3,5-dihydroxypyrimidinyl; 2-(8-hydroxy)quinolinyl, 2-(4,8-dihydroxy)quinolinyl or 6-(2-amino-8-hydroxy)pteridinyl; in particular 2,4-dihydroxyphenyl; 3,5-dihydroxypyrimidinyl, 2-(8-hydroxy)quinolinyl or 2-(4, 8dihydroxy)quinolinyl.

Within the scope of the present invention, those compounds of the formula I or II are furthermore preferred in which $R_2$ is $C_1$–$C_{18}$alkyl, monosubstituted or polysubstituted $C_1$–$C_{18}$alkyl, $C_3$–$C_8$cycloalkyl or monosubstituted or polysubstituted $C_3$–$C_8$cycloalkyl, with the substituents being selected from the group comprising OH, SH, $NH_2$, carboxamide and C(O)OR, in which R is H or $C_1$–$C_{18}$alkyl. Particularly preferably, $R_2$ is $C_1$–$C_{18}$alkyl or $C_1$–$C_{18}$alkyl which is substituted, independently of each other, once or more than once, by OH, SH, $NH_2$, carboxamide or C(O) O—$C_1$–$C_{18}$alkyl, and, very preferably, $R_2$ is $C_1$–$C_{18}$alkyl which is unsubstituted or substituted by $C(O)OCH_3$, with $R_2$ most preferably being —$(CH_2)_8COOCH_3$.

Within the scope of the present invention, those compounds of the formula I or II are furthermore preferred in which $R_3$ is methyl.

In preferred compounds of the formula I or II, X is —C(O)—, —C(S)—, —C(O)Y— or —C(S)Y—, where Y is —NH—, —O—, —NH—$C_1$–$C_6$alkylene or —O—$C_1$–$C_6$alkylene; particularly preferably, X is —C(O)—, —C(S)—, —C(O)Y— or —C(S)Y—, where Y is —NH— or —O—$C_1$–$C_6$alkylene; in particular, X is —C(O)— or —C(O)Y—, where Y is —O—$C_1$–$C_6$alkylene, in particular —O—$CH_2$—.

Preferred compounds of the formula I or II are in particular those in which $R_1$ is a monocyclic aryl or heteroaryl which is substituted by at least one OH and can be substituted, once or more than once, by a substituent selected from the group comprising halogen, trifluoromethyl, nitro, $C_1$–$C_{18}$alkyl, $C_1$–$C_{18}$alkoxy, amino, mono-$C_1$–$C_{18}$alkylamino, di-$C_1$–$C_{18}$-alkylamino, benzylamino, sulfhydryl, thio-$C_1$–$C_{18}$alkyl and $C_1$–$C_{18}$alkylcarboxamide; $R_2$ is $C_1$–$C_{18}$alkyl, monosubstituted or polysubstituted $C_1$–$C_{18}$alkyl, $C_3$–$C_8$cycloalkyl or monosubstituted or polysubstituted $C_3$–$C_8$cycloalkyl, where the substituents are selected from the group comprising OH, SH, $NH_2$, carboxamide and C(O)OR, in which R is H or $C_1$–$C_{18}$alkyl; $R_3$ is methyl; and X is —C(O)—, —C(S)—, —S(O)$_2$—, —C(O)Y— or —C(S)Y—, with Y being NH or O—$CH_2$—.

Very particularly preferred compounds of the formula I or II are those in which $R_1$ is a monocyclic aryl or heteroaryl which is substituted by at least one OH; $R_2$ is $C_1$–$C_{18}$alkyl or $C_1$–$C_{18}$alkyl which is substituted, once or more than once, independently of each other, by OH, SH, $NH_2$, carboxamide or C(O)OR, in which R is H or $C_1$–$C_{18}$alkyl; $R_3$ is methyl; and X is —C(O)— or —C(O)Y—, with Y being O—$CH_2$—.

Of these compounds, those compounds are in particular preferred in which $R_1$ is phenyl or pyrimidyl which is substituted once or twice by OH, very particularly preferably phenyl which is substituted once or twice by OH or pyrimidyl which is substituted twice by OH; and $R_2$ is $C_1$–$C_{18}$alkyl or $C_1$–$C_{18}$alkyl which is substituted once by C(O)OR, most preferably is —$(CH_2)_8COOCH_3$ or —$(CH_2)_8COOH$.

Those compounds of the formula I or II also form a preferred embodiment in which $R_1$ is a monocyclic or bicyclic $C_6$–$C_{10}$aryl or $C_2$–$C_9$heteroaryl, preferably $C_2$–$C_9$-N heteroaryl, which is substituted, once or twice, by a hydroxyl group and can be substituted, once or more than once, by a substituent selected from the group comprising $C_1$–$C_{18}$alkyl, $C_1$–$C_{18}$alkoxy, halogen, nitro and amino; $R_2$ is $C_1$–$C_{18}$alkyl, monosubstituted or polysubstituted $C_1$–$C_{18}$alkyl, $C_3$–$C_8$cycloalkyl or monosubstituted or polysubstituted $C_3$–$C_8$cycloalkyl, where the substituents are selected from the group comprising OH, SH, $NH_2$, carboxamide and C(O)OR, in which R is H or $C_1$–$C_{18}$alkyl; $R_3$ is methyl; and X is —C(O)—, —C(S)—, —C(O)Y— or —C(S)Y—, where Y is —NH—, —O—, —NH—$C_1$–$C_6$alkylene or —O—$C_1$–$C_6$alkylene.

In this context, those compounds form a preferred subgroup in which $R_1$ is phenyl, pyrimidinyl, pyridinyl, quinolynyl or pteridinyl which is substituted, once or twice, by a hydroxyl group and can be substituted, once or more than once, by a substituent selected from the group comprising $C_1$–$C_{18}$alkyl, $C_1$–$C_{18}$alkoxy, halogen, nitro and amino; $R_2$ is $C_1$–$C_{18}$-alkyl or $C_1$–$C_{18}$alkyl which is substituted, once or more than once, independently of each other, by OH, SH, $NH_2$, carboxamide or C(O)O—$C_1$–$C_{18}$alkyl; $R_3$ is methyl; and X is —C(O)—, —C(S)—, —C(O)Y— or —C(S)Y—, where Y is NH— or O—$C_1$–$C_6$alkylene. Compounds are particularly preferred in which $R_1$ is phenyl which is substituted, once or twice, by a hydroxyl group and can be substituted, once or twice, by a substituent selected from the group comprising $C_1$–$C_{18}$alkyl, $C_1$–$C_{18}$alkoxy, halogen, nitro and amino; pyrimidinyl which is substituted twice by a hydroxyl group; quinolinyl which is substituted by one or two hydroxyl group(s), pyridinyl which is substituted once by a hydroxyl group; or pteridinyl which is substituted once by a hydroxyl group and can be substituted by an amino group; $R_2$ is $C_1$–$C_{18}$alkyl which is unsubstituted or substituted once or more than once, independently of each other, by OH, SH, $NH_2$, carboxamide or C(O)O—$CH_3$; $R_3$ is methyl; and X is —C(O)— or —C(O)Y—, where Y is O—$C_1$–$C_6$alkylene.

Those compounds of the formula I or II form another preferred embodiment in which $R_1$ is 2-hydroxyphenyl; 2,4-dihydroxyphenyl; 3,4-dihydroxyphenyl; 3,5dihydroxyphenyl; 4-hydroxy-3-methoxyphenyl; 4-hydroxy-3,5-dimethoxyphenyl; 3-fluoro-6-hydroxyphenyl; 2-hydroxy-5-methylphenyl; 3-hydroxy-4-nitrophenyl; 3-hydroxy-4-aminophenyl; 3,5-dihydroxypyrimidinyl; 3-(6-hydroxy)pyridinyl; 2-(8-hydroxy)quinolinyl; 6-(2-amino-8-hydroxy)pteridinyl; or 2-(4,8-dihydroxy)quinolinyl; $R_2$ is —$(CH_2)_8COOCH_3$; $R_3$ is methyl; and X is —C(O)— or —C(O)Y—, where Y is O—$CH_2$—.

Those compounds are particularly preferred in which $R_1$ is 2-4-dihydroxyphenyl; 3,4-dihydroxyphenyl; 3,5-dihydroxyphenyl; 3-fluoro-6hydroxyphenyl; 3,5-dihydroxypyrimidinyl; 2-(8-hydroxy)quinolinyl, 2-(4,8-dihydroxy)quinolinyl or 6-(2-amino-8-hydroxy)pteridinyl; in particular 2-4-dihydroxyphenyl; 3,5-dihydroxypyrimidinyl, 2-(8-hydroxy)quinolinyl or 2-(4,8-dihydroxy)quinolinyl; $R_2$ is —$(CH_2)_8COOCH_3$; $R_3$ is methyl; and X is —C(O)— or —C(O)Y—, where Y is O—$CH_2$—.

The most preferred compounds of the formula I are those in which (a) $R_2$ is —$(CH_2)_8COOCH_3$, $R_3$ is methyl, X is —C(O)— and $R_1$ is 3,5-dihydroxypyrimidinyl; 2-hydroxyphenyl; 3,4-dihydroxyphenyl; 3,5-dihydroxyphenyl; 4-hydroxy-3-methoxyphenyl; 4-hydroxy-3,5-dimethoxyphenyl; 2,4-dihydroxyphenyl; 3-fluoro-6-hydroxyphenyl; 2-hydroxy-5methylphenyl; 3hydroxy-4-nitrophenyl; 3-hydroxy-4-aminophenyl; 3-(6hydroxy)pyridinyl; 2-(8hydroxy)quinolinyl; 6-(2-amino-8-hydroxy)pteridinyl; or 2-(4,8-dihydroxy)quinolinyl; or (b) $R_2$ is —$(CH_2)_8COOCH_3$, $R_3$ is methyl and X is —C(O)Y—, in which Y is O—$CH_2$—, and $R_1$ is 3,5-dihydroxyphenyl.

The most preferred compounds of the formula II are those in which (a) $R_2$ is —$(CH_2)_8COOCH_3$, $R_3$ is methyl, X is —C(O)— and $R_1$ is 3,5-dihydroxyphenyl; 4-hydroxy-3,5-dimethoxyphenyl; 3,4-dihydroxyphenyl; 3,5-dihydroxypyrimidinyl; 2-(8-hydroxy)quinolinyl; 3-fluoro-6-hydroxyphenyl; 4-hydroxy-3-methoxyphenyl or 2-(4,8-dihydroxy)quinolinyl; or (b) $R_2$ is —$(CH_2)_8COOCH_3$, $R_3$ is methyl and X is —C(O)Y—, in which Y is O—$CH_2$—, and $R_1$ is 3,5-dihydroxyphenyl.

The present invention also provides a process for preparing compounds of the formula I by (a) reacting a compound of the formula V $$R_7-X'-R_1 \qquad (V),$$

in which (a') $R_7$ is halogen, X' has the abovementioned meanings of X and $R_1$ is as already defined above, or (a") $R_7$ is C(O) or C(S), X' is —N= and $R_1$ is as defined above, or (a'") $R_7$ is OH, X' has the abovementioned meanings of X and $R_1$ is as already defined above, directly after the in-situ activation in analogy with methods which are customary in peptide chemistry [Bodansky, M., Principles of Peptide Chemistry, 2nd Ed. 16–61, Springer Berlin (1993)], with a compound of the formula IV

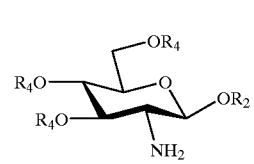

(IV)

in which $R_2$ is as defined above and the individual $R_4$s are, independently of each other, hydrogen or a protecting group, for example selected from the group comprising acetyl, propionyl, butyroyl and benzoyl, with the elimination of any protecting groups which are present using, for example, a basic alcohol solution, to form a compound of the formula VI

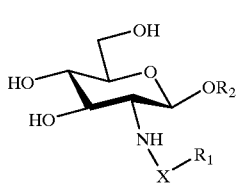 (VI)

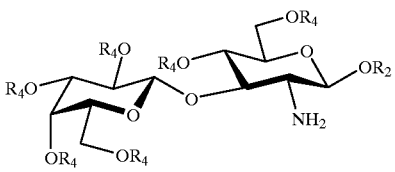 (IX)

in which $R_2$, $R_1$ and X are as previously defined;

(b) reacting the compound of the formula VI with uridine diphosphate galactose in the presence of β(1→4)galactosyl transferase, and then with cytidine monophosphate sialic acid in the presence of sialyl transferase, to form a compound of the formula VII in which $R_2$ and the individual $R_4$s are as defined above, with the elimination of any protecting groups which are present using, for example, a basic alcohol solution, to form a compound of the formula X

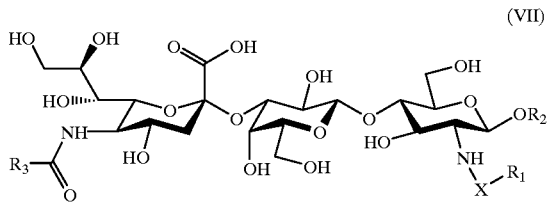 (VII)

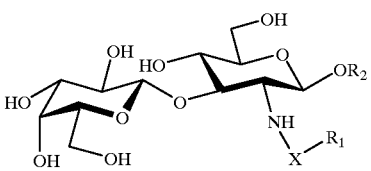 (X)

in which $R_1$, $R_2$, $R_3$ and X are as previously defined, and (c) reacting the resulting product with guanosine diphosphate fucose in the presence of fucosyl transferase to form a compound of the formula I.

The invention also provides a process for preparing compounds of the formula I by (a) reacting a compound of the formula VI with uridine diphosphate galactose in the presence of β(1→4)galactosyl transferase, and then with cytidine monophosphate sialic acid in the presence of sialyl transferase, to form a compound of the formula VII, and (b) reacting the resulting product with guanosine diphosphate fucose in the presence of fucosyl transferase to form a compound of the formula I.

The present invention also provides a process for preparing compounds of the formula II by (a) reacting a compound of the formula VI with uridine diphosphate galactose in the presence of β(1→3)galactosyl transferase, and then with cytidine monophosphate sialic acid in the presence of sialyl transferase, to form a compound of the formula VIII in which $R_2$, $R_1$ and X are as previously defined;

(b) reacting the compound of the formula X with cytidine monophosphate sialic acid in the presence of sialyl transferase to form a compound of the formula VIII

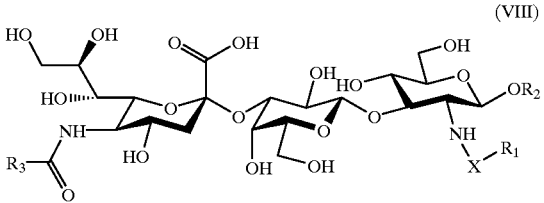 (VIII)

in which $R_1$, $R_2$, $R_3$ and X are as previously defined, and (c) reacting the resulting product with guanosine diphosphate fucose in the presence of fucosyl transferase to form a compound of the formula II.

The present invention also provides a process for preparing compounds of the formula II by (a) reacting a compound of the formula X with cytidine monophosphate sialic acid in the presence of sialyl transferase to form a compound of the formula VIII, and (b) reacting the resulting product with guanosine diphosphate fucose in the presence of fucosyl transferase to form a compound of the formula II.

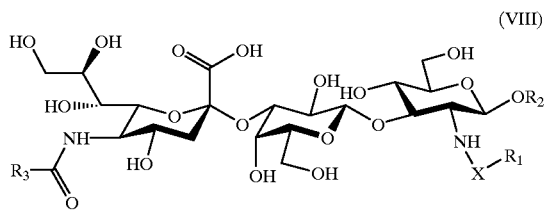 (VIII)

Using the novel enzymic process, oligosaccharide structures can be prepared more efficiently as compared with the previous chemical syntheses and highly modified, non-natural substrates can be glycosylated enzymically in a highly regioselective and stereo-selective manner, with it being possible to prepare the novel compounds without using heavy metal promoters (e.g. $Hg^{2+}$ salts), as are customarily employed in chemical glycosylations.

The compounds of the formulae IV and V are known or can be prepared using known methods. The compounds of the formula IX are novel and likewise part of the subject-matter of the present invention. They can be synthesized using a method due to Lemieux et al. and Boullanger et al. [Lemieux, R. U., Bundle, D. R., Baker, D. A., J. Am. Chem. Soc. 97:4076–4083 (1975); Boullanger, P., Banoub, J., Descotes, G., Can. J. Chem. 65:1343–1348 (1987)].

in which $R_1$, $R_2$, $R_3$ and X are as previously defined, and (b) reacting the resulting product with guanosine diphosphate fucose in the presence of fucosyl transferase to form a compound of the formula II.

The present invention also provides a process for preparing compounds of the formula II by (a) reacting a compound of the formula V, directly after the in-situ activation in analogy with methods which are customary in peptide chemistry, with a compound of the formula IX The amidation of compounds of the formulae IV and IX can be performed in a variety of ways, depending on the meaning of $R_1$, $R_7$ and X [Bodansky, M., Principles of Peptide Chemistry, 2nd Ed. 9–62, Springer Berlin (1993)].

For example, when (a) $R_7$ is OH and X and $R_1$ are as defined above, the amidation can be effected directly, after the compounds of the formula V have previously been activated with a diimidazole, for example carbonyldiimidazole (CDI), in a polar non-protic solvent, such as dimethylformamide (DMF) or acetonitrile.

(b) In the case of these compounds of the formulae IV and IX, the amidation can also be effected once the aromatic OH groups have first of all been protected, for example acetylated or benzoylated [McCorkindale, N. J., Roy, T. P., Hutchinson, S. A., Tetrahedron 2:1107–1111 (1972)]. The acid function can then be converted into the acid chloride using an inorganic acid chloride, for example thionyl chloride. These are then coupled, in the presence of a base, for example triethylamine, and in a solvent, such as dichloromethane, with the amine of the formula IV or IX and converted, by addition of a basic alcohol solution, for example methanol solution, into the glucosamide derivatives of the formula VI or X.

(c) Couplable chlorides of the formula V, in which $R_7$ is Cl, X is $C(O)$—$C_1$–$C_6$alkylene and $R_1$ is defined as above, are obtained by acetylating the aromatic OH groups of the corresponding carboxylic acid and firstly reducing the free acid function to the benzylic OH group using diborane [McCorkindale, N. J., Roy, T. P., Hutchinson, S. A., Tetrahedron 2:1107–1111 (1972)]. This is converted with phosgene into the corresponding alkoxycarbonyl chloride of the formula V [Petersen, S. in: Müller, E. (Ed.) Methoden der Organischen Chemie (Methods of Organic Chemistry) (Houben-Weyl) 8:102 (1952)].

After removing the solvent, the amide derivatives of the formulae VI and X can be purified chromatographically, for example on silica gel (eluent: for example dichloromethane/methanol mixtures) and then lyophilized.

The enzymes which are used for preparing compounds of the formulae I and II are commercially available or can be obtained using known methods. For example, the galactosyl transferase which is used in the present case for the enzymic β(1→4)galactosylation can be obtained from Boehringer. β-specific galactosylation of the 4-OH function of the glucosamine takes place exclusively [Palcic, M. M., Methods Enzymol. 230:300–316 (1994)]. The galactosyl transferase which is used for the β(1→3)galactosylation can be produced, for example, by recombinant means (JPN 06181759 A2, Appl. JP 92-336436921216). β-specific galactosylation on the 3-OH function of the N-acylglucosamide takes place exclusively.

The sialyl transferase is preferably a microbially produced sialyl transferase (WO 91/06635); it was originally found in rat liver. A strictly α-specific sialylation of the 3-OH group of the terminal galactose takes place [Palcic, M. M., Methods Enzymol. 230:300–316 (1994)].

The microbially produced (fuc-t VI) fucosyl transferase transfers the fucose in an α-specific manner to the 3-OH group of the N-acylglucosamine unit [Palcic, M. M., Methods Enzymol. 230:300–316 (1994)]. The (fuc-t III) fucosyl transferase, which is likewise microbially produced, transfers the fucose in an α-specific manner to the 4-OH group of the N-acylglucosamine unit (WO 91/12340).

The enzymic reactions are advantageously carried out in the presence of from 0.1 U to 5 U of the enzyme concerned. It has been found to be advantageous to employ the glycosyl donor in excess. Good results are achieved when, for example, from 1.2 to 2 equivalents of uridine diphosphate galactose, from 1.2 to 2.3 equivalents of cytidine mono-phosphate sialic acid or from 1.2 to 2.5 equivalents of guanosine diphosphate fucose are employed.

The UDP-galactose can be obtained commercially or synthesized chemoenzymically. For this purpose, hydroxyl protecting groups of the formula —C(O)—R of the sugar residue, in which R is linear or branched alkyl, preferably $C_1$–$C_8$alkyl, particularly preferably $C_1$–$C_4$alkyl, unsubstituted phenyl or phenyl which is substituted by $C_1$–$C_4$alkyl or $C_1$–$C_4$alkoxy, are eliminated enzymically from a protected UDP-galactose. Examples of hydroxyl protecting groups are protecting groups of the formula —C(O)—R, in which R is methyl, ethyl, n- and i-propyl, n-, i-, s- and t-butyl and also pentyl, hexyl, heptyl and octyl, with all possible isomers, or is unsubstituted phenyl or phenyl which is substituted, once to three times, identically or differently, by a substituent selected from the group comprising methyl, ethyl, n- and i-propyl, n-, i-, s- and t-butyl, methoxy, ethoxy, n- and i-propoxy, n-, i-, s- and t-butoxy. Examples of substituted phenyl derive from toluene, o-, m- and p-xylene, pseudocumene, mesitylene, trimethylbenzene, ethylbenzene, dimethylpropylbenzene and cumene. This process can be carried out using soluble or immobilized enzymes. The choice of the enzyme depends on the nature of the protecting groups and on the stereochemistry of the sugar. In this context, it has proved to be advantageous to use a functionally homogeneous enzyme or an enzyme mixture. If the protecting group is a —C(O)—$CH_3$ radical, it is eliminated using an acetyl esterase. If it is a —C(O)—$CH_2CH_3$ radical, the protecting group is then eliminated using an acetyl esterase, a lipase or a mixture of these two enzymes. Lipases are preferably employed for eliminating the —C(O)—$C_3$–$C_8$alkyl, unsubstituted —C(O)-phenyl or substituted —C(O)-phenyl. The enzymes can come from natural sources, such as animals, microorganisms or plants, or else be produced recombinantly. Commercially available enzymes, for example vegetable enzymes such as the acetyl esterase from orange peel (EC 3.1.1.6) are particularly advantageous. The reaction can take place either in the presence or the absence of buffers. If buffers are present, these are advantageously electrolytic buffers such as NaCl, $MgHPO_4$, 2-morpholinoethanesulfonic acid monohydrate-NaOH, N-(2-acetamino)-2-aminoethanesulfonic acid-NaOH-NaCl, 3-morpholinopropanesulfonic acid-NaOH-NaCl, N-tris(hydroxymethyl)methyl-2-aminoethanesulfonic acid-NaOH-NaCl, 4-(2-hydroxyethyl)piperazine-1-ethanesulfonic acid-NaOH-NaCl and imidazole-HCl-NaCl. The reaction preferably takes place in a temperature range between room temperature and 40° C., preferably at 37° C. The pH is expediently in a range between pH 6.5 and pH 7.5, preferably at pH 7, and is advantageously kept constant automatically, for example using pH probes and automated metering equipment. Otherwise, the choice of the buffer, the temperature and the pH depends on the enzyme which is used in each case and on the substrate to be converted and can certainly, in particular cases, lie outside the given ranges. The process can also be carried out such that either the sugar-1-phosphate or the corresponding nucleoside is activated with a carbonyl-bis-azole before the coupling and the protecting groups are eliminated enzymically after the coupling. Examples of carbonyl-bis-azoles are carbonyldiimidazole, carbonylditriazole, thiocarbonyldiimidazole and carbonyldioxydibenzotriazole. For example, protected monophosphoric acid sugar esters are reacted with an excess of carbonyl-bis-azole in the presence of a polar solvent. The excess carbonyldiazole is then advantageously destroyed using an accurately metered quantity of absolute methanol. After this activation, the activated sugar phosphates are reacted, in situ or after isolation, with trialkylammonium salts of the nucleotide building blocks to form the protected nucleoside di- or tri-phosphate sugars. The imidazole salt which primarily results is then filtered through an ion exchanger in order to exchange it for an arbitrary ion Q. Further purification can then be effected on reversed-phase silica gels or by precipitation with suitable precipitating agents such as ethanol or ethanol/isopropanol or ethanol/acetone mixtures. Advantageously, the reaction is performed in the absence of water in a dry, polar, non-hydroxylic solvent in a temperature range between room temperature and 80° C., preferably in a range between 40° C. and 50° C., in particular at 40° C. It has been found to be advantageous to carry out the reaction in an ultrasonication bath. Examples of polar, non-hydroxylic solvents are dimethylformamide, dimethyl sulfoxide, acetone, dioxane, pyridine and acetonitrile, and also mixtures thereof.

While the CMP-sialic acid donor in which $R_3$ is methyl is commercially available, it can also, like the corresponding donor in which $R_3$ is hydroxymethyl, advantageously be prepared enzymically [Heidlas, J. E., Williams, K. W., Whitesides, G. M., Acc. Chem. Res. 25:307–314 (1992)].

GDP-fucose can be used as donor for the last preparation step. It can advantageously be prepared chemoenzymically, as described above for UDP-galactose.

The enzymic transfer of galactose and sialic acid can be effected either in a single step or in two consecutive steps.

Both the galactose donor (UDP-galactose) and the sialic acid donor (CMP-sialic acid) can be generated enzymically in situ from precursors in the presence of the corresponding transferases (→transfer reaction). UDP-galactose can be most expediently generated in this way from the commercially available UDP-glucose using the likewise commercially available UDP-glucose epimerase [E.C.5.1.3.2] (for example from Sigma) [Wong, C. H., Haynie, S. L., Whitesides, G. M., J. Am. Chem. Soc. 47:5416–5418 (1982)]. CMP-sialic acid can be generated from neuraminic acid, phosphoenolpyruvate and cytidine monophosphate in situ using the enzymes inorganic pyrophosphatase [E.C.3.6.1.1], myokinase [E.C.2.7.4.1], pyruvate kinase [E.C.2.7.1.40] and CMP-Sia synthetase [E.C.2.7.7.43] [Hayashi, M., Tanaka, M., Itoh, M., Miyauchi, H., J. Org. Chem. 61:2938–2945 (1996)].

All the final stages can also be prepared chemically using various methods of preparative carbohydrate chemistry [Barresi, F., Hindsgaul, O., Modern Synth. Methods 7:283–330 (1995)].

The amidations can be carried out in accordance with one of the current protocols, depending on the meaning of $R_1$, $R_2$, $R_4$, $R_7$ and X [for example Bodansky, M., Principles of Peptide Chemistry, 2nd Ed. 16–61, Springer Berlin (1993)]. For the enzymic syntheses using galactosyl transferase, sialic acid transferase and fucosyl transferase, it is advantageous to carry out the syntheses in the presence of buffers, such as sodium cacodylate, tris(hydroxymethyl) aminomethane or 4-(2-hydroxyethyl)piperazine-1-ethanesulfonic acid, in the pH and temperature ranges which are optimal in each case, for example in the range from pH 6 to pH 8 and in the range from 25° C. to 37° C. It has proved to be particularly advantageous if the incubation mixture contains salts, for example from 5 to 40 mM manganese II chloride, and auxiliary enzymes such as calf intestinal alkaline phosphatase (from 16 to 50 U).

The novel compounds have an increased physiological stability and an improved binding affinity for the corresponding selecting. The novel compounds can be employed as anti-adhesion therapeutic agents. In the case of pathogenic inflammations, they can prevent the selectin receptors on activated endothelial cells binding to sialyl-Lewis$^a$ structures and/or sialyl-Lewis$^x$ structures on the surface of leukocytes. In the case of tissue rejections, they can block corresponding receptors of the hematolymphoid cell system. The attachment of metastasizing cells, bacteria, viruses or other pathogens and toxins can likewise be prevented by blocking the corresponding receptors on the cell surface.

The invention also relates to the novel compounds for use in a therapeutic process for treating diseases in homeothermic animals, including man. When administering to homeothermic animals of about 70 kg bodyweight, the dose can, for example, be from 0.01 to 1000 mg per day. The administration is preferably effected in the form of pharmaceutical preparations, which are administered parenterally, for example intravenously or intraperitoneally.

The invention furthermore relates to a pharmaceutical preparation which comprises an effective quantity of the novel compound, either alone or together with other active compounds, a pharmaceutical carrier material, preferably in a significant quantity, and auxiliary substances, if desired.

The pharmacologically active novel compounds can be used in the form of parenterally administerable preparations or of infusion solutions. These solutions are preferably isotonic, aqueous solutions or suspensions, with it being possible, for example in the case of lyophilized preparations which comprise the active substance alone or together with a carrier material, for example mannitol, to prepare these latter before use. The pharmaceutical preparations can be sterilized and/or comprise auxiliary substances, for example preservatives, stabilizers, wetting agents, emulsifying agents, solubilizers, salts for regulating the osmotic pressure and/or buffers. The pharmaceutical preparations, which, if desired, can also comprise additional pharmacologically active compounds, such as antibiotics, are prepared in a manner known per se, for example by means of conventional solubilizing or lyophilizing methods, and comprise from about 0.1% to 90%, in particular from about 0.5% to about 30%, for example from 1% to 5%, of active compound(s).

The following examples explain the invention in more detail.

Abbreviations used are:

DMSO: dimethyl sulfoxide; DMF: dimethylformamide; Ac: acetate; Ph: phenyl; HRP: horseradish peroxidase; BSA: bovine serum albumin; CDI: carbonyldiimidazole; RT: room temperature; UDP-gal: uridine diphosphate-galactose; CMP-sia: cytidine monophosphate-sialic acid; GDP-fuc: guanosine diphosphatefucose; TBTU: O-(benzotriazol-1-yl N,N,N',N'-tetramethyluronium tetrafluoroborate; HBPyU: O-(benzotriazol-1-yl)-N,N,N',N'-bis-(tetramethylene) uronium hexafluorophosphate; THF: tetrahydrofuran; HBTU: O-(1H-benzotriazol-1 -yl)N,N,N',N'-tetramethyluronium hexafluorophosphate; d: doublet; dd: doublet of doublets; m: multiplet; s: singlet; t: triplet; q: quartet.

The % indication in connection with solutions denotes vol/vol.

A: PREPARATION OF THE STARTING COMPOUNDS

Example A1

Preparation of Compound No. 64

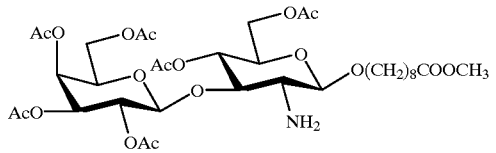
(64)

(a) 8.63 g (20.0 mmol) of α,β-1,3,4,6-tetra-O-acetyl-2-deoxy-2-N-allyloxycarbonylglucose [Boullanger, P., Jouineau, M., Bouammali, B., Lafont, D., Descotes, G., Carbohydr. Res. 202:151–164 (1990)] are reacted, in accordance with a known method [Lafont, D., Manaudier, S., Boullanger, P., Descotes, G., Bull. Soc. Chim. Fr. 127:576–583 (1990)], at −30° C. and in 150 ml of dichloromethane, with 5.65 g (30.0 mmol) of methyl 9-hydroxynonanecarboxylate [Lemieux, R. U., Bundle, D. R., Baker, D. A., J. Am. Chem. Soc. 97:4076–4083 (1975)] in the presence of 10.3 ml (56.0 mmol) of methyl trifluoromethanesulfonate (Fluka). After chromatographing the reaction mixture on silica gel (eluent: petroleum ether/ethyl acetate-2/1), 11.14 g (quant.) are obtained of the compound No. (31).

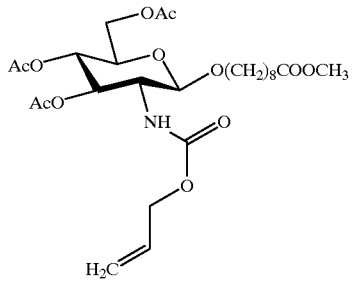
(31)

(b) 5.15 g (9.2 mmol) of the monosaccharide No. (31) are added, under an argon atmosphere and at RT, to 30 ml of dry methanol in which 15.0 mg (0.65 mmol) of sodium have previously been dissolved. After approximately 1 h, the sugar is completely deacetylated. The reaction mixture is then poured onto a strongly acidic ion exchanger (DOWEX 8×50 strongly acidic, Fluka), after which the whole is shaken for 15 min and the ion exchanger is filtered off; the later is washed again with approximately 100 ml of methanol, and the combined organic phases are evaporated. The resulting white powder is dried under high vacuum. 3.95 g (99%) are obtained of deprotected sugar No. (60).

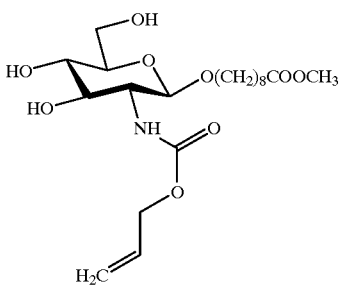
(60)

$^1$H-NMR (CD$_3$OD, 250.13 MHz) δ=1.22 (m, 8 H); 1.47 (m, 4 H); 2.22 (t, 7.6 Hz, 2 H); 3.19–3.43 (m, 5 H); 3.55 (s, 3 H); 3.60 (dd, 5.5 Hz, 10.3 Hz, 1 H); 3.78 (m, 2 H); 4.25 (d, 7.3 Hz, 1 H); 4.42 (m, 2 H); 5.10 (broad d, 17.2 Hz, 1 H); 5.23 (broad d, 17.2 Hz, 1 H); 5.86 (m, 1 H). $^{13}$C-NMR (CD$_3$OD, 62.90 MHz) δ=26.00; 27.01; 30.11; 30.31; 30.34; 30.62; 34.77; 51.98; 59.00; 62.79; 66.36; 70.66; 72.13; 75.93; 77.81; 103.11; 117.30; 134.49; 158.88; 175.97.

(c) 9.7 g (22.4 mmol) of monosaccharide No. (60) are dissolved in 100 ml of dry THF. 6 ml (40.0 mmol) of benzaldehyde dimethylacetal (Fluka) and 250 mg of racemic camphor10-sulfonic acid are added in succession to this solution and the mixture is heated to 50° C. It is left to stir overnight until all the starting material has been consumed, after which it is cooled down to RT; 0.5 ml of triethylamine is then added before the solvent is evaporated off. The residue is chromatographed on silica gel (eluent: methylene chloride/methanol-20/1). 11.0 g (95%) are obtained of the 4,6-protected sugar No. (61).

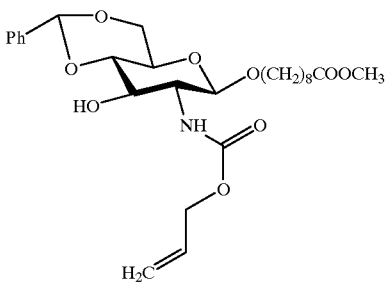
(61)

$^1$H-NMR (CDCl$_3$, 400.13 MHz) δ=1.23 (m, 8 H); 1.51 (m, 4 H); 2.23 (t, 7.6 Hz, 2 H); 3.25–3.50 (m, 5 H); 3.60 (s, 3 H); 3.70 (t, 9.7 Hz, 1 H); 3.78 (dt, 4.8 Hz, 9.7 Hz, 1 H); 4.25 (dd, 4.8 Hz, 10.9 Hz, 1 H); 4.50 (m, 2 H); 5.12 (m, 2 H); 5.23 (dq, 1.2 Hz, 16.3 Hz, 1 H); 5.45 (s, 1 H); 5.84 (m, 1 H); 7.30 (m, 3 H); 7.42 (m, 2 H). $^{13}$C-NMR (CDCl$_3$, 100.61 MHz) δ=24.77; 25.63; 28.91; 29.00; 29.35; 34.16; 51.46; 58.60; 65.73; 66.04; 68.59; 70.21; 70.69; 72.27; 81.49; 101.75; 117.60; 126.21 (2×C); 128.23 (2×C); 129.17; 132.46; 159.16; 174.53.

(d) 8.7 g (17.0 mmol) of benzyl-protected monosaccharide No. (61) and 5.5 g (22 mmol) of mercury cyanide are initially introduced in 260 ml of dry toluene/nitromethane (vol/vol-1/1) and this mixture is stirred, at RT for 30 min, with pulverized, active 4 Å molecular sieve (approx. 5 g). 10.3 g (25.0 mmol) of per-O-acetylated α-galactosyl bromide, dissolved in 35 ml of toluene/nitromethane (see above), are then added dropwise to this mixture and the whole is heated at 50° C. for approximately 18 h. After all the monosaccharide has reacted, the mixture is carefully filtered through Celite, the solvent is removed on a rotary evaporator and the remaining residue is chromatographed on silica gel (eluent: hexane/ethyl acetate-2/1). 9.1 g (64%) are obtained of disaccharide No. (62).

(62)

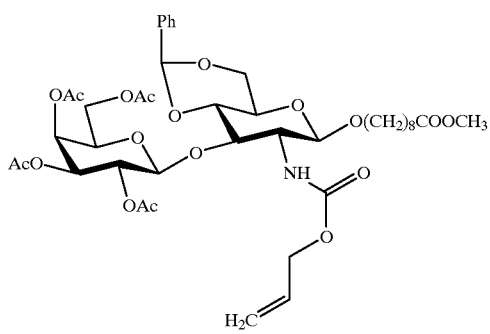

$^1$H-NMR (CDCl$_3$, 400.13 MHz) δ=1.22 (m, 8 H); 1.51 (m, 4 H); 1.88 (s, 3 H); 1.89 (s, 3 H); 1.91 (s, 3 H); 2.05 (s, 3 H); 2.23 (t, 7.6 Hz, 2 H); 3.06 (broad, 1 H); 3.41 (m, 2 H); 3.59 (m, 5 H); 3.71 (m, 2 H); 3.78 (dt, 6.1 Hz, 9.1 Hz, 1 H); 3.98 (dd, 6.6 Hz, 11.4 Hz, 1 H); 4.25 (dd, 6.1 Hz, 11.4 Hz, 1 H); 4.39 (m, 1 H); 4.50 (m, 2 H); 4.59 (d, 7.3 Hz, 1 H); 4.89 (dd, 3.6 Hz, 10.9 Hz, 1 H); 5.05 (m, 1 H); 5.13 (dd, 7.3 Hz, 10.9 Hz, 1 H); 5.19 (dq, 1.2 Hz, 11.5 Hz, 1 H); 5.22 (dd, 0.6 Hz, 3.0 Hz, 1 H); 5.27 (m, 1 H); 5.47 (s, 1 H); 5.86 (m, 1 H); 7.30 (m, 3 H); 7.40 (m, 2 H). $^{13}$C-NMR (CDCl$_3$, 62.90 MHz) δ=20.52 (2×C); 20.62 (2×C); 24.80; 25.65; 28.93; 29.00 (2×C); 29.38; 33.99; 51.44; 58.08; 60.70; 65.60; 65.87; 66.73; 68.70; 69.06; 70.27; 70.40; 70.97; 76.49; 78.63; 80.18; 101.01; 101.33; 117.88; 126.03 (2×C); 128.15 (2×C); 129.14; 132.44; 137.04; 155.43; 169.40; 170.06; 170.11; 170.24; 174.42.

(e) 9.1 g (10.7 mmol) of disaccharide No. (62) are dissolved in 100 ml of methylene chloride, and the solution is treated, at RT, with 5 ml of a 90% trifluoroacetic acid. After approx. 6 h, the mixture is neutralized with a saturated solution of sodium hydrogen carbonate, diluted with ethyl acetate and extracted successively with water and a saturated solution of sodium chloride. The organic phase is dried over sodium sulfate and concentrated by evaporation. The resulting residue is treated with 7 ml of pyridine and 3.5 ml of acetic anhydride, and stirred at RT overnight. The mixture is then diluted with ethyl acetate and extracted successively with 4 N hydrochloric acid, water and a saturated solution of sodium hydrogen carbonate. After the solvent has been evaporated off, a yellow syrup remains which is chromatographed on silica gel (eluent: petroleum ether/ethyl acetate-2/1). 6.9 g (76%) are obtained of disaccharide No. (63).

(63)

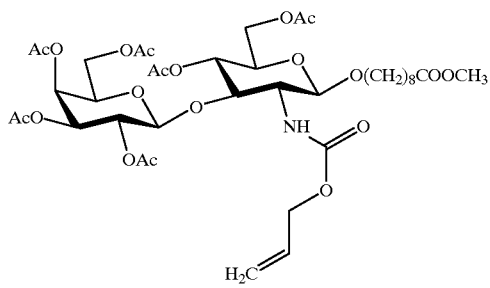

$^1$H-NMR (CDCl$_3$, 400.13 MHz) δ=1.22 (m, 8 H); 1.51 (m, 4 H); 1.93 (s, 3 H); 1.98 (s, 3 H); 2.00 (s, 3 H); 2.01 (s, 3 H); 2.09 (s, 3 H); 2.17 (s, 3 H); 2.24 (t, 7.6 Hz, 2 H); 3.10 (m, 1 H); 3.39 (dt, 6.0 Hz, 10.9 Hz, I H); 3.58 (m, 1 H); 3.60 (s, 3 H); 3.79 (m, 2 H); 4.04 (m, 3 H); 4.17 (dd, 6.0 Hz, 11.0 Hz, 1 H); 4.80 (m, 1 H); 4.52 (m, 3 H); 4.66 (m, 1 H); 4.88 (m, 2 H); 4.99 (m, 1 H); 5.01 (dd, 7.3 Hz, 11.5 Hz, 1 H); 5.19 (dq, 0.6 Hz, 12.1 Hz, 1 H); 5.28 (m, 2 H); 5.27 (m,$_1$ H); 5.90 (m, 1 H). $^{13}$C-NMR (CDCl$_3$, 62.90 MHz) δ=20.50; 20.61 (3×C); 20.67; 20.79; 24.79; 25.63; 28.91; 28.97; 29.01; 29.30; 33.99; 51.43; 58.02; 60.98; 62.44; 65.59; 66.76 (2×C); 69.00; 69.15; 70.00; 70.42; 70.95; 71.65; 100.55; 101.02; 117.91; 137.50; 155.55; 169.15; 169.27; 170.11; 170.19; 170.32; 170.75; 174.29.

(f) 4.0 g (4.7 mmol) of disaccharide No. (63) are dissolved, under argon and at RT, in 60 ml of absolute THF, and this solution is treated successively with 5.6 ml of diethyl malonate and 0.4 g (0.3 mmol) of tetrakis(triphenyl) palladium (Fluka). After 1 h, the solvent is evaporated off and the remaining residue is chromatographed on silica gel. 3.1 g (89%) are obtained of amine No. (64).

$^1$H-NMR (CDCl$_3$, 250.13 MHz) δ=1.33 (m, 8 H); 1.60 (m, 4 H); 1.99 (s,3 H); 2.05 (m, 12); 2.13 (s, 3 H); 2.29 (t, 7.6 Hz, 2 H); 2.92 (dd, 7.5 Hz, 8.2 Hz, 1 H); 3.46 (dt, 6.9 Hz, 10.3 Hz, 1 H); 3.58 (m, 1 H); 3.67 (s, 3 H); 3.89 (m, 2 H); 4.14 (m, 6 H); 4.73 (d, 7.6 Hz, 1 H); 4.99 (m, 2 H); 5.15 (dd, 7.6 Hz, 11.7 Hz, 1 H); 5.35 (m, 1 H). $^{13}$C-NMR (CDCl$_3$, 62.90 MHz) δ=20.50; 20.60 (3×C); 20.77; 20.81; 24.82; 25.83; 28.98; 29.09 (2×C); 29.42; 33.99; 51.40; 57.05; 60.91; 62.51; 66.74; 68.70; 69.52; 70.16; 70.58; 70.97; 72.04; 83.53; 101.45; 103.12; 169.03; 169.30; 170.13; 170.29; 170.75; 174.44.

Example A2

Preparation of Compound No.2

(2)

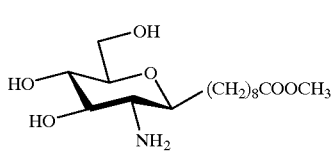

(a) 22.4 g (40.0 mmol) of the fully protected compound No. (31) are dissolved, at RT, in 200 ml of dry methanol, and this solution is treated with 5 ml of a 5% solution of sodium methoxide. After 5 h at RT, the mixture is neutralized with DOWEX-H$^+$ (50W×8), the ion exchanger is filtered off and the solvent is evaporated off. After drying under high vacuum, 17.2 g (99%) are obtained of the deacetylated intermediate No. (2a).

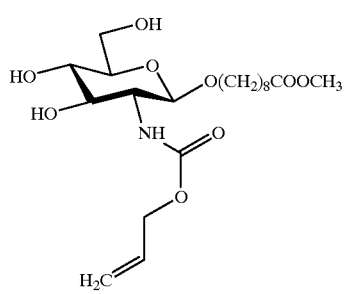

(2a)

$^1$H-NMR (CD$_3$OD, 250.13 MHz) δ=1.28 (m, 8 H); 1.48 (m, 4 H); 2.21 (t, 7.6 Hz, 2 H); 3.07–3.39 (m, 5 H); 3.56 (m, 4 H); 4.78 (m, 2 H); 4.23 (d, 7.3 Hz, 1 H); 4.42 (m, 2 H); 5.08 (dq, 0.6 Hz, 12.1 Hz, 1 H); 5.22 (broad d, 12.1 Hz, 1 H); 5.84 (m, 1H). $^{13}$C-NMR (CDCl$_3$, 62.90 MHz) δ=26.00; 27.01; 30.11; 30.31; 30.34; 30.62; 34.77; 51.98; 59.00; 62.79; 66.36; 70.66; 72.13; 75.93; 77.81; 103.11; 117.30; 134.49; 158.85; 175.97; 170.06; 173.59.

(b) 1.1 g (2.5 mmol) of the intermediate No. (2a) are dissolved, under argon and at RT, in a dioxane/THF/methanol (2 ml/5 ml/10 ml) solvent mixture to form a clear solution, and this solution is treated successively with 0.5 g (3.9 mmol) of sodium thiophenolate, 43 mg (0.1 mmol) of 1,4-bis(diphenylphosphino)butane (Fluka) and 49 mg (0.5 mmol) of tris-(dibenzylideneacetone)dipalladium(0) complex (Aldrich). After 3 h at RT, the solvent is evaporated off and the residue is chromatographed on silica gel (eluent: methylene chloride/methanol-10/2). 0.8 g (93%) of amine No. (2) is obtained as a colourless solid.

$^1$H-NMR (CD$_3$OD, 250.13 MHz) δ=1.22 (m, 8 H); 1.50 (m, 4 H); 2.20 (t, 7.6 Hz, 2 H); 2.49 (broad t, 8.3 Hz, 1 H); 3.28 (m, 3 H); 3.40 (dt, 6.2 Hz, 8.2 Hz, 1 H); 3.56 (m, 4 H); 4.15 (d, 7.3 Hz, 1 H). $^{13}$C-NMR (CDCl$_3$, 62.90 MHz) δ=25.95; 27.05; 30.07; 30.27; 30.31; 30.65; 34.75; 51.97; 58.23; 62.64; 70.73; 71.78; 77.16; 78.08; 104.07; 175.93.

Example A3

Preparation of Compound No. 32

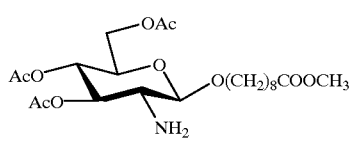

(32)

The N-allyloxycarbonyl protecting group of the compound No. (31) can be removed in accordance with various protocols using palladium-O as catalyst [Boullanger, P., Banoub, J., Descotes, G., Can. J. Chem. 65:1343–1348 (1987) or Genêt, J. P., Blart, E., Savignac, M., Lemeune, S., Lemaire-Audoire, S., Bernard, J. M., Synlett 680–682 (1993)]. 3.9 g (76%) of the free amine No. (32) are obtained in this way from 6.0 g (10.7 mmol) of compound No. (31).

$^1$H-NMR (CD$_3$OD, 250.13 MHz) δ=1.34 (m, 8 H); 1.64 (m, 4 H); 2.06 (s, 3 H); 2.11 (s, 6 H); 2.33 (t, 7.6 Hz, 2 H); 2.95 (dd, 2.1 Hz, 8.3 Hz, 1 H); 3.52 (dt, 7.6 Hz, 8.3 Hz, 1 H); 3.71 (m, 4 H); 3.93 (dt, 7.6 Hz, 8.3 Hz, 1 H); 4.15 (dd, 2.1 Hz, 11.0 Hz, 1 H); 4.28 (d, 7.3 Hz, 1 H); 4.72 (dd, 5.5 Hz, 11.0 Hz, 1 H); 5.02 (m, 2 H). $^{13}$C-NMR (CDCl$_3$, 62.90 MHz) δ=20.17; 20.25; 20.31; 24.37; 25.37; 28.51; 28.63 (2×C); 28.99; 33.48; 50.90; 55.48; 61.82; 68.47; 69.74; 71.26; 74.90; 103.57; 169.22; 170.06; 173.59.

Example A4

Preparation of Compound No. 90

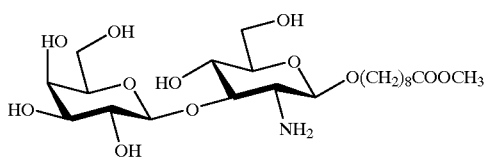

(90)

(a) 7.0 g (8.2 mmol) of the completely protected disaccharide No. (62) are suspended, at RT, in 80 ml of methylene chloride, and this suspension is treated, while being stirred vigorously, with 5 ml of 90% trifluoroacetic acid. After 5 h at RT, the solution, which is now clear, is diluted with methylene chloride and extracted successively with a saturated solution of sodium hydrogen carbonate and with water. The organic phase is dried over magnesium sulfate and then concentrated by evaporation. The residue is chromatographed through silica gel (eluent: petroleum ether/ethyl acetate-1/1). 5.24 g (84%) of the compound No. (88) are obtained as a colourless syrup.

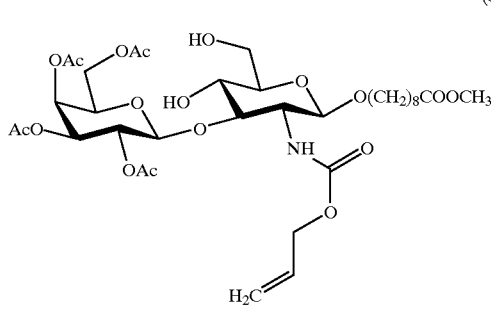

(88)

$^1$H-NMR (CDCl$_3$, 400.13 MHz) δ=1.24 (m, 8 H); 1.40 (m, 4 H); 1.91 (s, 3 H); 1.98 (s, 3 H); 2.00 (s, 3 H); 2.09 (s, 3 H); 2.22 (t, 7.6 Hz, 2 H); 3.32 (m, 1 H); 3.41 (m, 2 H); 3.60 (s, 3 H); 3.71 (ddd, 6.0 Hz, 6.6 Hz, 12 Hz, 1 H); 3.79 (dt, 6.0 Hz, 10.2 Hz, 1 H); 3.85 (ddd, 4.2 Hz, 6.6 Hz, 10.2 Hz, 1 H); 3.96 (dd, 6.0 Hz, 7.2 Hz, 1 H); 4.03 (t, 10.8 Hz, 1 H); 4.09 (m, 2 H); 4.49 (m, 3 H); 4.95 (dd, 3.6 Hz, 10.8 Hz, 1 H); 5.14 (d, 9.0 Hz, 1 H); 5.18 (dq, 1.2 H, 11.4 Hz, 1 H); 5.26 (dq, 1.2 Hz, 16.2 Hz, 1 H); 5.31 (broad d, 3.6 Hz, 1 H); 5.84 (m, 1 H). $^{13}$C-NMR (CDCl$_3$, 100.6 MHz) δ=20.45 (3×C); 20.46; 24.37; 25.60; 28.85; 28.95 (2); 29.32; 33.91; 51.37; 57.16; 61.68; 62.78; 65.55; 66.82; 68.60; 69.97; 70.40; 70.62; 71.03; 74.91; 84.78; 99.74; 101.90; 117.85; 132.36; 155.82; 169.47; 169.93; 170.03; 170.39; 174.25.

(b) 5.24 g (6.86 mmol) of compound No. (88) are dissolved in 100 ml of dry methanol, and this solution is treated with 7 ml of a 1% solution of sodium methoxide. After 1 h at RT, the mixture is neutralized with a strongly acidic ion exchanger (DOWEX 50×8), followed by filtration and concentration by evaporation. 4.08 g (100%) are obtained of the solid disaccharide No. (89).

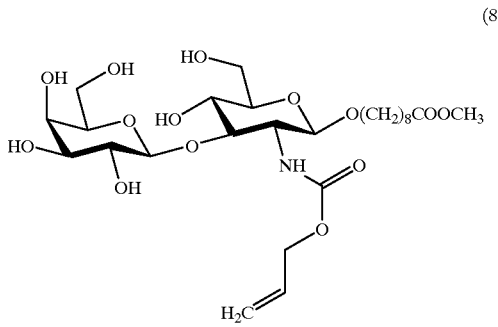

(89)

$^1$H-NMR (D$_2$O-CD$_3$OD, 400.13 MHz) δ=1.26–1.41 (m, 8 H); 1.50–1.68 (m, 4 H); 2.32 (t, 7.6 Hz, 2 H); 3.28–3.94 (m, 17 H); 4.31 (broad d, 8.8 Hz, 1 H); 4.41–4.62 (m, 3 H); 5.18 (broad d, 11.0 Hz, 1 H); 5.32 (broad d, 16.9 Hz, 1 H); 5.93 (m, 1 H). $^{13}$C-NMR (D$_2$O-CD$_3$OD, 100.6 MHz) δ=25.97; 26.94; 30.05; 30.22; 30.27; 30.51; 34.80; 52.17; 58.37; 62.58 (2×C); 66.70; 70.14; 70.49; 70.88; 72.66; 74.71; 76.99; 77.27; 84.70; 102.92; 105.10; 117.62; 134.34; 159.51; 176.14.

(c) 4.08 g (6.8 mmol) of disaccharide No. (89) are dissolved, at RT and under an argon atmosphere, in 160 ml of oxygen-free THF and 50 ml of methanol. While stirring vigorously, 0.75 g (1.8 mmol) of 1,4-bis(diphenylphosphino)butane (Fluka), 1.50 g (11.3 mmol) of sodium thiophenolate (Fluka) and 0.58 g (0.6 mmol) of tris(dibenzylideneacetone)-dipalladium(0) complex (Aldrich) are added in succession and the mixture is stirred at RT for 1 d. After evaporating off the solvent, the remaining residue is chromatographed on silica gel (eluent: methylene chloride/methanol/water—10/4/0.5). 2.23 g (64%) are obtained of amine No. (90).

$^1$H-NMR (D$_2$O-CD$_3$OD, 400.13 MHz) δ=1.13–1.29 (m, 8 H); 1.41–1.52 (m, 4 H); 2.19 (t, 7.6 Hz, 2 H); 2.75 (broad t, 7.8 Hz, 1 H); 3.19 (m, 1 H); 3.29–3.82 (m, 15 H); 4.17 (d, 8.6 Hz, 1 H); 4.28 (d, 8.6 Hz, 1 H). $^{13}$C-NMR (D$_2$O-CD$_3$OD, 100.6 MHz) δ=25.90; 26.93; 29.28; 30.15; 30.20; 30.53; 34.79; 52.23; 57.46; 62.38; 62.44; 69.97; 70.12; 71.01; 72.52; 74.64; 77.06; 77.51; 88.17; 103.80; 105.81; 176.56.

B: Preparation of the Mimetics

Example B1.1

Preparation of Compound No. (1)

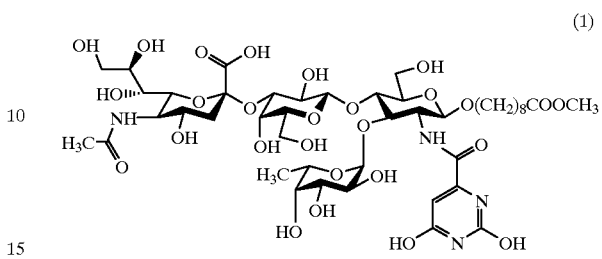

(1)

(a) 40 mg (256 μmol) of orotic acid (Fluka) are suspended in 3 ml of dry DMF, and this suspension is stirred at RT for 20 minutes with 42 mg of CDI. 90 mg (270 μmol) of compound No. (2) are added to the solution, which is now clear, and the mixture is stirred overnight. After chromatographic working-up on silica gel (eluent: methanol/methylene chloride/water mixtures) and lyophilization from dioxane/water, 33 mg (27%) of compound No. (3) are obtained as a white powder.

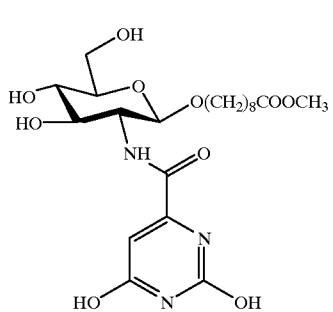

(3)

$^1$H-NMR ((D$_6$)-DMSO, 250.13 MHz) δ=1.28 (m, 8 H); 1.45 (m, 4 H); 2.26 (t, 7.5 Hz, 2 H); 3.14 (m, 2 H); 3.43 (m, 4 H); 3.59 (s, 3 H); 3.70 (m, 2 H); 4.39 (d, 8.2 Hz, 2 H); 6.11 (s, 1 H); 8.68 (broad d, 9.6 Hz, 1 H). $^{13}$C-NMR ((D$_6$)-DMSO, 62.89 MHz) δ=25.12; 26.21; 29.15; 29.41; 29.48; 29.70; 33.96; 51.87; 56.79; 61.56; 69.20; 71.07; 74.31; 77.71; 99.97; 101.33; 147.17; 153.16; 160.98; 165.20; 174.11.

(b) Galactosylation with β(1→4)galactosyl transferase 30 mg (63.1 μmol) of compound No. (3), 48 mg (78.4 μmol) of UDP-gal (Sigma), 2 mg of BSA (Boehringer) and 13 mg (65.1 μmol) of manganese(II) chloride tetrahydrate (Fluka) are together added to 1.8 ml of sodium cacodylate buffer (0.1 M, pH=7.52) (in this case, the buffer solution contains approximately 18% DMSO), and the mixture is sonicated briefly in an ultrasonication bath. 1 U of galactosyl transferase (Sigma, 400 μl of a solution containing 25 U/10 ml) and 44 U (2 μl) of bovine intestinal alkaline phosphatase (Boehringer) are added to the resulting homogeneous, milky suspension. The mixture is vortexed and incubated at 37° C.

with stirring. The reaction precipitates are centrifuged off, the clear supernatant is lyophilized from water/dioxane and the residue is purified chromatographically on silica gel (eluent: methylene chloride methanol/water mixtures). The solvent is removed, the residue is taken up in dioxane/water, and 24 mg of compound No. (4) (58%) are obtained as a white powder after renewed lyophilization.

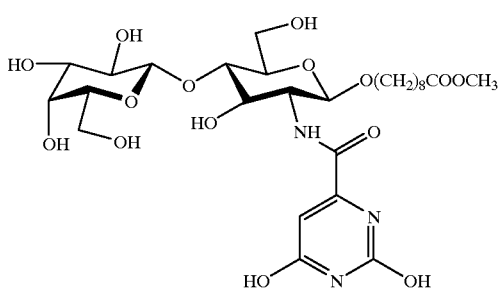

(4)

$^1$H-NMR ((D$_6$)-DMSO-CD$_3$OD-D$_2$O, 400.13 MHz) δ=1.18 (m, 8 H); 1.46 (m, 4 H); 2.22 (t, 7.5 Hz, 2 H); 3.32–3.86 (m, 14 H); 3.58 (s, 3 H); 4.44 (d, 8.6 Hz, 1 H); 6.12 (s, 1 H); remaining signals concealed by the solvent. $^{13}$C-NMR ((D$_6$)-DMSO-CD$_3$OD-D$_2$O, 62.89 MHz) δ=25.93; 26.98; 30.07; 30.24; 30.29; 30.49; 35.00; 52.45; 57.55; 62.05; 62.73; 70.49; 71.80; 72.46; 73.53; 74.99; 76.79; 76.91; 80.71; 100.81; 102.61; 105.20; 176.45; remaining signals not resolved.

(c) Sialylation with α(2→3)Sialyl Transferase 23 mg (35.4 μmol) of compound No. (4) are added to a mixture of 2 ml of a manganese(II) chloride solution (0.06 M), 2 ml of sodium cacodylate buffer (0.05 M, pH=6.5) (in this case, the buffer solution contains 8% DMSO) and 1.3 ml of double-distilled water in a plastic test-tube. The mixture is sonicated briefly in an ultrasonication bath. 35 mg (53.3 μmol) of CMP-sia (content, approx. 90%), 1.9 mg of BSA (Boehringer), 200 μl (1.4 U) of sialyl transferase and 2 μl (44 U) of bovine intestinal alkaline phosphatase (Boehringer) are then added, after which the whole is mixed and incubated at 37° C. while stirring. The reaction precipitates are centrifuged off. The clear supernatant is filtered through a reversed-phase C 18 column (eluent: methanol) and then purified through a silica gel column (eluent: methylene chloride/methanol/water mixtures). The solvent is removed and the residue is taken up in dioxane/water and this solution is lyophilized. 15 mg of compound No. (5) (47%) are obtained as a white powder.

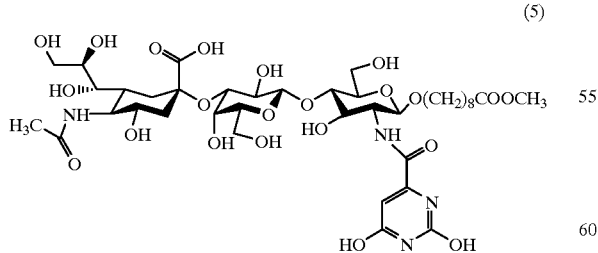

(5)

$^1$H-NMR (CD$_3$OD-D$_2$O, 250.13 MHz) δ=1.17 (m, 8 H); 1.45 (m, 4 H); 1.68 (broad t, 11.0 Hz, 1 H); 1.94 (s, 3 H); 2.20 (t, 7.6 Hz, 2 H); 2.74 (broad d, 11.0 Hz, 1 H); 3.29–4.02 (m, 24 H); 4.38 (d, 8.6 Hz, 1 H); 4.42 (d, 8.6 Hz, 1 H); 6.05 (s, 1 H). $^{13}$C-NMR (CD$_3$OD-D$_2$O, 62.89 MHz) δ=22.35; 25.72; 26.93; 29.84; 30.06; 30.19; 30.29; 34.48; 41.62; 51.70; 53.67; 57.00; 61.68; 62.44; 64.13; 68.87; 68.96; 69.02; 69.73; 70.58; 72.70; 73.46; 74.65; 76.31; 76.74; 77.36; 80.93; 100.43; 100.90; 102.16; 104.74; 166.82; 174.86; 175.26; 175.85; remaining signals not resolved.

(d) Fucosylation with Fucosyl Transferase VI 13 mg (13.8 μmol) of trisaccharide acceptor compound No. (5), 12.7 mg (19.7 mmol) of GDP-fuc and 1 mg of BSA (Boehringer) are added to a mixture of 150 μl of manganese (II) chloride solution (0.25 M), 450 μl of sodium cacodylate buffer (0.25 M, pH=6.48) and 600 μl of double-distilled water. 2 μl (32 U) of bovine intestinal alkaline phosphatase (Boehringer) and 150 μl (1.5 U) of a solution of fucosyl transferase VI are added, after which the whole is mixed and the mixture is incubated at 37° C. while stirring. The reaction precipitates are centrifuged off and the clear supernatant is passed through a reversed-phase C 18 column (eluent: methanol). The product-containing fractions are lyophilized from water/dioxane, filtered through a Na$^+$ column (Dowex) and lyophilized once again. Finally, the residue is purified through a silica gel column (eluent: methylene chloride/methanol/water mixture) and lyophilized once again from water/dioxane. 12 mg of compound No. (1) (80%) result as a white powder.

$^1$H-NMR (CD$_3$OD-D$_2$O, 250.13 MHz) δ=1.08 (d, 6.8 Hz, 3 H); 1.18 (m, 8 H); 1.45 (m, 4 H); 1.78 (broad t, 11.0 Hz, 1H); 1.94 (s, 3 H); 2.23 (t, 7.6 Hz, 2 H); 2.71 (dd, 11.0 Hz, 3.4 Hz, 1 H); 3.71–4.06 (m, 28 H); 4.46 (d, 8.6 Hz, 2 H); 4.92 (d, 4.1 Hz, 1 H); 6.03 (s, 1 H). $^{13}$C-NMR (CD$_3$OD-D$_2$O, 126 MHz) δ=16.57; 22.57; 26.01; 27.26; 30.13; 30.36; 30.46; 30.63; 34.77; 42.30; 51.98; 53.96; 58.08; 61.16; 63.03; 64.64; 67.68; 68.85; 69.31; 69.96; 70.11; 70.78; 70.91; 71.01; 73.05; 73.71; 75.02; 75.28; 76.03; 76.74; 77.33; 77.99; 100.14; 100.90; 102.20; 103.90; 104.14; 174.94; 175.54; 176.14; remaining signals not resolved.

Example B1.2

Preparation of Compound No. (6)

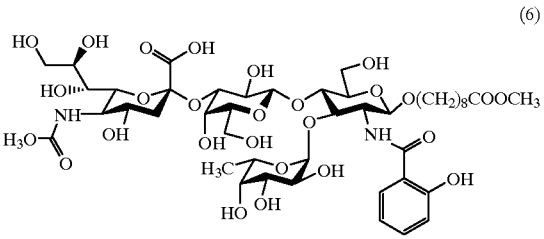

(6)

(a) 83 mg (238 μmol) of compound No. (2), 51.8 mg (261 μmol) of O-acetylsalicyloyl chloride and 39.7 ml of triethylamine are stirred, at RT and under an N$_2$ atmosphere, in 4 ml of dry methylene chloride. After the solvent has been evaporated off at 30° C., working-up takes place as described in Example B1.1(a). 92 mg (76%) of compound No. (7) are obtained. The phenolic acetate is eliminated during the subsequent galactosylation.

(7)

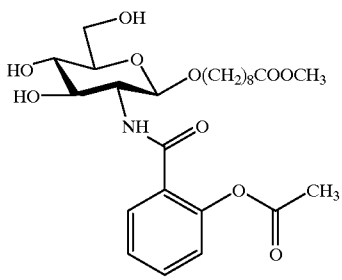

¹H-NMR (CD₃OD, 250.13 MHz) δ=1.20 (m, 8 H); 1.50 (m, 4 H); 2.25 (t, 7.5 Hz, 2 H); 2.28 (s, 3 H); 3.32–3.91 (m, 8 H); 3.61 (s, 3 H); 4.51 (d, 8.2 Hz, 1 H); 7.12 (d,d, 8.3 Hz, 1.4 Hz, 1 H); 7.29 (dt, 8.2 Hz, 1.2 Hz, 1 H); 7.48 (dt, 9.6 Hz, 1.3 Hz, 1 H); 7.60 (dd, 9.6 Hz, 1.4 Hz, 1 H). ¹³C-NMR (CD₃OD, 100.62 MHz) δ=25.98; 27.09; 30.03; 30.23; 30.25; 30.42; 30.56; 34.77; 51.95; 57.43; 62.84; 70.68; 72.30; 75.62; 77.97; 102.77; 116.88; 118.61; 119.83; 128.53; 134.87; 161.82; 171.82; 176.05.

(b) 54 mg (74%) of compound No. (8) are obtained from 60 mg (117 μmol) of compound No. (7) and 91 mg (147 μmol) of UDP-gal in accordance with Example B1.1 (b) (in this case, the buffer solution contains approximately 9% DMSO).

(8)

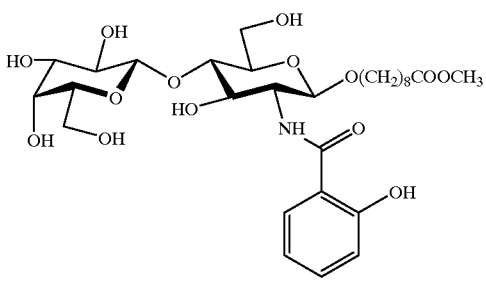

¹H-NMR (CD₃OD, 250.13 MHz) δ=0.99 (m, 8 H); 1.35 (m, 4 H); 2.19 (t, 7.5 Hz, 2 H); 3.27–3.92 (m, 14 H); 3.58 (s, 3 H); 4.29 (d, 8.6 Hz, 1 H); 4.48 (d, 9.0 Hz, 1H); 6.76 (broad d, approx. 9.0 Hz, 2 H); 7.25 (broad t, approx. 8.3 Hz, 1 H); 7.68 (broad d, approx. 9.5 Hz, 1 H). ¹³C-NMR (CD₃OD, 62.89 MHz) δ=25.84; 26.92; 29.82; 30.03 (2×C); 30.34; 34.78; 52.35; 56.55; 61.69; 62.40; 70.13; 71.05; 72.52; 73.69; 74.47; 76.38; 76.94; 80.73; 102.70; 104.75; 116.74; 118.50; 120.24; 128.71; 135.04; 161.15; 171.63; 176.86.

(c) 70 mg (91%) of compound No. (9) are obtained from 53 mg (84 μmol) of compound No. (8) and 75 mg (114 μmol) of CMP-sia in accordance with Example B1.1(c) (in this case, the buffer solution contains approximately 9% DMSO).

(9)

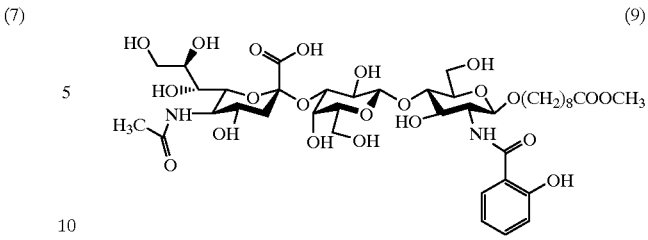

¹H-NMR (CD₃OD, 250.13 MHz) δ=1.02 (m, 8 H); 1.39 (m, 4 H); 1.71 (broad t, 11.0 Hz, 1 H); 1.96 (s, 3 H); 2.14 (t, 7.6 Hz, 2 H); 2.76 (broad d, 11.0 Hz, 1 H); 3.33–4.02 (m, 24 H); 4.40 (d, 8.6 Hz, 1 H); 4.49 (d, 8.6 Hz, 1 H); 6.80 (broad d, approx. 8.2 Hz, 2 H); 7.29 (broad d, approx. 8.3 Hz, 1 H); 7.72 (broad d, approx. 8.3 Hz, 1 H). ¹³C-NMR (CD₃OD-D₂O, 62.89 MHz) δ=22.63; 26.00; 27.10; 30.05; 30.16; 30.56; 34.78; 41.95; 51.96; 53.98; 56.57; 62.06; 62.77; 64.40; 69.30 (2×C); 70.02; 70.75; 70.91; 72.97; 73.93; 74.93; 76.58; 77.01; 77.66; 81.36; 101.20; 102.88; 105.01; 116.82; 118.67; 119.77; 128.43; 134.81; 161.98; 171.76; 175.14; 175.50.

(d) 73 mg (91%) of compound No. (6) are obtained from 69 mg (75 μmol) of compound No. (9) and 59 mg (93 μmol) of GDP-fuc in accordance with Example B1.1(d).

¹H-NMR (D₂O, 250.13 MHz) δ=0.94 (m, 8 H); 1.16 (d, 6.8 Hz, 3 H); 1.36 (m, 4 H); 1.80 (broad t, 12.0 Hz, 1 H); 2.03 (s, 3 H); 2.21 (t, 7.6 Hz, 2 H); 2.75 (dd, 12.0Hz, 4.2 Hz, 1 H); 3.48–4.24 (m, 27 H); 4.53 (d, 8.6 Hz, 1 H); 4.66 (d, 8.6 Hz, 1 H); 5.14 (d, 4.1 Hz, 1 H); 6.98 (broad t approx. 8.2 Hz, 2 H); 7.44 (broad t, approx. 8.2 Hz, 1 H); 7.73 (broad d, approx. 8.2 Hz, 1 H); remaining signals concealed by the solvent. ¹³C-NMR (D₂O, 125 MHz) δ=15.16; 21.93; 24.12; 25.13; 27.90; 28.10 (2×H); 28.51; 33.54; 39.69; 51.60; 51.93; 59.62; 61.40; 62.51; 66.57; 67.22; 67.52; 68.02; 68.21; 69.05; 69.20; 70.58; 71.76; 71.78; 72.82; 73.36; 74.82; 75.22; 75.56; 98.46; 99.57; 101.04; 101.52; 116.24; 117.66; 119.51; 128.18; 134.36; 170.33; 173.77; 174.92; 177.81; remaining signals not resolved.

Example B1.3

Preparation of Compound No. (10)

(10)

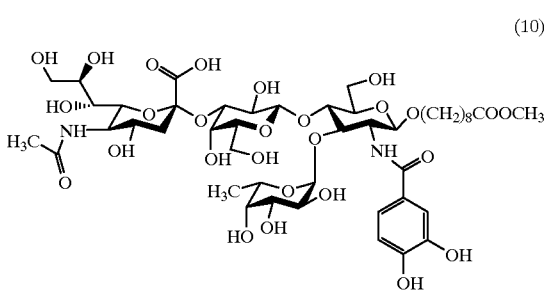

(a) 76 mg (58%) of compound No. (11) are obtained from 65 mg (252 μmol) of 3,4-di-O-acetylbenzoyl chloride and 80 mg (240 μmol) of compound No. (2) in accordance with Example B1.2(a).

(11)

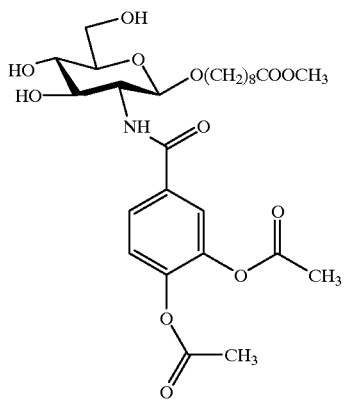

¹H-NMR (CD₃OD, 250.13 MHz) δ=1.08 (m, 8 H); 1.42 (m, 4 H); 2.16 (t, 7.6 Hz, 2 H); 2.21 (s, 6 H); 3.19–3.44 (m, 3 H); 3.57 (m, 4 H); 3.62 (dd, 13.7 Hz, 5.5 Hz, 1 H); 3.80 (m, 3 H); 4.46 (d, 8.2 Hz, 1 H); 7.24 (d, approx. 6.2 Hz, 1 H); 7.63 (d, approx. 2 Hz, 1 H); 7.70 (dd, 6.6 Hz, 2.0 Hz, 1 H); 7.60 (broad d, 9.6 Hz, 1 H). ¹³C-NMR (CD₃OD, 62.90 MHz) δ=20.43; 20.50; 25.95; 27.14; 30.06; 30.29 (2×C); 30.62; 34.77; 51.94; 58.03; 62.82; 70.65; 72.22; 75.67; 77.95; 102.74; 124.00; 124.70; 126.67; 134.50; 143.59; 146.26; 168.66; 169.43; 169.68; 176.04.

(b) 39 mg (64%) of compound No. (12) are obtained from 53 mg (93 μmol) of compound No. (11) and 67 mg (108 μmol) of UDP-gal in accordance with Example B1.1 (b) (in this case, the buffer solution contains approximately 8% DMSO).

(12)

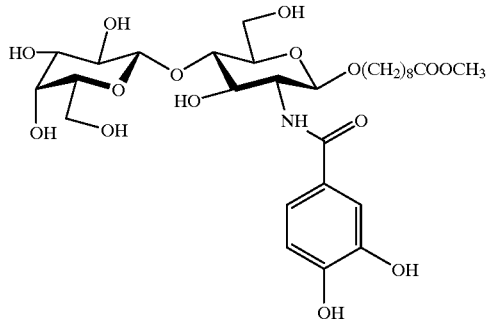

¹H-NMR (CD₃OD, 250.13 MHz) δ=1.13 (m, 8 H); 1.43 (m, 4 H); 2.19 (t, 7.5 Hz, 2 H); 3.35–3.94 (m, 17 H); 4.32 (d, 8.6 Hz, 1 H); 4.49 (d, 9.0 Hz, 1H); 6.71 (d, approx. 7.6 Hz, 1 H); 7.16 (dd, 7.6 Hz, 1.4 Hz, 1 H); 7.24 (d, 1.4 Hz, 1 H). ¹³C-NMR (CD₃OD, 62.89 MHz) δ=25.99; 27.13; 30.09; 30.33 (2×C); 30.65; 34.78; 51.96; 57.19; 61.60; 62.54; 70.34; 70.73; 72.62; 74.01; 74.83; 76.55; 77.14; 81.31; 102.92; 105.12; 115.66; 115.94; 120.61; 127.47; 146.25; 150.05; 170.47; 176.19.

(c) 49 mg (90%) of compound No. (13) are obtained from 38 mg (20 μmol) of compound No. (12) and 23 mg (34 μmol) of CMP-sia in accordance with Example B1.1(c) (in this case, the buffer solution contains 4% DMSO).

(13)

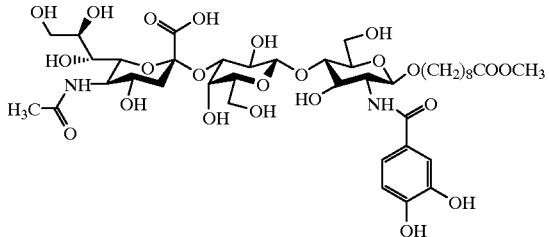

¹H-NMR (CD₃OD, 250.13 MHz) δ=1.02 (m, 8 H); 1.38 (m, 4 H); 1.61 (broad t, 11.0 Hz, 1 H); 1.89 (s, 3 H); 2.14 (t, 7.6 Hz, 2 H); 2.71 (broad d, 11.0 Hz, 1 H); 3.32–4.42 (m, 24 H); 4.41 (d, 8.6 Hz, 1 H); 4.46 (d, 8.6 Hz, 1 H); 6.71 (d, approx. 7.6 Hz, 1 H); 7.16 (dd, approx. 7.6 Hz, 1.4 Hz, 1 H); 7.24 (d, approx. 1.4 Hz, 1 H). ¹³C-NMR (CD₃OD, 62.89 MHz) δ=22.59; 26.00; 27.14; 30.11; 30.35 (2×C); 30.64; 34.79; 42.03; 51.97; 53.94; 57.03; 62.09; 62.77; 64.53; 69.05; 69.34; 70.05; 70.72; 70.91; 72.96; 74.04; 74.93; 76.55; 77.10; 77.66; 81.45; 101.09; 103.03; 104.99; 115.65; 115.97; 120.57; 127.53; 146.21; 149.97; 170.48; 175.51; 176.21.

(d) 22 mg (46%) of compound No. (10) are obtained from 41 mg (44 μmol) of compound No. (13) and 44 mg (69 μmol) of GDP-fuc in accordance with Example B1.1(d).

¹H-NMR (CD₃OD, 250.13 MHz) δ=1.08 (m, 8 H); 1.36 (d, 6.8 Hz, 3 H); 1.42 (m, 4 H); 1.65 (broad t, 11.0 Hz, 1 H); 2.16 (s, 3 H); 2.21 (t, 7.6 Hz, 2 H); 2.79 (broad d, 11.0 Hz, 1 H); 3.32–3.99 (m, 27 H); 4.45 (d, 8.6 Hz, 1 H); 4.50 (d, 8.6 Hz, 1 H); 4.98 (d, 4.2 Hz, 1 H); 6.70 (d, approx. 7.6 Hz, 1 H); 7.12 (dd, 7.6 Hz, 1.4 Hz, 1 H); 7.21 (d, 1.4 Hz, 1 H); remaining signals concealed by the solvent. ¹³C-NMR (CD₃OD, 100.61 MHz) δ=16.54; 22.62; 25.99; 27.17; 30.09; 30.31; 30.34; 30.66; 34.79; 42.24; 51.98; 53.97; 57.34; 60.86; 63.00; 64.16; 67.59; 69.26; 69.49; 69.83; 70.71; 70.92; 71.09; 73.04; 73.70; 74.97; 75.11; 75.34; 76.67; 77.25 (2×C); 77.94; 99.69; 100.88; 101.89; 103.89; 115.75; 116.07; 120.73; 126.49; 145.84; 149.44; 170.61; 173.89; 175.51; 176.21.

Example B1.4

Preparation of Compound No. (14)

(14)

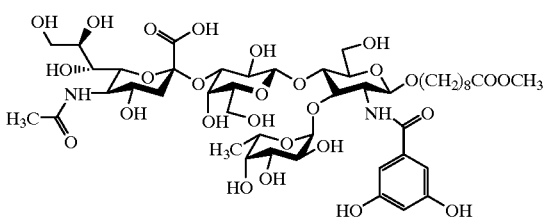

(a) 40 mg (26%) of compound No. (15) are obtained from 80 mg (314 μmol) of 3,5-di-O-acetylbenzoyl chloride and 100 mg (286 μmol) of compound No. (2) in accordance with Example B1.2(a).

(15)

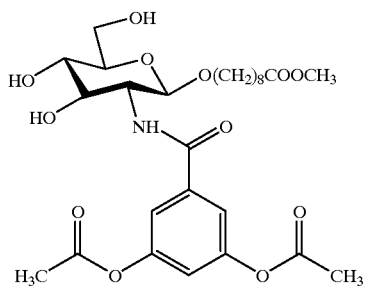

¹H-NMR (CD₃OD, 250.13 MHz) δ=1.10 (m, 8 H); 1.44 (m, 4 H); 2.18 (t, 7.6 Hz, 2 H); 2.22 (s, 6 H); 3.29 (m, 2 H); 3.40 (m, 1 H); 3.57 (m, 5 H); 3.81 (m, 3 H); 4.48 (d, 8.2 Hz, 1 H); 6.63 (t, approx. 2.0 Hz, 1 H); 6.98 (t, approx. 2.0 Hz, 1 H); 7.12 (t, 2.0 Hz, 1 H). ¹³C-NMR (CD₃OD, 62.90 MHz) δ=20.67 (2×C); 25.96; 27.14; 30.06; 30.26; 30.30; 30.64; 34.78; 51.94; 57.92; 62.82; 70.70; 72.31; 75.70; 77.92; 102.98; 112.64; 113.07; 113.19; 138.15; 153.04; 159.72; 168.66; 169.66; 170.92; 176.20.

(b) 27 mg (83%) of compound No. (16) are obtained from 29 mg (54 μmol) of compound No. (15) and 39 mg (63 μmol) of UDP-gal in accordance with Example B1.1(b) (in this case, the buffer solution contains approximately 8% DMSO).

(16)

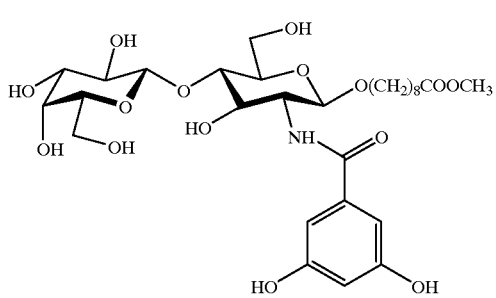

¹H-NMR (CD₃OD, 400.13 MHz) δ=1.19 (m, 6 H); 1.22 (m, 2 H); 1.42 (m, 4 H); 2.17 (t, 7.5 Hz, 2 H); 3.33–3.89 (m, 17 H); 4.33 (d, 8.6 Hz, 1 H); 4.49 (d, 9.0 Hz,1 H); 6.35 (t, approx. 2.0 Hz, 1 H); 6.66 (d, approx. 2.0 Hz, 2 H). ¹³C-NMR (CD₃OD, 100.61 MHz) δ=26.00; 27.16; 30.10; 30.30; 30.35; 30.67; 34.79; 51.96; 57.20; 60.06; 62.54; 70.34; 70.76; 72.63; 73.92; 74.84; 76.56; 77.15; 81.29; 102.83; 105.12; 106.43; 106.90 (2×C); 138.31; 159.73 (2×C); 170.84; 176.21.

(c) 27 mg (68%) of compound No. (17) are obtained from 27 mg (42 μmol) of compound No. (16) and 39 mg (59 μmol) of CMP-sia in accordance with Example B1.1(c).

(17)

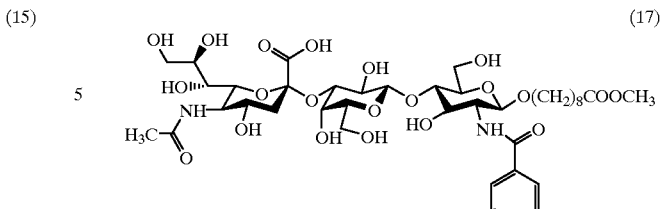

¹H-NMR (CD₃OD, 250.13 MHz) δ=1.08 (m, 8 H); 1.48 (m, 4 H); 1.63 (broad t, 11.0 Hz, 1 H); 1.90 (s, 3 H); 2.12 (t, 7.6 Hz, 2 H); 2.73 (dd, 11.0 HZ, 2.8 Hz, 1 H); 3.38–3.88 (m, 23 H); 3.95 (dd, 10.0 Hz, 3.4 Hz, 1 H); 4.35 (d, 8.6 Hz, 1 H); 4.41 (d, 8.6 Hz, 1 H); 6.29 (t, approx. 2.0 Hz, 1 H); 6.65 (d, approx. 2.0 Hz, 2 H). ¹³C-NMR (CD₃OD, 100.61 MHz) δ=22.65; 26.00; 27.15; 30.10; 30.30; 30.36; 30.66; 34.79; 41.58; 51.96; 53.94; 57.00; 62.05; 62.75; 64.42; 69.12; 69.29; 70.01; 70.79; 70.87; 72.96; 73.97; 74.90; 76.51; 77.12; 77.61; 81.37; 101.11; 102.91; 105.00; 106.46; 106.92 (2×C); 138.26; 159.74 (2×C); 170.87; 175.03; 175.50; 176.22.

(d) 14 mg (52%) of compound No. (14) are obtained from 23 mg (23 μmol) of compound No. (17) and 22 mg (34 μmol) of GDP-fuc in accordance with Example B1.1(d).

¹H-NMR (CD₃OD, 400.13 MHz) δ=1.11 (m, 11 H); 1.46 (m, 4 H); 1.79 (broad t, 11.0 Hz, 1 H); 1.96 (s, 3 H); 2.20 (t, 7.6 Hz, 2 H); 2.82 (broad d, 11.0 Hz, 1 H); 3.36–4.09 (m, 27 H); 4.49 (d, 8.6 Hz, 1 H); 4.55 (d, 8.6 Hz, 1 H); 5.03 (d, 5.0 Hz, 1 H); 6.36 (t, approx. 3.0 Hz, 1 H); 6.67 (d, approx. 3 Hz, 2 H); remaining signals concealed by the solvent. ¹³C-NMR (CD₃OD, 100.61 MHz) δ=16.54; 22.62; 26.00; 27.20; 30.10; 30.28; 30.37; 30.68; 34.80; 42.11; 51.97; 53.66; 61.61; 63.00; 64.39; 67.60; 68.59; 69.26; 69.41; 69.49; 70.75; 70.91; 70.95; 72.86; 73.71; 74.97; 75.02; 75.79; 76.66; 77.24; 77.74; 99.71; 100.88; 102.19; 103.89; 106.39; 106.94 (2×C); 138.01; 159.85 (2×C); 170.97; 174.34; 175.51; 176.23; remaining signals not resolved.

Example B1.5

Preparation of Compound No. (18)

(18)

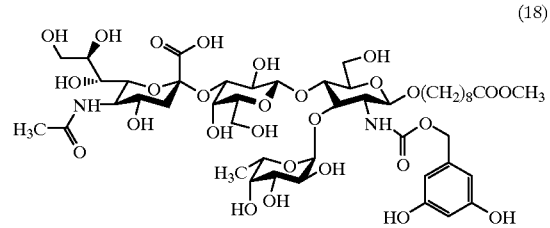

(a) 77 mg (36%) of compound No. (19) are obtained from 120 mg (418 μmol) of 3,5-di-O-acetylbenzyloxycarbonyl chloride and 131 mg (239 μmol) of compound No. (2) in accordance with Example B1.2(a).

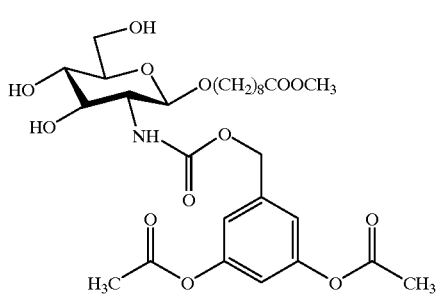

(19)

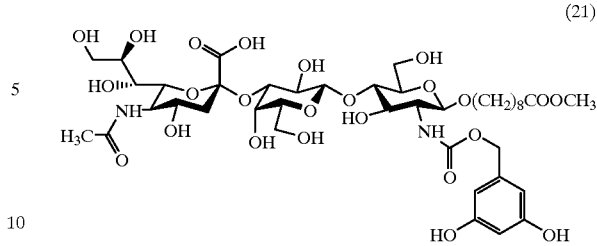

(21)

¹H-NMR (CD₃OD-CDCl₃-D₂O, 250.13 MHz) δ=1.11 (m, 8 H); 1.49 (m, 4 H); 2.20 (s, 6 H); 2.23 (t, 7.6 Hz, 2 H); 3.17–3.47 (m, 5 H); 3.55 (s, 3 H); 3.62 (dd, 12.4 Hz, 5.5 Hz, 1 H); 3.83 (m, 2 H); 4.81 (d, 8.2 Hz, 1 H); 4.95 (m, 2 H); 6.44 (t, approx. 2.0 Hz, 1 H); 6.54 (t, approx. 2.0 Hz, 1 H); 6.67 (t, 2.0 Hz, 1 H). ¹³C-NMR (CD₃OD-CDCl₃-D₂O, 62.89 MHz) δ=21.07 (2×C); 25.77; 26.73; 29.90; 30.03; 30.08; 30.34; 34.71; 52.03; 58.82; 62.54; 66.68; 70.72; 71.84; 75.56; 77.44; 102.86; 109.26 (2×C); 112.53; 112.88; 140.35; 152.78; 158.59; 159.95; 170.99; 176.11.

(b) 73 mg (78%) of compound No. (20) are obtained from 70 mg (137 μmol) of compound No. (19) and 116 mg (186 μmol) of UDP-gal in accordance with Example B1.1(b).

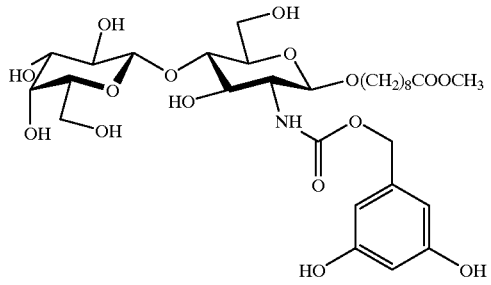

(20)

¹H-NMR (CD₃OD-CDCl₃-D₂O, 250.13 MHz) δ=1.30 (m, 8 H); 1.58 (m, 4 H); 2.30 (t, 7.5 Hz, 2 H); 3.38–3.93 (m, 17 H); 4.44 (broad d, 8.6 Hz, 2 H); 4.99 (t, 13.1 Hz, 2H); 6.28 (t, approx. 2.0 Hz, 1 H); 6.38 (d, approx. 2.0 Hz, 2 H). ¹³C-NMR (CD₃OD-CDCl₃-D₂O, 62.89 MHz) δ=25.53; 26.38; 29.65; 29.76; 29.80; 30.03; 34.68; 52.21; 57.92; 61.31; 62.00; 67.08; 69.65; 70.98; 72.00; 73.36; 73.94; 75.63; 76.56; 80.13; 102;45; 102.74; 104.17; 106.72 (2×C); 133.76; 158.52 (2×C); 176.26; remaining signals not resolved.

(c) 78 mg (77%) of compound No. (21) are obtained from 71 mg (105 μmol) of compound No. (20) and 95 mg (144 μmol) of CMP-sia in accordance with Example B1.1(c).

¹H-NMR (CD₃OD, 250.13 MHz) δ=1.12 (m, 8 H); 1.39 (m, 4 H); 1.62 (broad t, 11.6 Hz, 1 H); 1.88 (s, 3 H); 2.22 (t, 7.6 Hz, 2 H); 2.69 (dd, 11.6 Hz, 2.8 Hz, 1 H); 3.21–3.95 (m, 24 H); 4.21 (broad d, approx. 8.6 Hz, 1 H); 4.32 (broad d, approx. 8.6 Hz, 1 H); 6.03 (t, approx. 2.0 Hz, 1 H); 6.15 (d, approx. 2.0 Hz, 2 H); remaining signals concealed by the solvent. ¹³C-NMR (CD₃OD, 62.98 MHz) δ=22.78; 25.95; 26.92; 30.07; 30.22; 30.28; 30.52; 34.76; 41.70; 51.99; 53.93; 58.44; 61.95; 62.68; 64.22; 67.40; 69.20; 69.91; 70.78; 70.92; 72.95; 74.16; 74.83; 76.31; 76.78; 77.46; 81.15; 101.17; 102.99; 103.14; 104.93; 106.94 (2×C); 140.32; 158.96; 159.62 (2×C); 175.15; 175.49; 176.16.

(d) 72 mg (84%) of compound No. (18) are obtained from 74 mg (76 μmol) of compound No. (21) and 67 mg (106 μmol) of GDP-fuc in accordance with Example B1.1(d).

¹H-NMR (CD₃OD, 250.13 MHz) δ=1.06 (d, 6.8 Hz, 3 H); 1.19 (m, 8 H); 1.44 (m, 4 H); 1.65 (broad t, 11.0 Hz, 1 H); 1.92 (s, 3 H); 2.19 (t, 7.6 Hz, 2 H); 2.78 (broad d, 11.0 Hz, 1 H); 3.25–4.00 (m, 27 H); 4.30 (d, 8.6 Hz, 1 H); 4.43 (d, 8.6 Hz, 1 H); 5.08 (d, 4.3 Hz, 1 H); 6.09 (t, approx. 3.0 Hz, 1 H); 6.21 (d, approx. 3 Hz, 2 H); remaining signals concealed by the solvent. ¹³C-NMR (CD₃OD, 62.98 MHz) δ=16.58; 22.74; 25.95; 26.95; 30.09; 30.24; 30.29; 30.54; 34.78; 42.05; 52.00; 53.94; 59.27; 61.24; 63.02; 64.37; 67.56 (2×C); 68.92; 69.19; 70.00 (2×C); 70.88 (3×C); 73.05; 73.74; 74.87; 75.29; 76.14; 76.60; 77.16; 77.85; 99.88; 100.90; 102.81; 102.99; 103.85; 106.94 (2×C); 140.37; 158.95; 159.60 (2×C); 174.63; 175.50; 176.17.

Example B1.6

Preparation of Compound No. (22)

(22)

(a) 36 mg (214 μmol) of vanillic acid (Fluka) are added to 3 ml of dry DMF, and this mixture is treated, at RT, with 30 μl (216 μmol) of triethylamine and 91 mg (211 μmol) of TBTU (Fluka) [Dourtoglou, V., Gross, B., Lambropoulou, V., Zioudrou, C., Synthesis 572–574 (1984)]. 100 mg (286 μmol) of amine No. (2) are added to the resulting clear solution and the mixture is stirred overnight. After the solvent has been evaporated off, and following chromatography of the residue on RP-18 gel (eluent: methanol/water- 1/1), 41 mg (41%) of the compound No. (23) are obtained as a white powder after lyophilization from dioxane.

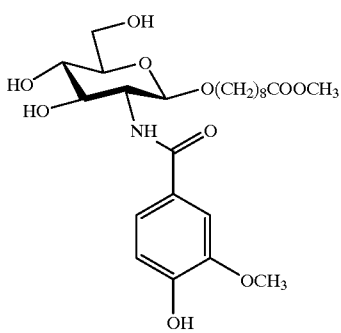
(23)

$^1$H-NMR (CD$_3$OD-CDCl$_3$, 250.13 MHz) δ=1.10 (m, 8 H); 1.46 (m, 4 H); 2.22 (t, 7.5 Hz, 2 H); 3.40–3.92 (m, 14 H); 4.59 (d, 8.2 Hz, 1 H); 6.82 (d, 8.3 Hz, 1 H); 7.36 (dd, 2.1 Hz, 8.3 Hz, 1H); 7.44 (d, 2.1 Hz, 1 H); $^{13}$C-NMR (CD$_3$OD-CDCl$_3$, 62.90 MHz) δ=25.78; 26.90; 29.90; 30.13 (2×C); 30.45; 34.76; 52.14; 56.46; 57.70; 62.90; 70.67; 72.11; 76.06; 77.32; 102.12; 111.96; 115.59; 121.88; 127.24; 150.14; 151.49; 167.68; 170.74.

(b) 27 mg (100%) of compound No. (24) are obtained from 21 mg (34 μmol) of compound No. (23) and 32 mg (52 μmol) of UDP-gal in accordance with Example B1.1(b) (in this case, the buffer solution contains approximately 12% DMSO).

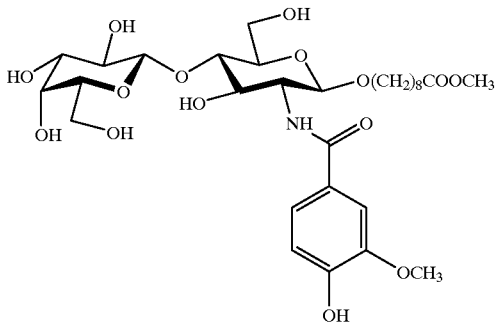
(24)

$^1$H-NMR (CD$_3$OD-CDCl$_3$, 250.13 MHz) δ=1.05 (m, 8 H); 1.40 (m, 4 H); 2.17 (t, 7.5 Hz, 2 H); 3.35–3.92 (m, 20 H); 4.35 (d, 8.3 Hz, 1 H); 4.57 (d, 8.2 Hz, 1 H); 6.79 (d, 8.3 Hz, 1 H); 7.31 (dd, 2.1 Hz, 8.3 Hz, 1 H); 7.39 (d, 2.1 Hz, 1 H); $^{13}$C-NMR (CD$_3$OD-CDCl$_3$, 100.61 MHz) δ=25.60; 26.63; 29.71; 29.89 (2×C); 29.95; 34.72; 52.32; 56.46 (2×C); 61.23; 61.82; 69.55; 70.68; 71.95; 73.00; 73.83; 75.71; 76.38; 80.05; 102.70; 104.13; 111.48; 114.93; 121.38; 126.40; 146.93; 150.11; 168.85; 175.98; remaining signals not resolved.

(c) 32 mg (86%) of compound No. (25) are obtained from 26 mg (39 μmol) of compound No. (24) and 39 mg (59 μmol) of CMP-sia in accordance with Example B1.1(c) (in this case, the buffer solution contains 9% DMSO).

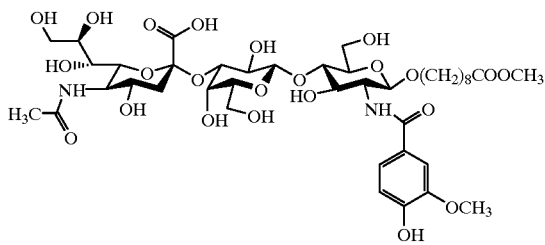
(25)

$^1$H-NMR (CD$_3$OD, 250.13 MHz) δ=1.02 (m, 8 H); 1.48 (m, 4 H); 1.68 (broad t, 11.6 Hz, 1 H); 1.94 (s, 3 H); 2.14 (t, 7.6 Hz, 2 H); 2.76 (dd, 11.6 Hz, 2.8 Hz, 1 H); 3.32–4.01 (m, 27 H); 4.38 (d, 8.6 Hz, 1 H); 4.48 (d, 8.6 Hz, 1 H); 6.73 (d, 8.3 Hz, 1 H); 7.30 (dd, 2.1 Hz, 8.3 Hz, 1H); 7.39 (d, 2.1 Hz, 1 H); $^{13}$C-NMR (CD$_3$OD-CDCl$_3$, 62.90 MHz) δ=22.70; 25.91; 27.07; 30.01; 30.27 (2×C); 30.58; 34.72; 42.06; 51.90; 53.89; 56.44; 57.03; 62.03; 62.66; 64.05; 69.15 (2×C); 69.92; 72.91; 74.03; 74.84; 76.42; 76.89; 77.50; 78.67; 79.20; 79.72; 81.77; 101.05; 102.90; 104.97; 112.11; 115.72; 122.10; 127.03; 148.66; 151.18; 170.12; 175.04; 175.45; 176.05.

(d) 25 mg (73%) of compound No. (22) are obtained from 30 mg (32 μmol) of compound No. (25) and 25 mg (40 μmol) of GDP-fuc in accordance with Example B1.1 (d).

$^1$H-NMR (CD$_3$OD, 250.13 MHz) δ=1.02 (m, 8 H); 1.09 (d, 6.8 Hz, 3 H); 1.39 (m, 4 H); 1.64 (broad t, 11.0 Hz, 1 H); 1.94 (s, 3 H); 2.13 (t, 7.6 Hz, 2 H); 2.69 (dd, 11.6 Hz, 2.8 Hz, 1 H); 3.32–4.05 (m, 30 H); 4.46 (d, 8.6 Hz, 1 H); 4.52 (broad d, 8.6 Hz, 1 H); 4.75 (q, 6.8 Hz, 1 H); 4.98 (d, 4.3 Hz, 1 H); 6.53 (d, 8.3 Hz, 1 H); 7.29 (dd, 2.1 Hz, 8.3 Hz, 1H); 7.38 (d, 2.1 Hz, 1 H); $^{13}$C-NMR (CD$_3$OD-CDCl$_3$, 62.90 MHz) δ=16.55; 22.61; 25.96; 27.19; 30.07; 30.34 (2×C); 30.65; 34.74; 42.24; 51.97; 53.95; 56.46; 58.05; 61.27; 62.97; 64.56; 67.60; 68.79; 69.26; 69.85; 70.06; 70.70; 70.92; 71.07; 73.04; 73.69; 74.97; 75.43; 75.94; 76.69; 77.25; 77.94; 99.73; 100.87; 103.88; 112.23; 115.82; 122.17; 126.92; 148.80; 151.42; 170.29; 174.94; 175.50; 176.08; remaining signals not resolved.

Example B1.7

Preparation of Compound No. (26)

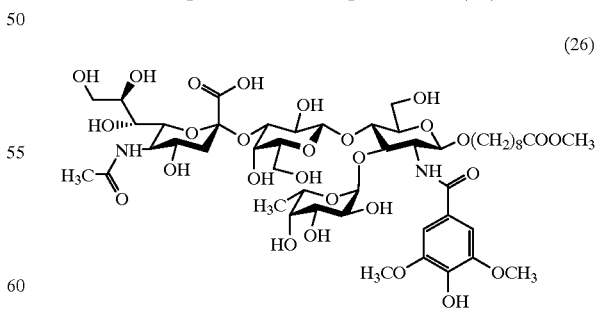
(26)

(a) 76 mg (69%) of monosaccharide No. (27) are obtained from 42 mg (214 μmol) of syringic acid (Fluka) and 100 mg (286 μmol) of amine No. (2) in accordance with Example B1.6(a).

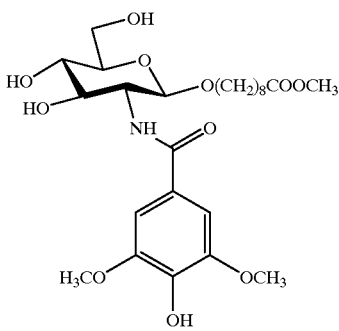

(27)

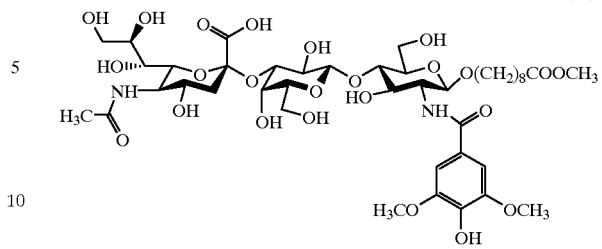

(29)

$^1$H-NMR (CD$_3$OD, 250.13 MHz) δ=1.02 (m, 8 H); 1.38 (m, 4 H); 2.13 (t, 7.5 Hz, 2 H); 3.38 (m, 3 H); 3.53 (s, 3 H); 3.62 (m, 2 H); 3.80 (m, 9 H); 4.51 (d$_1$ 8.2 Hz, 1 H); 7.13 (s, 1 H); $^{13}$C-NMR (CD$_3$OD, 62.90 MHz) δ=25.92; 27.16; 30.05; 30.35 (2×C); 30.65; 51.93; 56.81 (2×C); 57.97; 62.85; 70.60; 72.34; 75.76; 77.93; 102.83; 106.20 (2×C); 125.79; 140.41; 148.87 (2×C); 170.17; 176.01.

(b) 34 mg (89%) of compound No. (28) are obtained from 29 mg (55 μmol) of compound No. (27) and 45 mg (74 μmol) of UDP-gal in accordance with Example B1.1(b) (in this case, the buffer solution contains approximately 12% DMSO).

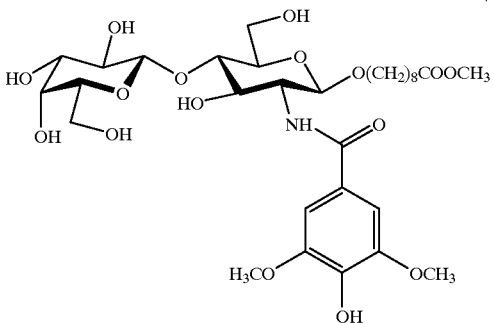

(28)

$^1$H-NMR (CD$_3$OD, 400.13 MHz) δ=1.09 (m, 8 H); 1.45 (m, 4 H); 2.21 (t, 7.5 Hz, 2 H); 3.40 (m, 4 H); 3.67–376 (m, 7 H); 3.86 (m, 12 H); 4.40 (d, 8.6 Hz, 1 H); 4.59 (d, 8.6 Hz, 1 H); 7.18 (s, 2 H). $^{13}$C-NMR (CD$_3$OD-CDCl$_3$, 62.90 MHz) δ=25.19; 25.87; 29.37; 29.50; 29.56; 29.80; 34.39; 51.95; 56.61 (3×C); 61.10; 61.65; 69.26; 70.59; 71.63; 72.69; 73.56; 75.29; 75.97; 80.00; 101.69; 103.78; 105.35 (2×C); 124.97; 139.13; 137.74 (2×C); 169.26; 175.61.

(c) 28 mg (61%) of compound No. (29) are obtained from 33 mg (48 μmol) of compound No. (28) and 48 mg (73 μmol) of CMP-sia in accordance with Example B1.1(c) (in this case, the buffer solution contains 5% DMSO).

$^1$H-NMR (CD$_3$OD, 250.13 MHz) δ=1.09 (m, 8 H); 1.40 (m, 4 H); 1.66 (broad t, 11.6 Hz, 1 H); 1.94 (s, 3 H); 2.14 (t, 7.6 Hz, 2 H); 2.78 (dd, 11.6 Hz, 2.8 Hz, 1 H); 3.32–4.01 (m, 30 H); 4.38 (d, 8.6 Hz, 1 H); 4.49 (d, 8.6 Hz, 1 H); 7.14 (s, 2 H). $^{13}$C-NMR (CD$_3$OD-CDCl$_3$, 100.61 MHz) δ=25.95; 27.18; 30.08; 30.39 (2×C); 30.64; 34.71; 41.88; 51.97; 54.50; 56.83 (2×C); 57.16; 61.60; 62.35; 64.00; 68.72; 69.10; 69.92; 70.74; 70.79; 72.77; 73.98; 74.90; 76.53; 76.67; 77.35; 80.95; 100.67; 102.96; 104.87; 106.14 (2×C); 120.98; 125.93;, 140.14; 148.84 (2×C); 170.01; 174.92; 176.08 (2×C).

(d) 11 mg (36%) of compound No. (26) are obtained from 27 mg (28 μmol) of compound No. (29) and 26 mg (41 μmol) of GDP-fuc in accordance with Example B1.1(d).

$^1$H-NMR (CD$_3$OD, 250.13 MHz) δ=1.02 (m, 8 H); 1.08 (d, 6.8 Hz, 3 H); 1.39 (m, 4 H); 1.65 (broad t, 11.0 Hz, 1 H); 1.95 (s, 3 H); 2.14 (t, 7.6 Hz, 2 H); 2.79 (dd, 11.6 Hz, 2.8 Hz,$_1$ 1 H); 3.32–4.04 (m, 33 H); 4.45 (d, 8.6 Hz, 1 H); 4.56 (broad d, 8.6 Hz, I H); 4.80 (q, 6.8 Hz, 1 H); 4.99 (d, 4.3 Hz, 1 H); 7.12 (s, 2 H). $^{13}$C-NMR (CD$_3$OD-CDCl$_3$, 62.90 MHz) δ=16.48; 22.77; 25.74; 26.97; 29.79; 30.08 (2×C); 30.35; 34.70; 41.81; 52.44; 53.60; 56.99 (2×C); 61.44; 62.72; 64.20; 67.79; 68.94; 69.16; 69.57; 69.77; 70.72; 70.88; 71.08; 72.97; 73.41; 74.64; 75.09; 76.18; 76.37; 76.90; 77.53; 99.69; 100.78; 103.40; 106.06 (3×C); 120.56; 125.29; 140.42; 148.56 (2×C); 170.21; 174.83; 175.96; 176.37.

Example B1.8

Preparation of Compound No. (30)

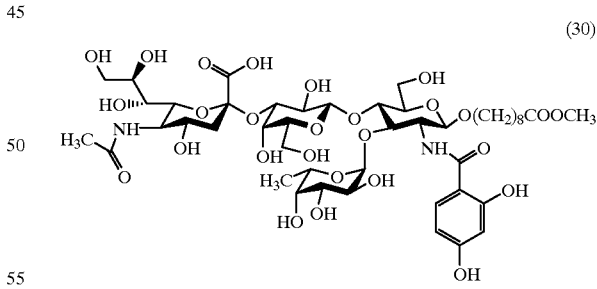

(30)

(a) 50 mg (210 μmol) of 2,4-di-O-acetylbenzoic acid are reacted with 100 mg (210 μmol) of amine No. (32) in accordance with Example B1.6(a). After chromatography on silica gel (petroleum ether/ethyl acetate-1/3), 79 mg (54%) are obtained of per-O-acetylated amide, which is deprotected, using a catalytic quantity of an 0.1 M solution of sodium methoxide in methanol, to give compound No. (33). Following chromatographic purification on silica gel (eluent: methylene chloride/methanol-10/1), 28 mg (54%) of monosaccharide are obtained.

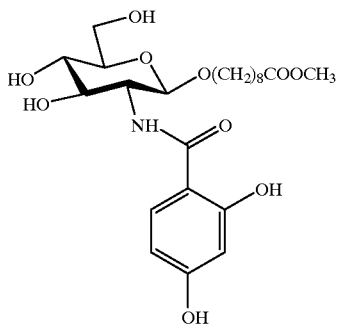

(33)

Alternatively, compound No. (33) can also be obtained, in accordance with Example B1.6 (a), from amine No. (2) in place of No. (32) as indicated above.

$^1$H-NMR (CD$_3$OD, 250.13 MHz) δ=1.02 (m, 8 H); 1.40 (m, 4 H); 2.18 (t, 7.6 Hz, 2 H); 3.26 (m, 2 H); 3.38 (m, 1 H); 3.56 (m, 4 H); 3.62 (dd, 5.5 Hz, 9.6 Hz); 3.80 (m, 3 H); 4.48 (d, 7.6 Hz, 1 H); 6.19 (d, 1.4 Hz, 1 H); 6.24 (dd, 1.4 Hz, 8.3 Hz, 1 H); 7.55 (d, 8.3 Hz, 1 H). $^{13}$C-NMR (CDCl$_3$, 62.90 MHz) δ=25.57; 26.68; 29.65; 29.87 (2×C); 30.15; 34.39; 51.59; 56.77; 62.41; 70.30; 71.87; 75.27; 77.63; 102.42; 103.55; 107.84; 108.25; 129.47; 163.36; 163.55; 171.62; 175.78.

(b) 29 mg (92%) of compound No. (34) are obtained from 24 mg (50 μmol) of compound No. (33) and 38 mg (63 μmol) of UDP-gal in accordance with Example B1.1(b) (in this case, the buffer solution contains approximately 8% DMSO).

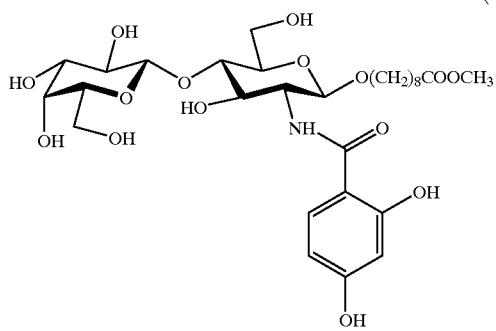

(34)

$^1$H-NMR (CD$_3$OD, 250.13 MHz) δ=1.19 (m, 8 H); 1.57 (m, 4 H); 2.32 (t, 7.5 Hz, 2 H); 3.46–4.01 (m, 17 H); 4.48 (d, 8.6 Hz, 1 H); 4.66 (d, 8.6 Hz, 1 H); 6.38 (d, 1.4 Hz, 1 H); 6.43 (dd, 1.4 Hz, 8.3 Hz, 1 H); 7.68 (d, 8.3 Hz, 1 H). $^{13}$C-NMR (CD$_3$OD, 62.90 MHz) δ=25.71; 26.79; 29.69; 29.93 (2×C); 30.16; 34.72; 52.54; 56.21; 61.47; 62.25; 69.94; 71.19; 72.35; 73.53; 74.16; 76.16; 76.72; 80.35; 102.67; 103.95; 104.45; 108.46; 108.58; 130.27; 163.14; 163.17; 171.71; 177.39.

(c) 23 mg (57%) of compound No. (35) are obtained from 28 mg (44 μmol) of compound No. (34) and 40 mg (60 μmol) of CMP-sia in accordance with Example B1.1 (c) (in this case, the buffer solution contains 9% DMSO).

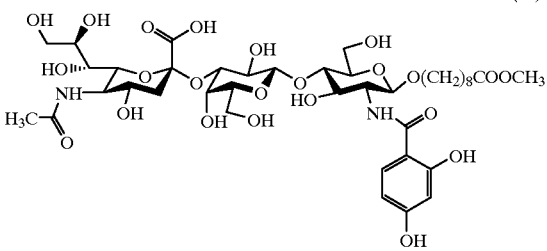

(35)

$^1$H-NMR (CD$_3$OD, 250.13 MHz) δ=1.02 (m, 8 H); 1.49 (m, 4 H); 1.66 (broad t, 11.6 Hz, 1 H); 1.94 (s, 3 H); 2.18 (t, 7.6 Hz, 2 H); 2.78 (dd, 11.6 Hz, 2.8 Hz, 1 H); 3.32–3.92 (m, 23 H); 4.08 (dd, 2.8 Hz, 9.6 Hz, 1 H); 4.39 (d, 8.6 Hz, 1 H); 4.46 (d, 8.6 Hz, 1 H); 6.18 (d, 1.4 Hz, 1 H); 6.22 (dd, 1.4 Hz, 8.3 Hz, 1 H); 7.53 (d, 8.3 Hz, 1 H). $^{13}$C-NMR (CD$_3$OD, 62.90 MHz) δ=22.60; 26.02, 27.11; 30.09; 30.32 (2×C); 30.57; 34.80; 42.02; 51.96; 53.94; 56.37; 62.06; 62.78; 64.50; 69.08; 69.32; 70.05; 70.76; 70.89; 72.96; 74.01; 74.93; 76.54; 77.10; 77.64; 81.36; 101.09; 102.98; 104.06; 104.99; 108.19; 108.65; 129.81; 163.94; 164.28; 172.01; 174.97; 175.50; 176.18.

(d) 16 mg (63%) of compound No. (30) are obtained from 23 mg (23 μmol) of compound No. (35) and 20 mg (31 μmol) of GDP-fuc in accordance with Example B1.1(d).

$^1$H-NMR (CD$_3$OD, 250.13 MHz) δ=1.01 (m, 8 H); 1.09 (d, 6.8 Hz, 3 H); 1.49 (m, 4 H); 1.63 (broad t, 11.0 Hz, 1 H); 1.93 (s, 3 H); 2.18 (t, 7.6 Hz, 2 H); 2.79 (dd, 11.6 Hz, 2.8 Hz, 1 H); 3.31–4.08 (m, 27 H); 4.45 (d, 8.6 Hz, 1 H); 4.51 (broad d, 8.6 Hz, 1 H); 4.75 (q, 6.8 Hz, 1 H); 5.01 (d, 4.3 Hz, 1 H); 6.18 (d, 1.4 Hz, 1 H); 6.23 (dd, 1.4 Hz, 8.3 Hz, 1 H); 7.51 (d, 8.3 Hz, 1 H). $^{13}$C-NMR (CD$_3$OD, 62.90 MHz) δ=16.52; 21.13; 22.57; 26.01; 27.15; 30.10; 30.31 (2×C); 30.59; 34.80; 42.30; 51.96; 53.94; 57.30; 61.29; 63.00; 64.62; 67.59; 68.81; 69.28; 70.09; 70.74; 70.93; 71.04; 73.04; 73.69; 75.00; 75.42; 75.78; 76.77; 77.24; 77.95; 99.69; 100.86; 102.61; 103.88; 104.13; 108.34; 108.68; 129.93; 164.13; 164.30; 171.94; 174.88; 175.50; 176.17.

Example B1.9

Preparation of Compound No. (36)

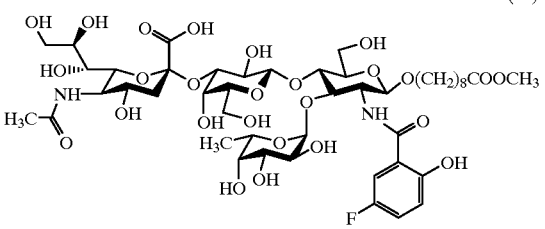

(36)

(a) 47 mg (48%) of monosaccharide No. (37), which is still contaminated with a little triethylamine, is obtained from 33 mg (212 μmol) of 3-fluoro-6-hydroxybenzoic acid (Fluka) and 100 mg (286 μmol) of amine No. (2) in accordance with Example B1.6(a).

(37)

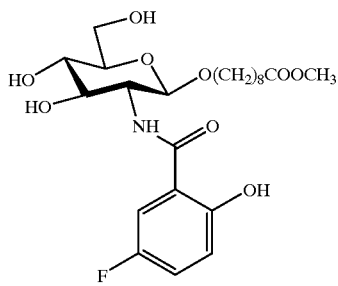

¹H-NMR (CD₃OD-CDCl₃, 250.13 MHz) δ=1.09 (m, 8 H); 1.45 (m, 4 H); 2.21 (t, 7.6 Hz, 2 H); 3.33–3.89 (m, 11 H); 4.54 (d, 7.6 Hz, 1 H); 6.84 (dd, 5.5 Hz, 10.3 Hz, 1 H); 7.02 (ddd, 3.4 Hz, 7.6 Hz, 8.3 Hz, 1 H); 7.42 (dd, 5.5 Hz, 10.3 Hz, 1 H). ¹³C-NMR (CD₃OD-CDCl₃, 62.90 MHz) δ=24.61; 25.57; 28.72; 28.82; 28.85; 29.15; 33.84; 51.37; 55.84; 61.26; 70.07; 70.58; 74.03; 75.27; 100.94; 112.97 (d, 24.2 Hz); 115.24 (d, 6.5 Hz); 118.69; 120.90 (d, 23.4 Hz); 155.11 (d, 174.2 Hz); 157.02; 169.40; 174.80. ¹⁹F-NMR (CD₃OD-CDCl₃, 235.36 MHz) δ=−73.36.

(b) 13 mg (41%) of compound No. (38) are obtained from 22 mg (46 μmol) of compound No. (37) and 36 mg (59 μmol) of UDP-gal in accordance with Example B1.1(b) (in this case, the buffer solution contains approximately 9% DMSO).

(38)

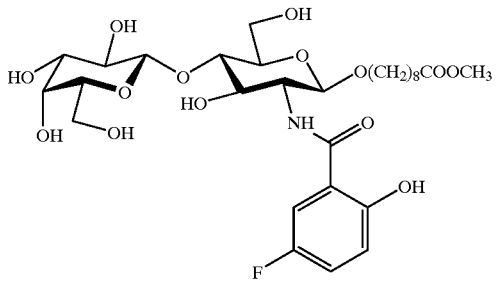

¹H-NMR (CD₃OD, 250.13 MHz) δ=1.15 (m, 8 H); 1.51 (m, 4 H); 2.27 (t, 7.5 Hz, 2 H); 3.41–4.02 (m, 17 H); 4.43 (d, 8.6 Hz, 1 H); 4.62 (d, 8.6 Hz, 1 H); 6.92 (dd, 5.5 Hz, 10.3 Hz, 1 H); 7.16 (ddd, 3.4 Hz, 7.6 Hz, 8.3 Hz, 1 H); 7.59 (dd, 5.5 Hz, 10.3 Hz, 1 H). ¹³C-NMR (CD₃OD, 62.90 MHz) δ=25.45; 26.46; 29.54; 29.67; 29.71; 29.98; 34.59; 52.06; 56.19; 61.42; 61.96; 69.59; 70.72; 71.98; 73.05; 74.00; 75.69; 76.35; 80.47; 102.00; 104.23; 113.94 (d, 24.7 Hz); 117.11 (d, 6.5 Hz); 119.38 (d, 7.4 Hz); 121.38 (d, 23.3 Hz); 156.97 (d, 174.2 Hz); 158.63; 170.20;. 175.96.

(c) 11 mg (65%) of compound No. (39) are obtained from 12 mg (18 μmol) of compound No. (38) and 22 mg (33 μmol) of CMP-sia in accordance with Example B1.1(c) (in this case, the buffer solution contains 8% DMSO).

(39)

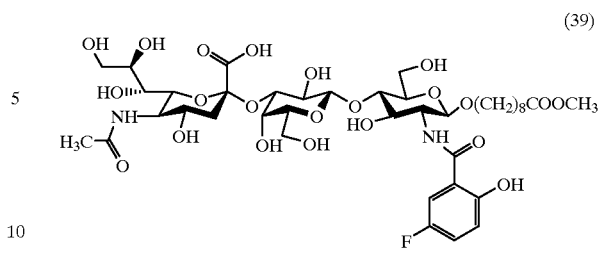

¹H-NMR (CD₃OD, 400.13 MHz) δ=1.00 (m, 8 H); 1.32 (m, 4 H); 1.62 (broad t, 11.6 Hz, 1 H); 1.89 (s, 3 H); 2.09 (t, 7.6 Hz, 2 H); 2.71 (dd, 11.6 Hz, 2.8 Hz, 1 H); 3.29–3.95 (m, 24 H); 4.35 (d, 8.6 Hz, 1 H); 4.42 (d, 8.6 Hz, 1 H); 6.76 (dd, 5.5 Hz, 10.3 Hz, 1 H); 7.03 (ddd, 3.4 Hz, 7.6 Hz, 8.3 Hz, 1 H); 7.45 (dd, 5.5 Hz, 10.3 Hz, 1 H). ¹³C-NMR (CD₃OD, 62.90 MHz) δ=22.63; 26.00; 27.13; 30.07; 30.31 (2×C); 30.55; 34.77; 42.15; 51.96; 53.98; 56.68; 62.35; 62.77; 64.36; 69.28 (2×C); 70.01; 70.76; 70.88; 72.98; 73.93; 74.93; 76.57; 76.98; 77.64; 81.23; 101.21; 102.81; 104.99; 113.96 (d, 24.7 Hz); 119.87 (d, 7.4 Hz); 121.56 (d, 23.3 Hz); 156.55 (d, 174.2 Hz); 175.18; 175.51; remaining signals not resolved.

(d) 9 mg (67%) of compound No. (36) are obtained from 11 mg (12 μmol) of compound No. (39) and 12 mg (18 μmol) of GDP-fuc in accordance with Example B1.1(d).

¹H-NMR (CD₃OD, 250.13 MHz) δ=1.08 (m, 11 H); 1.39 (m, 4 H); 1.66 (broad t, 11.0 Hz, 1 H); 1.93 (s, 3 H); 2.18 (t, 7.6 Hz, 2 H); 2.80 (dd, 11.6 Hz, 2.8 Hz, 1 H); 3.29–4.16 (m, 27 H); 4.46 (d, 8.6 Hz, 1 H); 4.52 (broad d, 8.6 Hz, 1 H); 4.75 (broad q, 6.8 Hz, 1 H); 4.99 (d, 4.3 Hz, 1 H); 6.81 (dd, 5.5 Hz, 10.3 Hz, 1 H); 7.09 (ddd, 3.4 Hz, 7.6 Hz, 8.3 Hz, 1 H); 7.46 (dd, 5.5 Hz, 10.3 Hz, 1 H). ¹³C-NMR (CD₃OD, 62.90 MHz) δ=16.27; 21.14; 26.00; 27.14; 30.09; 30.28 (2×C); 30.57; 34.77; 42.32; 51.96; 53.96; 57.78; 61.25; 63.34; 65.03; 67.63; 68.81; 69.59; 69.84; 70.73; 70.92; 71.28; 73.36; 73.69; 75.02; 75.34; 75.81; 77.07; 77.29; 78.42; 99.88; 101.59; 102.49; 103.86; 114.76 (d, 24.7 Hz); 117.79 (d, 7.4 Hz); 122.24 (d, 23.3 Hz); 157.69 (d, 174.2 Hz); 176.04; remaining signals not resolved.

Example B1.10

Preparation of Compound No. (40)

(40)

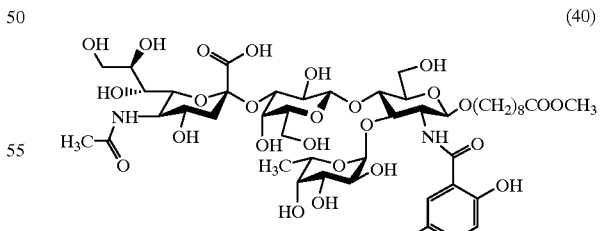

(a) 59 mg (60%) of monosaccharide No. (41) are obtained, in accordance with Example B1.8(a), from 31 mg (204 μmol) of 2-hydroxy-5-methylbenzoic acid (Fluka) and 100 mg (210 μmol) of amine No. (32) in the presence of 95 mg of HBPyU (Fluka) in place of TBTU in 3 ml of dry acetonitrile.

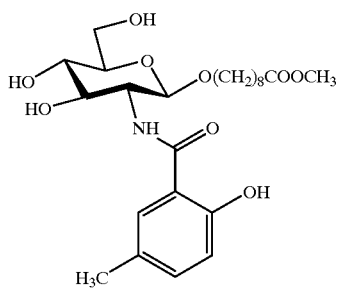

(41)

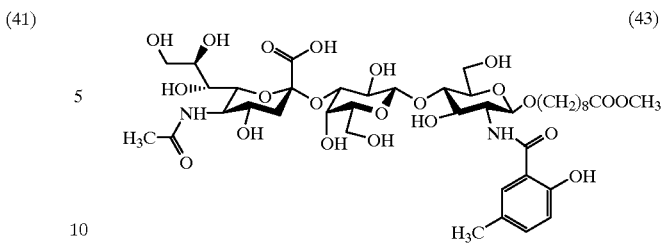

(43)

$^1$H-NMR (CD$_3$OD, 250.13 MHz) δ=1.02 (m, 8 H); 1.38 (m, 4 H); 1.66 (broad t, 11.6 Hz, 1 H); 1.94 (s, 3 H); 2.14 (t, 7.6 Hz, 2 H); 2.19 (s, 3 H); 2.78 (dd, 11.6 Hz, 2.8 Hz, 1 H); 3.32–4.01 (m, 24 H); 4.41 (d, 8.6 Hz, 1 H); 4.49 (d, 8.6 Hz, 1 H); 6.66 (d, 7.6 Hz, 1 H); 7.06 (dd, 1.4 Hz, 7.6 Hz, 1 H); 7.53 (d, 1.4 Hz, 1 H). $^{13}$C-NMR (CD$_3$OD, 62.90 MHz) δ=20.61; 22.58; 26.01; 27.11; 30.08; 30.26; 30.31; 30.59; 34.79; 42.10; 51.95; 53.93; 56.61; 62.01; 62.79; 64.54; 69.05; 69.34; 70.07; 70.84; 72.97; 74.23; 74.93 (2×C); 76.54; 77.12; 77.63; 81.11; 101.06; 103.09; 104.96; 117.07; 119.46; 127.56; 128.84; 135.34; 162.28; 171.99; 174.91; 175.49; 176.05.

$^1$H-NMR (CD$_3$OD, 250.13 MHz) δ=1.03 (m, 8 H); 1.39 (m, 4 H); 2.15 (t, 7.6 Hz, 2 H); 2.21 (s, 3 H); 3.23–3.44 (m, 3 H); 3.57 (s, 3 H); 3.62 (m, 2 H); 3.81 (m, 3 H); 4.50 (d, 7.6 Hz, 1 H); 6.71 (d, 7.6 Hz, 1 H); 7.10 (dd, 1.4 Hz, 7.6 Hz, 1 H); 7.53 (d, 1.4 Hz, 1 H). $^{13}$C-NMR (CD$_3$OD, 62.90 MHz) δ=20.62; 25.79; 26.90; 29.86; 30.03; 30.09; 30.38; 34.68; 51.94; 57.15; 62.64; 70.60; 72.07; 75.42; 77.60; 102.54; 116.22; 118.21; 128.34; 128.91; 135.41; 159.18; 171.62; 175.91.

(d) 15 mg (100%) of compound No. (40) are obtained from 12 mg (13 μmol) of compound No. (43) and 12 mg (19 μmol) of GDP-fuc in accordance with Example B1.1(d).

(b) 19 mg (95%) of compound No. (42) are obtained from 15 mg (31 μmol) of compound No. (41) and 25 mg (40 μmol) of UDP-gal in accordance with Example B1.1(b) (in this case, the buffer solution contains approximately 11% DMSO).

$^1$H-NMR (CD$_3$OD, 250.13 MHz) δ=1.01 (m, 11 H); 1.38 (m, 4 H); 1.63 (broad t, 11.0 Hz, 1 H); 1.92 (s, 3 H); 2.13 (t, 7.6 Hz, 2 H); 2.19 (s, 3 H); 2.79 (dd, 11.6 Hz, 2.8 Hz, 1 H); 3.31–4.14 (m, 27 H); 4.44 (d, 8.6 Hz, 1 H); 4.52 (broad d, 8.6 Hz, 1 H); 4.71 (broad q, 6.8 Hz, 1 H); 4.99 (d, 4.3 Hz, 1 H); 6.77 (d, 7.6 Hz, 1 H); 7.09 (dd, 1.4 Hz, 7.6 Hz, 1 H); 7.49 (d, 1.4 Hz, 1 H). $^{13}$C-NMR (CD$_3$OD, 62.90 MHz) δ=16.51; 20.60; 22.62; 25.99; 27.14; 30.05; 30.21; 30.28; 30.59; 34.78; 42.27; 51.96; 53.96; 57.64; 61.30; 63.01; 64.49; 67.62; 68.80; 69.25; 69.65; 70.07 (2×C); 70.84; 70.98; 73.05; 73.66; 74.96; 75.48; 75.82; 76.96; 77.23; 77.86; 99.66; 100.89; 102.56; 103.95; 116.59; 118.97; 128.76; 129.19; 135.65; 161.48; 171.83; 174.94; 175:48; 176.04.

Example B1.11

Preparation of Compound No. (44)

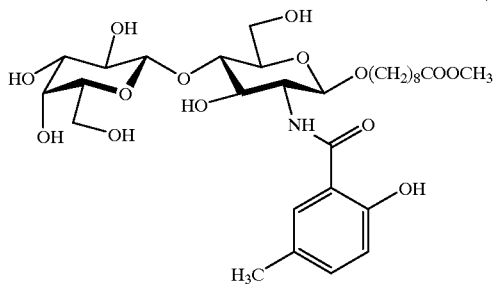

(42)

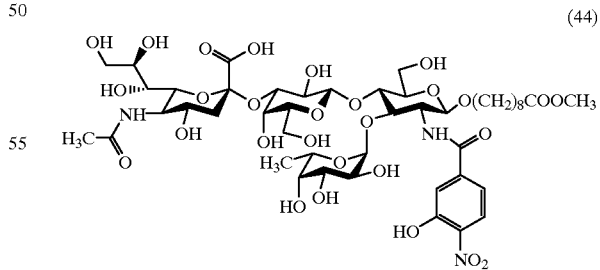

(44)

$^1$H-NMR (CD$_3$OD, 250.13 MHz) δ=1.01 (m, 8 H); 1.39 (m, 4 H); 2.13 (t, 7.5 Hz, 2 H); 2.21 (s, 3 H); 3.32–3.95 (m, 17 H); 4.32 (d, 8.6 Hz, 1 H); 4.50 (d, 8.6 Hz, 1 H); 6.71 (d, 7.6 Hz, 1 H); 7.11 (dd, 1.4 Hz, 7.6 Hz, 1 H); 7.52 (d, 1.4 Hz, 1 H). $^{13}$C-NMR (CD$_3$OD, 62.90 MHz) δ=20.60; 26.00; 27.12; 30.07; 30.28 (2×C); 30.56; 34.77; 51.95; 56.64; 62.00; 62.57; 70.36; 70.75; 72.63; 73.92; 74.83; 76.59; 77.18; 81.15; 102.83; 105.11; 116.37; 118.44; 128.36; 129.05; 135.59; 159.66; 171.77; 176.03.

(c) 26 mg (99%) of compound No. (43) are obtained from 18 mg (28 μmol) of compound No. (42) and 28 mg (43 μmol) of CMP-sia in accordance with Example B1.1(c) (in this case, the buffer solution contains 8% DMSO).

(a) 97 mg (82%) of compound No. (45) are obtained, in accordance with Example B1.10(a), from 44 mg (240 μmol) of 3-hydroxy-4-nitrobenzoic acid (Fluka) and 110 mg (231 μmol) of amine No. (32) in the presence of 100 mg of HBPyU.

(45)

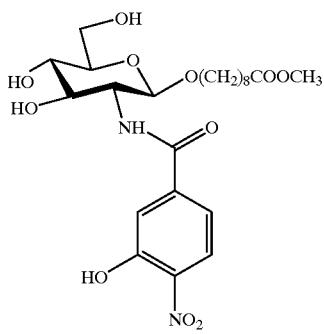

¹H-NMR (CD₃OD-CDCl₃, 250.13 MHz) δ=1.22 (m, 8 H); 1.59 (m, 4 H); 2.35 (t, 7.6 Hz, 2 H); 3.39–3.65 (m, 3 H); 3.71–4.07 (m, 8 H); 4.70 (d, 7.6 Hz, 1 H); 7.53 (dd, 2.1 Hz, 8.3 Hz, 1 H); 7.70 (d, 2.1 Hz, 1 H); 8.23 (d, 8.3 Hz, 1 H). ¹³C-NMR (CD₃OD-CDCl₃, 62.90 MHz) δ=25.55; 29.67; 29.86 (2×C); 30.12; 34.69; 52.30; 57.41; 61.90; 70.84; 71.19; 74.59; 76.93; 102.02; 119.48; 119.77; 126.29; 136.53; 143.03; 154.68; 167.82; 176.04.

(b) 66 mg (89%) of compound No. (46) are obtained from 57 mg (111 μmol) of compound No. (45) and 92 mg (144 μmol) of UDP-gal in accordance with Example B1.1(b) (in this case, the buffer solution contains approximately 7% DMSO).

(46)

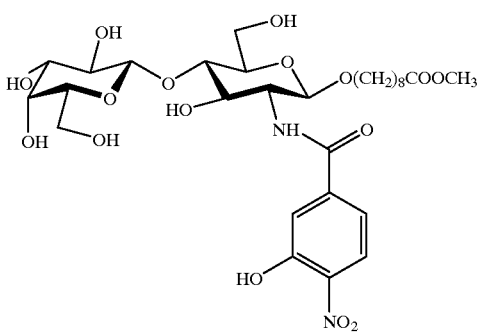

¹H-NMR (CD₃OD, 250.13 MHz) δ=1.02 (m, 8 H); 1.37 (m, 4 H); 2.11 (t, 7.5 Hz, 2 H); 3.31–3.92 (m, 17 H); 4.36 (d, 8.6 Hz, 1 H); 4.50 (d, 8.6 Hz, 1 H); 7.30 (dd, 2.1 Hz, 8.3 Hz, 1 H); 7.47 (d, 2.1 Hz, 1 H); 8.02 (d, 8.3 Hz, 1 H). ¹³C-NMR (CD₃OD, 62.90 MHz) δ=25.71; 26.84; 29.78; 30.00 (2×C); 30.28; 34.68; 52.29; 57.37; 61.14; 62.38; 70.20; 71.09; 72.45; 73.38; 74.58; 76.44; 77.12; 80.55; 102.60; 104.79; 119.30; 120.77; 127.12; 137.92; 143.49; 153.28; 168.75; 176.72.

(c) 11 mg (27%) of compound No. (47) are obtained from 28 mg (42 μmol) of compound No. (46) and 40 mg (60 μmol) of CMP-sia in accordance with Example B1.1(c) (in this case, the buffer solution contains 9% DMSO).

(47)

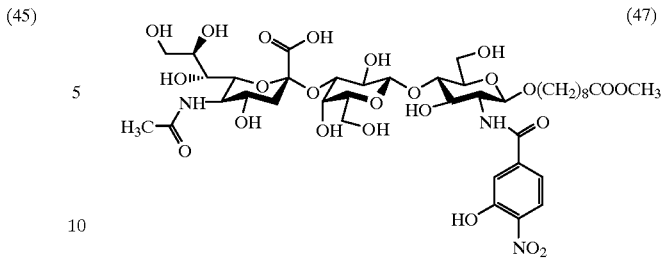

¹H-NMR (CD₃OD, 250.13 MHz) δ=1.08 (m, 8 H); 1.39 (m, 4 H); 1.65 (broad t, 11.6 Hz, 1 H); 1.93 (s, 3 H); 2.13 (t, 7.6 Hz, 2 H); 2.78 (dd, 11.6 Hz, 2.8 Hz, 1 H); 3.32–4.02 (m, 24 H); 4.40 (d, 8.6 Hz, 1 H); 4.46 (d, 8.6 Hz, 1 H); 7.21 (dd, 2.1 Hz, 8.3 Hz, 1 H); 7.42 (d, 2.1 Hz, 1 H); 8.00 (d, 8.3 Hz, 1 H). ¹³C-NMR (CD₃OD, 62.90 MHz) δ=22.60; 25.99; 27.17; 30.07; 30.30; 30.38; 30.62; 34.71; 42.33; 51.97; 53.94; 57.23; 62.02; 62.77; 64.49; 69.05; 69.33; 70.04; 70.70; 70.89; 72.95; 73.93; 74.94; 76.59; 77.11; 77.65; 81.29; 101.51; 102.79; 105.00; 11 8.27; 121.53; 126.66; 143.20; 168.55; 174.73; 175.63; 175.99; remaining signals not resolved.

(d) 11 mg (97%) of compound No. (44) are obtained from 10 mg (10 μmol) of compound No. (47) and 10 mg (16 μmol) of GDP-fuc in accordance with Example B1.1 (d).

¹H-NMR (CD₃OD, 250.13 MHz) δ=1.08 (m, 11 H); 1.39 (m, 4 H); 1.64 (broad t, 11.0 Hz, 1 H); 1.92 (s, 3 H); 2.12 (t, 7.6 Hz, 2 H); 2.79 (dd, 11.6 Hz, 2.8 Hz, 1 H); 3.31 –4.07 (m, 27 H); 4.46 (d, 8.6 Hz, 1 H); 4.51 (broad d, 8.6 Hz, 1 H); 4.74 (broad q, 6.8 Hz, 1 H); 4.96 (d, 4.3 Hz, 1 H); 7.29 (dd, 2.1 Hz, 8.3 Hz, 1 H); 7.48 (d, 2.1 Hz, 1 H); 8.02 (d, 8.3 Hz, 1 H). ¹³C-NMR (CD₃OD, 62.90 MHz) δ=16.56; 22.58; 25.98; 27.22; 30.06; 30.30 (2×C); 30.35; 34.72; 42.68; 51.97; 53.95; 58.42; 61.58; 62.86; 64.40; 67.70; 68.85; 69.30; 69.85; 70.10; 70.66; 70.90; 71.08; 73.44; 73.70; 73.85; 75.00; 75.41; 76.77; 77.34; 100.09; 101.29; 102.81; 103.91; 118.93; 121.48; 126.67; remaining signals not resolved.

Example B1.12

Preparation of Compound No. (48)

(48)

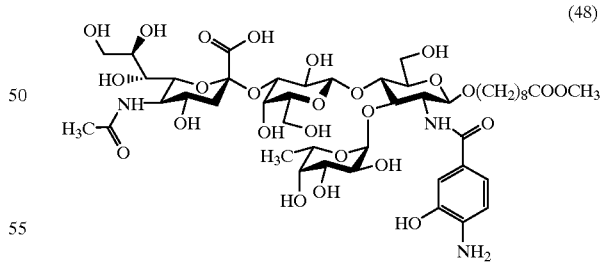

12. 0 mg (12.4 μmol) of tetrasaccharide No. (44) are dissolved, in an argon atmosphere, in 3 ml of dry methanol, and this solution is treated with 35 mg of 10% palladium-carbon and hydrogenated at RT while stirring vigorously. 1 equivalent of dry hydrochloric acid in methanol is then added under argon and the mixture is carefully filtered through Celite. After the solvent has been evaporated off, a pale yellow syrup is obtained which is lyophilized from dioxane/water. Approximately 50% of the resulting white powder (10 mg; 70%) consists of the free amine No. (48), while the other half consists of the corresponding hydrochloride.

$^1$H-NMR (CD$_3$OD, 400.13 MHz) δ=1.05 (m 11 H); 1.34 (m, 4 H); 1.58 (broad t, 1 1.0 Hz, 1 H); 1.92 (s, 3 H); 2.16 (broad t, 7.6 Hz, 2 H); 2.79 (dd, 11.6 Hz, 2.8 Hz, 1 H); 3.32–4.02 (m, 27 H); 4.45 (d, 8.6 Hz, 1 H); 4.52 (broad d, 8.6 Hz, 1 H); 4.72 (broad q, 6.8 Hz, 1 H); 4.99 (d, 4.3 Hz, 1 H); 6.25 (d, 7.8 Hz) and 6.64 (d, 7.8 Hz) together 1 H; 7.05 (m, 2 H).

Example B1.13

Preparation of Compound No. (49)

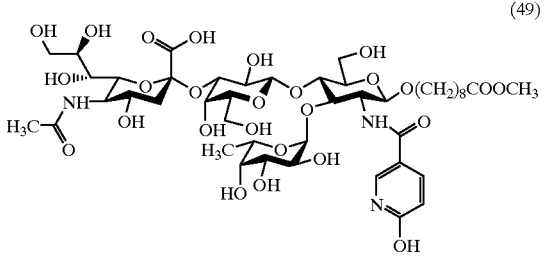

(a) 71 mg (72%) of monossaccharide No. (50) are obtained, in accordance with Example B1.11(a), from 31 mg (220 μmol) of 6-hydroxynicotinic acid (Fluka) and 100 mg (210 μmol) of amine No. (32) in the presence of 100 mg of HBPyU and following subsequent deacetylation and chromatographic purification on silica gel (eluent: methylene chloride/methanol/water-8/2/0.3).

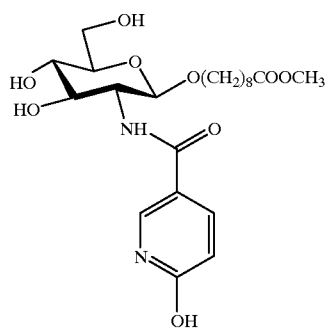

$^1$H-NMR (CD$_3$OD, 250.13 MHz) δ=1.09 (m, 8 H); 1.43 (m, 4 H); 2.19 (t, 7.6 Hz, 2 H); 3.20–3.43 (m, 3 H); 3.50–3.85 (m, 8 H); 4.49 (d, 7.6 Hz, 1 H); 6.50 (d, 8.3 Hz, 1 H); 7.97 (dd, 2.1 Hz, 8.3 Hz, 1 H); 8.03 (d, 2.1 Hz, 1 H). $^{13}$C-NMR (CD$_3$OD-CDCl$_3$, 62.90 MHz) δ=25.61; 26.63; 29.70; 29.87; 29.94; 30.17; 34.70; 52.31; 57.24; 62.13; 70.80; 71.46; 74.99; 77.19; 102.26; 115.76; 119.94; 138.21; 141.01; 165.35; 166.65; 176.42.

(b) 16 mg (46%) of compound No. (51) are obtained from 25 mg (53 μmol) of compound No. (50) and 38 mg (61 μmol) of UDP-gal in accordance with Example B1.1(b) (in this case, the buffer solution contains approximately 7% DMSO).

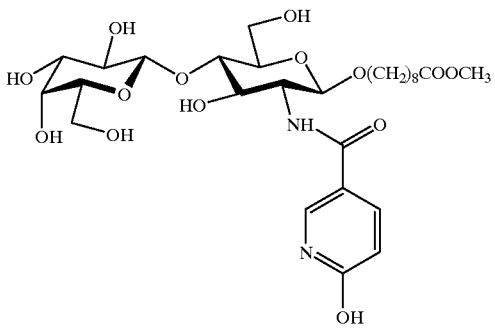

$^1$H-NMR (CD$_3$OD, 250.13 MHz) δ=1.18 (m, 8 H); 1.53 (m, 4 H); 2.29 (t, 7.5 Hz, 2 H); 3.41–4.04 (m, 17 H); 4.48 (d, 8.6 Hz, 1 H); 4.60 (d, 8.6 Hz, 1 H); 6.61 (d, 8.3 Hz, 1 H); 8.05 (dd, 2.1 Hz, 8.3 Hz, 1 H); 8.14 (d, 2.1 Hz, 1 H). $^{13}$C-NMR (CD$_3$OD-CDCl$_3$, 62.90 MHz) δ=25.63; 26.62; 29.70; 29.86; 29.94; 30.14; 34.75; 52.47; 56.80; 61.33; 62.11; 69.76; 71.03; 72.19; 73.36; 74.02; 75.99; 76.57; 80.18; 102.25; 104.29; 115.90; 119.96; 138.30; 141.14; 165.54; 166.71; 176.74.

(c) 19 mg (94%) of compound No. (52) are obtained from 14 mg (22 μmol) of compound No. (51) and 23 mg (35 μmol) of CMP-sia in accordance with Example B1.1(c).

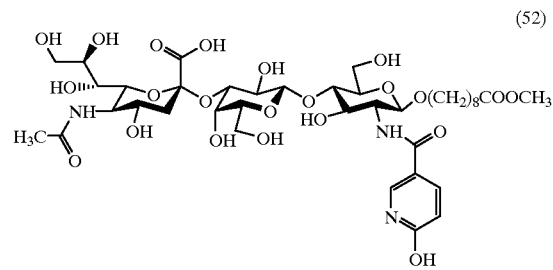

$^1$H-NMR (CD$_3$OD, 250.13 MHz) δ=1.10 (m, 8 H); 1.42 (m, 4 H); 1.75 (broad t, 11.6 Hz, 1 H); 1.97 (s, 3 H); 2.19 (t, 7.6 Hz, 2 H); 2.72 (dd, 11.6 Hz, 2.8 Hz, 1 H); 3.34–4.05 (m, 24 H); 4.44. (d, 8.6 Hz, 1 H); 4.51 (d, 8.6 Hz, 1 H); 6.49 (d, 8.3 Hz, 1 H); 8.01 (dd, 2.1 Hz, 8.3 Hz, 1 H); 8.10 (d, 2.1 Hz, 1 H). $^{13}$C-NMR (CD$_3$OD, 62.90 MHz) δ=22.86; 25.96; 27.11; 30.06; 30.26; 30.39; 30.57; 34.75; 41.31; 52.02; 53.97; 56.83; 61.99; 62.66; 64.26; 69.38; 69.78; 70.17; 70.83; 71.13; 73.32; 74.12; 75.06; 76.44; 76.58; 77.35; 81.42; 101.50; 102.71; 104.92; 115.90; 120.17; 138.61; 141.38; 165.44; 166.75; 175.43; 176.05; 176.51.

(d) 13 mg (60%) of compound No. (49) are obtained from 18 mg (20 μmol) of compound No. (52) and 19 mg (27 μmol) of GDP-fuc in accordance with Example B1.1(d).

$^1$H-NMR (CD$_3$OD-(D$_6$)-DMSO, 400.13 MHz) δ=1.21 (d, 6.8 Hz, 3 H); 1.26 (m, 8 H); 1.56 (m, 4 H); 1.75 (broad t, 11.0 Hz, 1 H); 2.05 (s, 3 H); 2.32 (t, 7.6 Hz, 2 H); 2.93 (dd, 11.6 Hz, 2.8 Hz, 1 H); 3.48–4.12 (m, 27 H); 4.58 (d, 8.6 Hz, 1 H); 4.63 (broad d, 8.6 Hz, 1 H); 4.89 (broad q, 6.8 Hz, 1 H); 5.03 (d, 4.3 Hz, 1 H); 6.58 (d, 8.3 Hz, 1 H); 8.03 (dd, 2.1 Hz, 8.3 Hz, 1 H); 8.12 (d, 2.1 Hz, 1 H). $^{13}$C-NMR (CD$_3$OD-(D$_6$)-DMSO, 100.61 MHz) δ=16.83; 22.79; 25.96; 27.13; 30.04; 30.25; 30.37; 30.57; 34.72; 42.37; 52.04; 54.00; 57.68; 61.12; 62.83; 64.60; 67.60; 68.68; 69.15; 69.78; 70.03; 70.52; 70.20; 70.95; 72.98; 73.51; 73.58; 74.94; 75.42; 76.69; 77.34; 77.89; 100.09; 100.87; 102.32; 103.93;

115.57; 120.20; 138.78; 141.01; 162.30; 166.55; 174.54; 175.22; 175.72.

Example B1.14

Preparation of Compound No. (53)

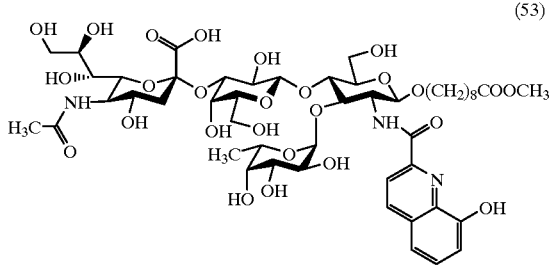
(53)

(a) 36 mg (33%) of monosaccharide No. (54a) are obtained, in acccordance with Example B1.11(a), from 42 mg (220 μmol) of 8-hydroxyquinoline-2-carboxylic acid (Fluka) and 100 mg (210 μmol) of amine No. (32) in the presence of HBPyU.

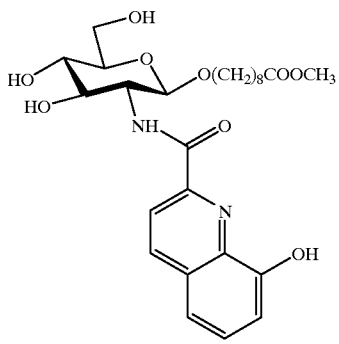
(54a)

$^1$H-NMR (CD$_3$OD, 250.13 MHz) δ=0.38–1.40 (m, 12 H); 1.92 (t, 7.6 Hz, 2 H); 3.28–3.92 (m, 11 H); 4.58 (d, 7.6 Hz, 1 H); 7.09 (dd, 0.9 Hz, 7.6 Hz, 1 H); 7.34 (dd, 0.9 Hz, 7.6 Hz, 1 H); 7.47 (t, 7.6 Hz, 1 H); 8.12 (d, 8.3 Hz, 1 H); 8.31 (d, 8.3 Hz, 1 H). $^{13}$C-NMR (CD$_3$OD, 62.90 MHz) δ=26.52; 27.09; 29.89; 30.17; 30.22; 30.50; 34.64; 51.92; 57.81; 62.82; 70.61; 72.23; 75.94; 78.05; 102.88; 112.78; 118.99; 120.15; 130.57; 131.46; 138.34; 138.82; 148.89; 155.02; 167.04; 175.87.

(b) 31 mg (90%) of compound No. (54) are obtained from 26 mg (50 μmol) of compound No. (53) and 35 mg (57 μmol) of UDP-gal in accordance with Example B1.1(b) (in this case, the buffer solution contains approximately 18% DMSO).

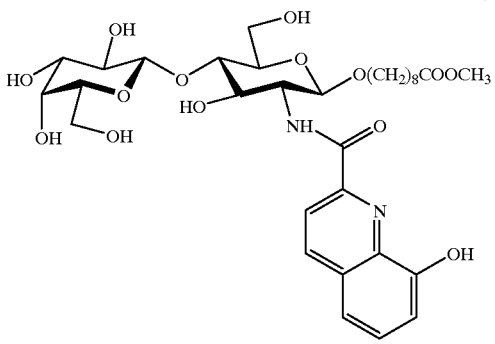
(54)

$^1$H-NMR (CD$_3$OD, 250.13 MHz) δ=0.40–1.41 (m, 12 H); 1.92 (t, 7.5 Hz, 2 H); 3.32–4.01 (m, 17 H); 4.35 (d, 8.6 Hz, 1 H); 4.59 (d, 8.6 Hz, 1 H); 7.08 (dd, 0.9 Hz, 7.6 Hz, 1 H); 7.33 (dd, 0.9 Hz, 7.6 Hz, 1 H); 7.45 (t, 7.6 Hz, 1 H); 8.11 (d, 8.3 Hz, 1 H); 8.33 (d, 8.3 Hz, 1 H). $^{13}$C-NMR (CD$_3$OD, 62.90 MHz) δ=25.78; 27.09; 29.92; 30.18; 30.25; 30.50; 34.65; 51.92; 57.15; 62.04; 62.53; 70.32; 70.65; 72.63; 74.06; 74.83; 76.69; 77.15; 81.24; 102.92; 105.15; 112.77; 118.98; 120.13; 130.58; 131.47; 138.35; 138.83; 148.87; 155.06; 167.87; 175.89.

(c) 23 mg (80%) of compound No. (55) are obtained from 20 mg (29 μmol) of compound No. (54) and 29 mg (44 μmol) of CMP-sia in accordance with Example B1.1(c) (in this case, the buffer solution contains approximately 12% DMSO).

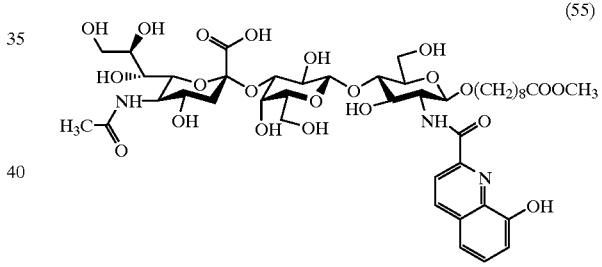
(55)

$^1$H-NMR (CD$_3$OD, 250.13 MHz) δ=0.41–1.41 (m, 12 H); 1.66 (broad t, 11.6 Hz, 1 H); 1.93 (m, 5 H); 2.78 (dd, 11.6 Hz, 2.8 Hz, 1 H); 3.35–4.05 (m, 24 H); 4.42 (d, 8.6 Hz, 1 H); 4.56 (d, 8.6 Hz, 1 H); 7.08 (dd, 0.9 Hz, 7.6 Hz, 1 H); 7.32 (dd, 0.9 Hz, 7.6 Hz, 1 H); 7.45 (t, 7.6 Hz, 1 H); 8.12 (d, 8.3 Hz, 1 H); 8.33 (d, 8.3 Hz, 1 H). $^{13}$C-NMR (CD$_3$OD, 62.90 MHz) δ=22.00; 25.78; 27.10; 29.92; 30.19; 30.25; 30.50; 34.66; 42.19; 51.92; 53.95; 57.07; 62.11; 62.74; 64.49; 69.07; 69.32; 70.04; 70.67; 70.91; 72.96; 74.10; 74.93; 76.68; 77.08; 77.66; 81.44; 101.12; 102.97; 105.08; 112.89; 118.98; 120.05; 130.60; 131.54; 138.45; 138.88; 148.87; 155.06; 167.68; 175.01; 175.51; 175.90.

(d) 13 mg (78%) of compound No. (53) are obtained from 15 mg (15 μmol) of compound No. (55) and 16 mg (25 μmol) of GDP-fuc in accordance with Example B1.1(d).

$^1$H-NMR (CD$_3$OD, 250.13 MHz) δ=0.40–1.41 (m, 15 H); 1.65 (broad t, 11.0 Hz, 1 H); 1.95 (m, 5 H); 2.70 (dd, 11.6 Hz, 2.8 Hz, 1 H); 3.28–4.16 (m, 27 H); 4.49 (d, 8.6 Hz, 1 H); 4.57 (broad d, 8.6 Hz, 1 H); 4.74 (broad q, 6.8 Hz, 1 H); 5.02 (d, 4.3 Hz, 1 H); 7.08 (dd, 0.9 Hz, 7.6 Hz, 1 H); 7.35 (dd, 0.9 Hz, 7.6 Hz, 1 H); 7.48 (t, 7.6 Hz, 1 H); 8.12 (d, 8.3 Hz, 1 H); 8.32 (d, 8.3 Hz, 1 H). $^{13}$C-NMR (CD$_3$OD, 62.90 MHz)

δ=16.51; 22.58; 25.78; 27.12; 29.90; 30.18(2×C); 30.52; 34.67; 42.63; 51.91; 53.98; 57.82; 61.70; 63.05; 64.68; 67.64; 68.84; 69.31; 69.80; 70.14; 70.68; 71.00 (2×C); 73.05; 73.69; 75.02; 75.39; 76.38; 76.79; 77.44; 78.00; 99.87; 100.89; 103.21; 103.93; 113.23; 128.78; 138.89; 174.86; 175.51; 176.54; remaining signals not resolved.

Example B1.15

Preparation of Compound No. (56)

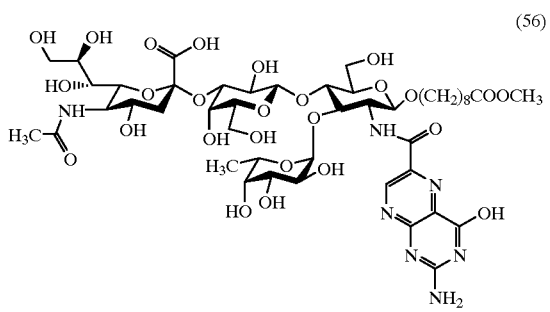

(56)

(a) 62 mg (55%) of monosaccharide No. (57) are obtained, in accordance with Example B1.11(a), from 46 mg (220 μmol) of pterin-6-carboxylic acid (Fluka) and 100 mg (210 μmol) of amine No. (32) in the presence of HBPyU in DMF.

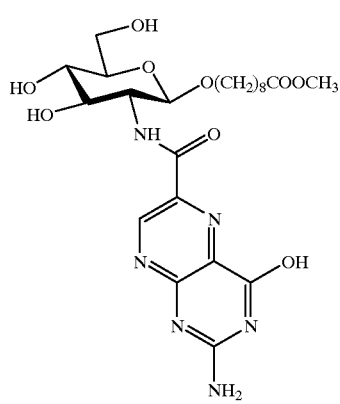

(57)

$^1$H-NMR ((D$_6$)-DMSO, 250.13 MHz) δ=1.02 (m, 8 H); 1.36 (m, 4 H); 2.18 (t, 7.6 Hz, 2 H); 3.18 (broad m, 2 H); 3.33–3.842 (m, 12 H); 4.62 (broad d, 7.6 Hz, 2 H); 5.08 (m, 2 H); 8.45 (broad d, 9.6 Hz, 1 H); 9.19 (s, 1 H). $^{13}$C-NMR ((D$_6$)-DMSO, 62.90 MHz) δ=24.39; 25.52; 28.41; 28.63; 28.78; 29.05; 33.23; 51.24; 55.76; 61.16; 70.89; 72.31; 73.75; 76.93; 100.83; 126.90; 138.68; 148.55; 156.11; 162.90; 173.36; remaining signals not resolved.

(b) 14 mg (37%) of compound No. (58) are obtained from 29 mg (54 μmol) of compound No. (57) and 51 mg (84 μmol) of UDP-gal in accordance with Example B1.1(b) (in this case, the buffer solution contains approximately 9% DMSO).

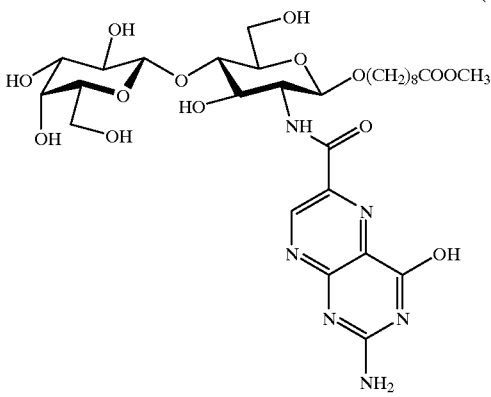

(58)

$^1$H-NMR ((D$_6$)-DMSO, 250.13 MHz) δ=0.72–1.46 (m, 12 H); 2.18 (t, 7.6 Hz, 2 H); 9.16 (s, 1 H); remaining signals broad and not resolved, in part concealed under the solvent. $^{13}$C-NMR DEPT((D$_6$)-DMSO, 62.90 MHz) δ=24.34; 25.44; 28.36; 28.56 (2×C); 28.72; 33.18; 51.18; 55.20; 60.89; 63.70; 68.31; 68.70; 71.01; 72.25; 73.54; 75.40; 76.02; 82.09; 100.94; 104.37; 148.92.

(c) 7 mg (39%) of compound No. (59) are obtained from 12 mg (17 μmol) of compound No. (58) and 17 mg (26 μmol) of CMP-sia in accordance with Example B1.1(c) (in this case, the buffer solution contains approximately 8% DMSO).

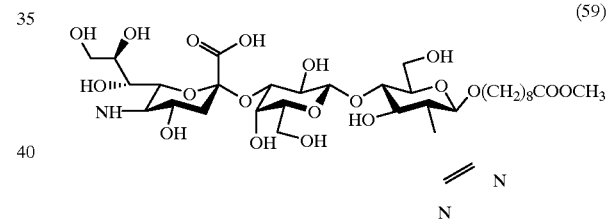

(59)

$^1$H-NMR (CD$_3$OD-D$_2$O-CDCl$_3$, 400.13 MHz) δ=0.72–1.42 (m, 12 H); 1.66 (broad t, 11.0 Hz, 1 H); 1.93 (s, 3 H); 2.16 (t, 7.6 Hz, 2 H); 2.70 (dd, 11.6 Hz, 2.8 Hz, 1 H); 3.34–3.99 (m, 24 H); 4.45 (d, 8.6 Hz, 1 H); 4.50 (d, 8.6 Hz, 1 H); 9.16 (s, 1 H). No $^{13}$C NMR due to the poor solubility!

(d) 7.4 mg (100%) of compound No. (56) are obtained from 6.5 mg (6.5 μmol) of compound No. (59) and 7 mg (11 μmol) of GDP-fuc in accordance with Example B1.1(d).

$^1$H-NMR (CD$_3$OD-D$_2$O-CDCl$_3$, 400.13 MHz) δ=0.68–1.41 (m, 15 H); 1.63 (broad t, 11.0 Hz, 1 H); 1.93 (s, 3 H); 2.68 (dd, 11.6 Hz, 2.8 Hz, 1 H); 3.32–4.06 (m, 27 H); 4.68 (broad q, 6.8 Hz, 1 H); 4.98 (d, 4.3 Hz, 1 H); 9.09 (s, 1 H); remaining signals concealed by the solvent. $^{13}$C-NMR (CD$_3$OD-D$_2$O-CDCl$_3$, 100.61 MHz) δ=15.99; 22.59; 25.30; 26.23; 29.46; 29.56; 29.81; 30.19; 34.51; 39.27; 52.05; 52.93; 53.83; 60.35; 62.20; 63.86; 66.71; 67.19; 67.54; 68.47; 69.02; 69.32; 69.48; 70.07; 70.85; 72.41; 72.69; 74.01; 74.26; 75.54; 76.25; 77.37; 99.11; 100.15; 101.84; 102.74; 128.34; 146.06; 165.44; 174.35; 175.27; 175.89; remaining signals not resolved.

Example B1.16

Preparation of Compound No. (83)

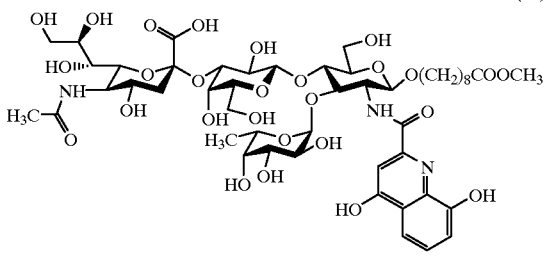

(83)

(a) 139 mg (90%) of amide No. (84) are obtained, in accordance with Example B1.6(a), from 88 mg (429 μmol) of xanthurenic acid (Fluka) and 100 mg (286 μmol) of compound No. (2) in the presence of 184 mg (487 μmol) of HBTU in place of TBTU and 80 μl (572 μmol) of triethylamine in 5 ml of dry DMF.

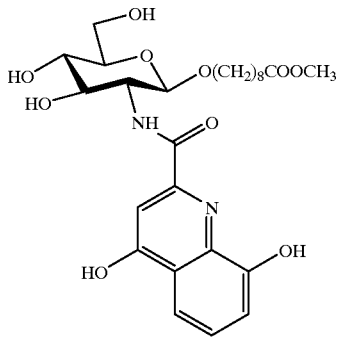

(84)

$^1$H-NMR (CD$_3$OD-CDCl$_3$, 400.13 MHz) δ=0.92–1.54 (broad m, 12 H); 2.17 (t, 7.5 Hz, 2 H); 3.33 (m, 1 H); 3.48–3.59 (m, 2 H); 3.67 (s, 3 H); 3.78–3.87 (m, 2 H); 3.91–4.01 (m, 2 H); 4.06 (t, 9.9 Hz, 1 H); 4.71 (d, 8.6 Hz, 1 H); 7.17 (d, 8.4 Hz, 1 H); 7.26 (broad s, 1 H); 7.35 (broad t, 8.4 Hz, 1 H); 7.74 (broad d, 8.4 Hz, 1 H). $^{13}$C-NMR (CD$_3$OD-CDCl$_3$, 100.6 MHz) δ=25.35; 26.63; 29.53; 29.81 (2×C); 30.10; 34.45; 51.86; 57.44; 62.31; 70.60; 71.69; 74.99; 77.12; 101.95; 114.85; 126.44; 128.39; 131.01; 141.03; remaining signals not resolved.

(b) 19 mg (74%) of compound No. (85) are obtained from 20 mg (37 μmol) of compound No. (84) and 34 mg (56 μmol) of UDP-gal in accordance with Example B1.1(b) (in this case, the buffer solution contains approximately 6.5% DMSO).

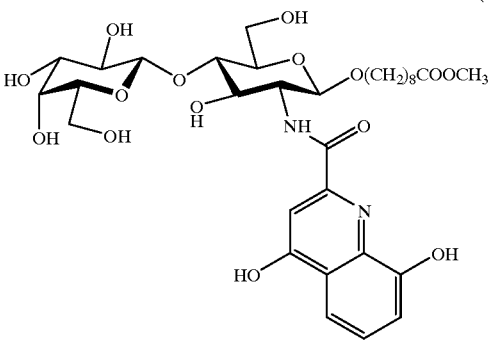

(85)

$^1$H-NMR (CD$_3$OD, 400.13 MHz) δ=0.70–1.40 (m, 12 H); 1.93 (t, 7.5 Hz, 2 H); 3.35–3.95 (m, 17 H); 4.34 (d, 8.6 Hz, 1 H); 4.53 (d, 8.6 Hz, 1 H); 7.03 (d, 8.4 Hz, 1 H); 7.12 (broad s, 1 H); 7.24 (broad t, 8.4 Hz, 1 H); 7.56 (broad d, 8.4 Hz, 1 H). $^{13}$C-NMR (CD$_3$OD, 100.61 MHz) δ=25.81; 27.22; 29.99; 30.30; 30.38; 30.57; 34.67; 51.89; 57.39; 62.02; 62.53; 70.32; 70.78; 72.63; 73.90; 74.85; 76.66; 77.15; 81.21; 102.77; 105.15; 114.75; 127.24; 129.85; 132.40; 175.96; remaining signals not resolved.

(c) 19 mg (75%) of compound No. (86) are obtained from 18 mg (25.8 μmol) of compound No. (85) and 34 mg (55 μmol) of CMP-sia in accordance with Example B1.1(c) (in this case, the buffer solution contains approximately 11.3% DMSO).

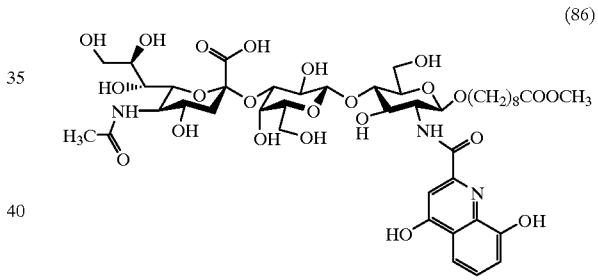

(86)

$^1$H-NMR (CD$_3$OD, 400.13 MHz) δ=0.66–1.42 (m, 12 H); 1.69 (t, 11.0 Hz, 1 H); 1.95 (s, 3 H); 1.97 (t, 7.5 Hz, 2 H); 2.80 (dd, 11.6 Hz, 2.8 Hz, 1 H); 3.37–3.47 (m, 3 H); 3.47–3.72 (m, 12 H); 3.74–4.03 (m, 9 H); 4.43 (d, 8.6 Hz, 1 H); 4.54 (d, 8.6 Hz, 1 H); 7.05 (d, 8.4 Hz, 1 H); 7.16 (broad s, 1 H); 7.26 (broad t, 8.4 Hz, 1 H); 7.60 (broad d, 8.4 Hz, 1 H). $^{13}$C-NMR (CD$_3$OD, 100.6 MHz) δ=22.64; 25.82; 27.22; 29.99; 30.19; 30.31; 30.38; 30.57; 34.67; 41.99; 51.90; 53.96; 57.31; 62.08; 62.73; 64.48; 69.09; 69.31; 70.04; 70.80; 70.88; 72.97; 73.91; 74.92; 76.64; 77.05; 77.64; 81.38; 101.13; 102.81; 105.07; 114.76; 127.20; 149.61; 175.02; 175.50; 175.98; remaining signals not resolved.

(d) 10 mg (89%) of compound No. (83) are obtained from 10 mg (10 μmol) of compound No. (86) and 10 mg (15 μmol) of GDP-fuc in accordance with Example B1.1(d).

$^1$H-NMR (CD$_3$OD, 400.13 MHz) δ=0.55–1.11 (m, 10 H); 1.19 (d, 6.8 Hz, 3 H); 1.29–1.50 (m, 2 H); 1.81 (broad t, 11.0 Hz, 1 H); 1.88 (t, 7.5 Hz, 2 H); 2.05 (s, 3 H); 2.79 (dd, 11.6 Hz, 2.8 Hz, 1 H); 3.51–4.29 (m, 27 H); 4.55 (d, 8.6 Hz, 1 H); 5.14 (d, 4.3 Hz, 1 H); 7.01 (d, 8.4 Hz, 1 H); 7.20 (broad s, 1 H); 7.35 (broad t, 8.4 Hz, 1 H); 7.61 (broad d, 8.4 Hz, 1 H). $^{13}$C-NMR (CD$_3$OD, 100.6 MHz) δ=15.47; 22.23; 24.21;

25.94; 28.26; 28.77; 28.88; 28.98; 33.59; 39.99; 51.90; 52.17; 59.86; 61.72; 62.67; 62.81; 66.94; 67.52; 67.80; 68.32; 68.53; 69.38; 69.50; 70.95; 72.07; 72.25; 73.12; 73.56; 74.84; 75.12; 75.55; 75.87; 99.87; 101.07; 101.83; 106.32; 114.00; 115.95; 126.08; 126.49; 148.94; 163.89; 174.10; 175.23; 177.65; remaining signals not resolved.

Example B2.1

Preparation of Compound No. (65)

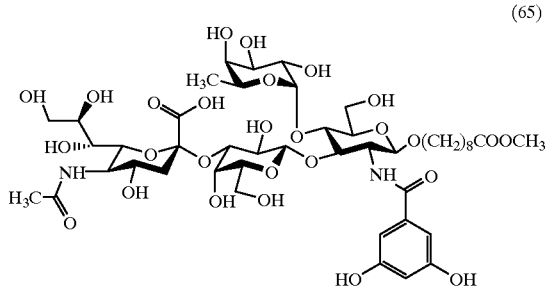

(a) 287 mg (98%) of amide, which is immediately further deacetylated as described in Example B1.8(a), is obtained, in accordance with Example B1.10(a), from 56 mg (360 μmol) of 3,5-dihydroxybenzoic acid (Fluka) and 250 mg (330 μmol) of amine No. (64) in the presence of 155 mg of HBPyU following chromatography of the reaction mixture on silica gel (eluent: methylene chloride/methanol-15/0.5). 137 mg (65%) of disaccharide No. (66) are obtained following renewed chromatography on silica gel (eluent: methylene chloride/methanol/water-6/4/1).

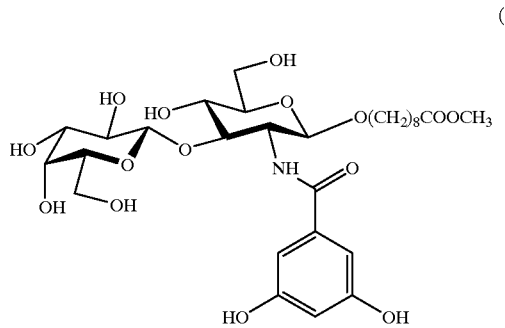

$^1$H-NMR (CD$_3$OD 400.13 MHz) δ=1.08 (m, 8 H); 1.41 (m, 4 H); 2.18 (t, 7.6 Hz, 2 H); 3.19–3.89 (m, 17 H); 4.22 (d, 8.6 Hz, 1 H); 4.56 (broad d, 9.0 Hz, 1H); 6.30 (t, approx. 2.0 Hz, 1 H); 6.64 (d, approx. 2.0 Hz, 2 H). $^{13}$C-NMR (CD$_3$OD, 100.61 MHz) δ=26.53; 27.13; 30.04; 30.23; 30.30; 30.61; 34.76; 51.95; 56.90; 62.39; 62.71; 70.14; 70.69; 70.77; 72.32; 74.36; 76.98; 77.45; 84.24; 102.33; 105.21; 106.57; 107.03 (2×C); 138.03; 159.70 (2×C); 171.39; 176.19.

(b) 43 mg (87%) of compound No. (67) are obtained from 34 mg (37 μmol) of compound No. (66) and 49 mg (74 μmol) of CMP-sia in accordance with Example B1.1(c).

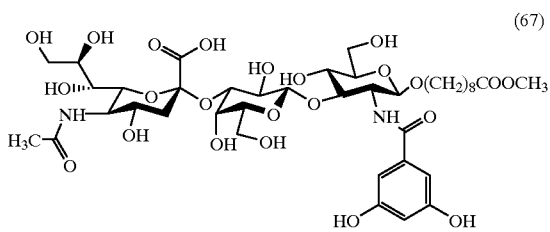

$^1$H-NMR (CD$_3$OD, 400.13 MHz) δ=1.12 (m, 8 H); 1.46 (m, 4 H); 1.72 (broad t, 11.6 Hz, 1 H); 1.98 (s, 3 H); 2.22 (t, 7.6 Hz, 2 H); 2.74 (dd, 11.6 Hz, 2.8 Hz, 1 H); 3.33 (m, 1 H); 3.42–3.75 (m, 16 H); 3.83–3.97 (m, 7 H); 4.38 (d, approx. 8.6 Hz, 1 H); 4.59 (broad d, approx. 8.6 Hz, 1 H); 6.37 (t, approx. 2.0 Hz, 1 H); 6.68 (d, approx. 2.0 Hz, 2 H). $^{13}$C-NMR (CD$_3$OD, 100.61 MHz) δ=22.74; 25.99; 27.14; 30.09; 30.30; 30.36; 30.67; 34.80; 41.40; 51.97; 53.91; 56.71; 62.61; 62.78; 63.96; 69.34; 69.71; 70.00; 70.67; 70.78; 70.83; 72.89; 74.85; 76.68; 77.30; 77.45; 82.95; 101.56; 102.56; 104.07; 106.74; 107.70 (2×C); 138.23; 159.71 (2×C); 171.33; 175.21; 175.48; 176.23.

(c) 15 mg (87%) of compound No. (65) are obtained from 15 mg (16 μmol) of compound No. (67) and 14 mg (22 μmol) of GDP-fuc in accordance with Example B1.1(d). In this case, fucosyl transferase III is used in place of fucosyl transferase VI.

$^1$H-NMR (CD$_3$OD, 400.13 MHz) δ=1.13 (m, 11 H); 1.46 (m, 4 H); 1.71 (broad t, 1 1.0 Hz, 1 H); 1.96 (s, 3 H); 2.20 (t, 7.6 Hz, 2 H); 2.78 (dd, 2.8 Hz, 11.6 Hz, 1 H); 3.36–3.89 (m, 27 H); 4.22 (broad d, 8.6 Hz, 1 H); 4.46 (broad d, 8.6 Hz, 1 H); 4.72 (broad q, 6.8 Hz, 1 H); 5.01 (d, 4.3 Hz, 1 H); 6.35 (t, approx. 3.0 Hz, 1 H); 6.68 (d, approx. 3 Hz, 2 H). $^{13}$C-NMR (CD$_3$OD, 100.61 MHz) δ=16.72; 22.62; 26.01; 27.22; 30.11; 30.27; 30.38; 30.73; 34.81; 42.16; 51.96; 53.87; 58.41; 61.41; 63.08; 63.81; 67.76; 69.07; 69.54; 70.09; 70.81; 71.00; 71.16; 72.89; 73.71; 73.95; 74.95; 76.47; 77.26; 77.53; 99.51; 101.83; 102.05; 102.30; 103.69; 106.85 (2×C); 138.42; 159.87 (2×C); 171.60; 174.88; 175.44; 176.23.

Example B2.2

Preparation of Compound No. (68)

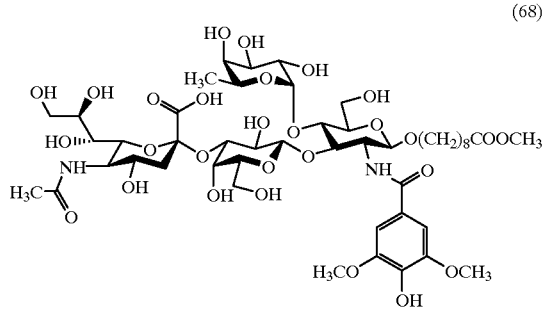

(a) 78 mg (34%) of compound No. (69) are obtained from 72 mg (360 μmol) of syringic acid (Fluka) and 250 mg (327 μmol) of compound No. (64) in accordance with Example B2.1(a).

(69)

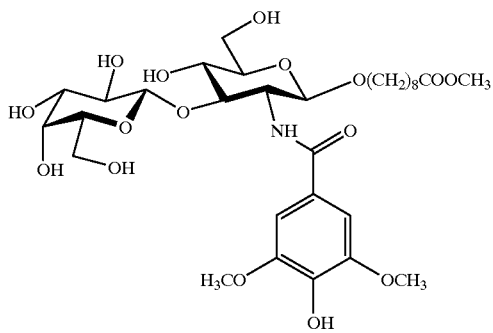

¹H-NMR (CD₃OD, 400.13 MHz) δ=0.88–1.55 (m, 12 H); 2.23 (t, 7.6 Hz, 2 H); 3.42–4.10 (m, 23 H); 4.39 (d, 8.6 Hz, 1 H); 4.75 (d, 8.6 Hz, 1 H); 7.26 (s, 2 H). ¹³C-NMR (CD₃OD, 100.61 MHz) δ=25.62; 26.83; 29.64; 29.93; 29.97; 30.21; 34.64; 52.50; 56.83; 57.05 (2×C); 62.22; 62.27; 69.82; 70.06; 71.12; 71.99; 74.02; 76.65; 76.95; 83.11; 102.20; 104.72; 106.15 (2×C); 125.67; 139.76; 148.61 (2×C); 170.62; 177.19.

(b) 31 mg (60%) of compound No. (70) are obtained from 36 mg (52 μmol) of compound No. (69) and 46 mg (70 μmol) of CMP-sia in accordance with Example B1.1(c).

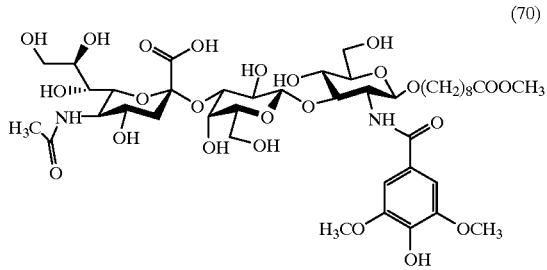

¹H-NMR (CD₃OD, 400.13 MHz) δ=1.08 (m, 8 H); 1.43 (m, 4 H); 1.76 (broad t, 11.0 Hz, 1 H); 1.96 (s, 3 H); 2.18 (t, 7.6 Hz, 2 H); 2.70 (dd, 11.0 Hz, 2.8 Hz, 1 H); 3.34 (m, 1 H); 3.40–3.74 (m, 18 H); 3.80–4.03 (m, 11 H); 4.39 (d, 8.6 Hz, 1 H); 4.74 (d, 8.6 Hz, 1 H); 7.17 (s, 2 H). ¹³C-NMR (CD₃OD, 100.61 MHz) δ=22.68; 25.95; 27.18; 30.06; 30.35; 30.36; 30.64; 34.73; 41.40; 51.95; 53.94; 56.70; 57.06 (2×C); 62.65; 62.82; 63.94; 69.15; 69.35; 69.62; 70.75; 70.88; 70.99; 72.81; 74.86; 76.77; 77.29; 77.53; 83.39; 101.37; 102.76; 104.31; 106.36 (2×C); 126.04; 140.23; 148.89 (2×C); 170.42; 175.26; 175.45; 176.09.

(c) 12 mg (70%) of compound No. (68) are obtained from 15 mg (14.7 μmol) of compound No. (70) and 14 mg (22 μmol) of GDP-fuc in accordance with Example B2.1(c).

¹H-NMR (CD₃OD, 400.13 MHz) δ=1.02 (m, 8 H); 1.10 (d, 6.8 Hz, 3 H); 1.36 (m, 4 H); 1.60 (broad t, 11.0 Hz, 1 H); 1.91 (s, 3 H); 2.15 (t, 7.6 Hz, 2 H); 2.69 (dd, 2.8 Hz, 11.6 Hz, 1 H); 3.29 (m, 1 H); 3.34–3.94 (m, 31 H); 4.30 (m, 1 H); 4.48 (d, 8.6 Hz, 1 H); 4.69 (d, 8.6 Hz, 1 H); 5.01 (d, 4.3 Hz, 1 H); 7.14 (s, 2 H). ¹³C-NMR (CD₃OD, 100.61 MHz) δ=16.72; 22.65; 25.95; 27.01; 30.08; 30.33; 30.36; 30.66; 34.75; 41.67; 51.94; 53.86; 57.08 (2×C); 58.54; 61.63; 63.16; 63.80; 67.87; 68.71; 69.45; 69.56; 70.10; 70.74; 71.12; 71.17; 72.68; 73.68; 74.34; 74.80; 76.48; 77.21; 77.36; 77.53; 99.59; 101.30; 102.46; 103.75; 106.28 (2×C); 125.91; 140.40; 148.99 (2×C); 170.43; 175.33.

Example B2.3

Preparation of Compound No. (71)

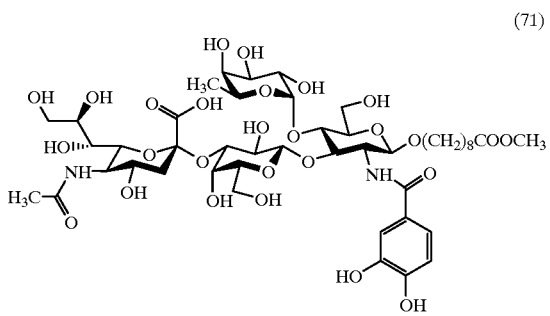

(a) Following chromatography on silica gel (eluent: ethyl acetate/hexane-3/1), 160 mg (57%) of the primary step to compound No. (72) are obtained, in accordance with Example B1.10(a), from 90 mg (378 μmol) of 3,4-di-O-acetylbenzoic acid and 240 mg (314 μmol) of compound No. (64) in the presence of 143 mg (380 μmol) of HBTU and 44 μl (310 μmol) of triethylamine in 3 ml of dry acetonitrile. Subsequently, all the acetyl groups are eliminated, as described in Example B1.8(a), with the aid of a solution of sodium methoxide. 54 mg (47%) of the compound No. (72) are obtained following chromatography on silica gel (eluent: methylene chloride/methanol/water-10/4/0.8).

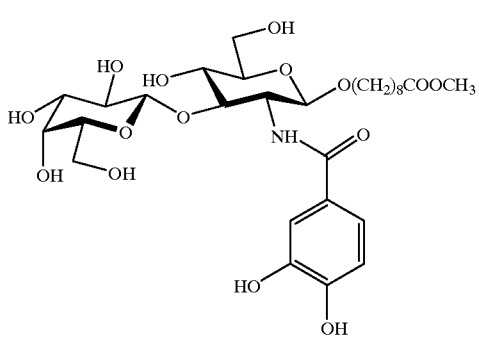

¹H-NMR (CD₃OD-CDCl₃, 400.13 MHz) δ=0.91–1.25 (m, 8 H); 1.34–1.46 (m, 4 H); 2.18 (t, 7.5 Hz, 2 H); 3.30–3.38 (m, 2 H); 3.39–3.48 (m, 4 H); 3.54–3.72 (m, 7 H); 3.73–3.85 (m, 3 H); 3.90 (t, 7.3 Hz, 1 H); 4.24 (d, 8.6 Hz, 1 H); 4.63 (d, 8.6 Hz, 1 H); 6.77 (d, 7.3 Hz, 1 H); 7.17 (dd, 1.2 Hz, 7.3 Hz, 1H); 7.22 (d, 1.2 Hz, 1 H); ¹³C-NMR (CD₃OD-CDCl₃, 100.61 MHz) δ=25.63; 26.67; 29.70; 29.86; 29.92; 30.21; 34.73; 52.33; 56.64; 62.11; 62.18; 69.68; 70.16; 70.99; 71.90; 73.76; 76.46; 76.71; 83.09; 101.94; 104.51; 111.71; 115.92; 120.97; 126.69; 145.48; 149.62; 170.74; 176.66.

(b) 12 mg (63%) of compound No. (73) are obtained from 13 mg (20 μmol) of disaccharide compound No. (72) and 15 mg (23 μmol) of CMP-sia in accordance with Example B1.1(c).

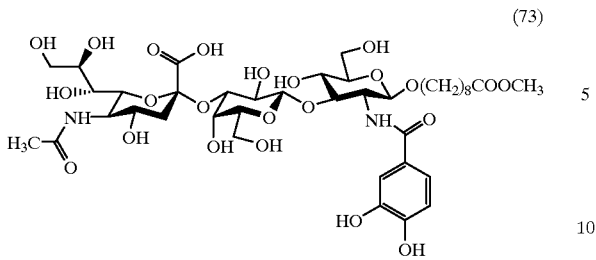

(73)

$^1$H-NMR (CD$_3$OD, 400.13 MHz) δ=0.94–1.30 (m, 8 H); 1.32–1.50 (m, 4 H); 1.64 (t, 11.0 Hz, 1 H); 1.93 (s, 3 H); 2.19 (t, 7.6 Hz, 2 H); 2.74 (dd, 2.8 Hz, 11.0 Hz, 1 H); 3.29 (m, 1 H); 3.33–3.72 (m, 16 H); 3.74–3.98 (m, 7 H); 4.35 (d, 8.6 Hz, 1 H); 4.57 (d, 8.6 Hz, 1 H); 6.70 (d, 7.3 Hz, 2 H); 7.14 (dd, 7.3 Hz, 1.2 Hz, 1 H); 7.20 (d, 1.2 Hz, 1 H). No long-term $^{13}$C-NMR measurement is performed due to the sensitivity of the compound to oxidation in organic solvents.

(c) 7 mg (56%) of compound No. (71) are obtained from 11 mg (12 μmol) of compound No. (73) and 11 mg (18 μmol) of GDP-fuc in accordance with Example B2.1(c).

$^1$H-NMR (CD$_3$OD, 400.13 MHz) δ=0.96–1.28 (m, 11 H); 1.35–1.47 (m, 4 H); 1.68 (t, 11.0 Hz, 1 H); 1.93 (s, 3 H); 2.19 (t, 7.6 Hz, 2 H); 2.74 (dd, 2.8 Hz, 11.0 Hz, 1 H); 3.33–3.89 (m, 27 H); 4.31 (broad d, 8.6 Hz, 1 H); 4.44 (d, 8.6 Hz, 1 H); 4.71 (broad q, 6.8 Hz, 1 H); 4.99 (d, 4.2 Hz, 1 H); 6.79 (d, 7.3 Hz, 1 H); 7.14 (dd, 7.3 Hz, 1.2 Hz, 1 H); 7.21 (d, 1.2 Hz, 1 H). $^{13}$C-NMR (CD$_3$OD, 100,61 MHz) δ=16.71; 22.62; 26.00; 27.18; 30.10; 30.32; 30.35; 30.68; 34.80; 41.93; 51.96; 53.80; 58.80; 61.57; 63.08; 64.18; 67.76; 68.93; 69.68; 70.12; 70.75; 71.10; 71.16; 72.85; 73.72; 74.04; 74.89; 76.43; 77.00; 77.28; 77.85; 99.51; 101.84; 102.17; 103.72; 115.79; 116.15; 120.86; 127.55; remaining signals not resolved.

Example B2.4

Preparation of Compound No. (74)

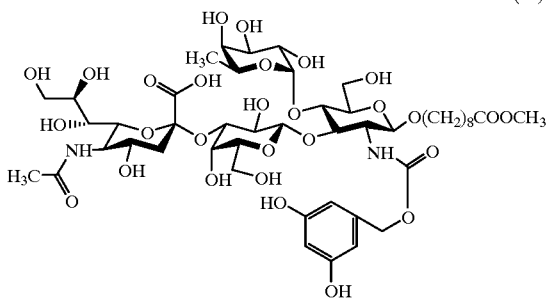

(74)

(a) The per acetylated amide, which is subsequently deacetylated in analogy with Example B1.8(a), is obtained from 66 mg (290 μmol) of 3,5-di-O-acetylbenzyloxycarbonyl chloride and 250 mg (327 μmol) of compound No. (64) in accordance with Example B1.5(a). 37 mg (19%) are obtained of the compound No. (75).

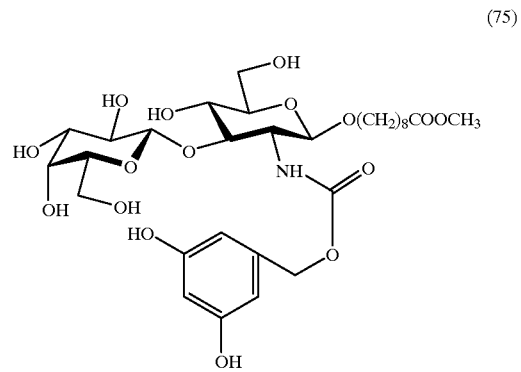

(75)

$^1$H-NMR (CD$_3$OD, 400.13 MHz) δ=1.24 (m, 8 H); 1.51 (m, 4 H); 2.25 (t, 7.5 Hz, 2 H); 3.35–3.87 (m, 17 H); 4.32 (d, 8.6 Hz, 2 H); 4.44 (t, 13.1 Hz, 2H); 4.89 (m, 2 H); 6.15 (t, 0.7 Hz, 1 H); 6.27 (d, 0.7 Hz, 2 H). $^{13}$C-NMR (CD$_3$OD, 62.89 MHz) δ=25.99; 26.95; 30.10; 30.23; 30.30; 30.53; 34.80; 51.98; 58.13; 62.53; 62.70; 67.46; 70.29; 70.59; 70.86; 72.56; 74.44; 77.42 (2×C); 84.14; 102.64; 102.98; 105.09; 106.96 (2×C); 140.40; 159.05; 159.62 (2×C); 176.17.

(b) 32 mg (61%) of compound No. (76) are obtained from 37 mg (55 μmol) of compound No. (75) and 48 mg (73 μmol) of CMP-sia in accordance with Example B1.1(c) (in this case, the reaction mixture contains 8% DMSO).

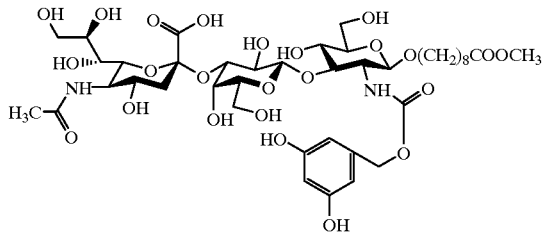

(76)

$^1$H-NMR (CD$_3$OD, 400.13 MHz) δ=1.20 (m, 8 H); 1.48 (m, 4 H); 1.72 (broad t, 11.6 Hz, 1 H); 1.99 (s, 3 H); 2.26 (t, 7.6 Hz, 2 H); 2.82 (dd, 11.6 Hz, 2.8 Hz, 1 H); 3.35–3.97 (m, 23 H); 4.04 (m, 1 H); 4.44 (m, 2 H); 4.99 (m, 2 H); 6.16 (t, approx. 2.0 Hz, 1 H); 6.30 (d, approx. 2.0 Hz, 2 H). $^{13}$C-NMR (CD$_3$OD, 100.61 MHz) δ=22.71; 25.99; 26.95; 30.11; 30.24; 30.29; 30.53; 34.80; 41.79; 51.99; 53.93; 58.22; 62.74 (2×C); 64.29; 67.82; 68.11; 69.27; 69.35; 69.92; 70.50; 70.86; 72.61; 74.87; 76.67; 77.38; 83.79; 101.19; 102.54; 103.03; 104.49; 107.06 (2×C); 140.42; 159.55 (2×C); 175.51; 176.20; remaining signals not resolved.

(c) 7 mg (52%) of compound No. (74) are obtained from 11 mg (11.0 μmol) of compound No. (76) and 15 mg (23 μmol) of GDP-luc in accordance with Example B2.1(c).

$^1$H-NMR (CD$_3$OD, 400.13 MHz) δ=1.13 (d, 6.8 Hz, 3 H); 1.24 (m, 8 H); 1.48 (m, 4 H); 1.73 (broad t, 11.0 Hz, 1 H); 1.97 (s, 3 H); 2.25 (t, 7.6 Hz, 2 H); 2.83 (dd, 2.8 Hz, 11.6 Hz, 1 H); 3.27–3.9 (m, 26 H); 4.10 (m, 1 H); 4.38 (broad d, 8.6 Hz, 1 H); 4.62 (broad d, 8.6 Hz, 1 H); 4.77 (broad q, 6.8 Hz, 1 H); 4.97 (d, 4.3 Hz, 1 H); 5.04 (m, 2 H); 6.14 (t, approx. 3.0 Hz, 1 H); 6.34 (d, approx. 3 Hz, 2 H). $^{13}$C-NMR (CD$_3$OD, 100.61 MHz) δ=16.73; 22.67; 26.10; 27.05; 30.21; 30.37; 30.67; 30.97; 34.91; 42.12; 52.06; 54.02;

59.91; 61.29; 61.57; 63.40; 64.39; 67.74; 68.22; 69.61; 70.00; 70.20; 70.94; 71.25; 72.75; 73.86 (2×C); 75.04; 76.11; 77.29; 77.51; 77.68; 77.81; 99.53; 101.11; 101.91; 103.42; 103.83; 107.83 (2×C); 140.69; 158.20; 159.66 (2×C); 175.53; remaining signals not resolved.

Example B2.5

Preparation of Compound No. (77)

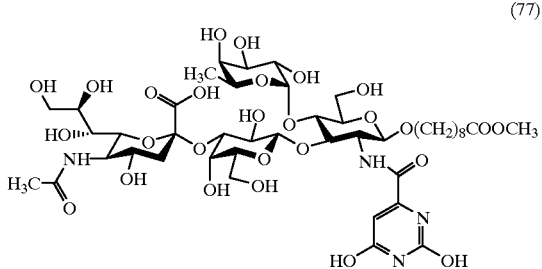

(77)

(a) 104 mg (63%) of amide No. (78) are obtained from 45 mg (288 μmol) of orotic acid (Fluka) and 200 mg (262 μmol) of compound No. (64) in accordance with Example B2.1(a).

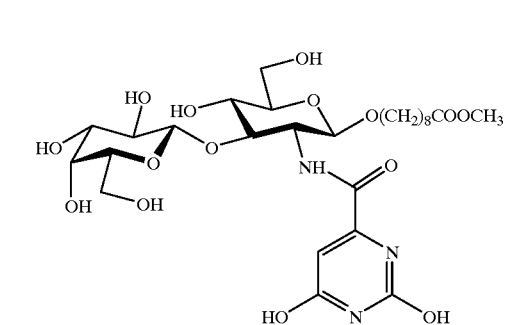

(78)

$^1$H-NMR ((D$_6$)-DMSO, 250.13 MHz) δ=1.18 (m, 8 H); 1.43 (m, 4 H); 2.26 (t, 7.5 Hz, 2 H); 3.17–3.79 (m, 17 H); 4.14 (m, 3 H); 4.48 (d, 8.6 Hz, 1 H); 4.55 (d, 8.6 Hz, 1 H); 4.67 (m, 2 H); 4.83 (s, 1 H); 4.88 (m, 1 H); 6.00 (s, 1 H); 8.75 (broad, 1 H). $^{13}$C-NMR ((D$_6$)-DMSO, 62.89 MHz) δ=24.51; 25.57; 28.52; 28.78; 28.86; 29.09; 33.34; 48.67; 54.48; 60.50 (2×C); 68.71; 68.76; 69.32; 70.40; 73.20; 75.70; 76.53; 84.49; 99.47; 100.39; 104.40; 146.61; 151.84; 160.96; 164.46; 173.50.

(b) 55 mg (73%) of compound No. (79) are obtained from 50 mg (77 μmol) of compound No. (78) and 69 mg (104 μmol) of CMP-sia in accordance with Example B1.1(c) (in this case, the reaction mixture contains 8% DMSO).

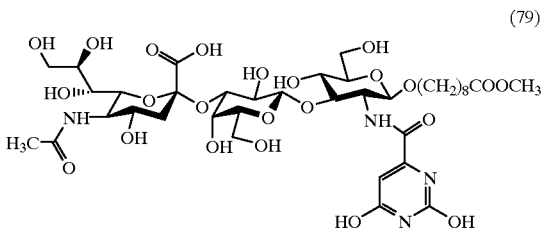

(79)

$^1$H-NMR (CD$_3$OD, 250.13 MHz) δ=1.18 (m, 8 H); 1.46 (m, 4 H); 1.66 (broad t, 11.0 Hz, 1 H); 1.93 (s, 3 H); 2.22 (t, 7.6 Hz, 2 H); 2.73 (broad d, 11.0 Hz, 1 H); 3.26–4.00 (m, 24 H); 4.31 (d, 8.6 Hz, 1 H); 4.52 (d, 8.6 Hz, 1 H); 6.10 (s, 1 H). $^{13}$C-NMR (CD$_3$OD, 62.89 MHz) δ=22.78; 26.00; 27.91; 30.10; 30.32; 30.44; 30.59; 34.77; 41.62; 52.02; 53.89; 56.57; 62.64 (2×C); 64.29; 69.01; 69.28; 69.84; 70.77 (3×C); 73.10; 74.86; 76.79; 77.36; 77.51; 84.17; 101.13 (2×C); 102.14; 105.35; 148.07; 153.97; 162.74; 167.10; 175.15; 175.46; 176.11.

(c) 13 mg (80%) of compound No. (77) are obtained from 14 mg (14.0 μmol) of compound No. (79) and 18 mg (28 μmol) of GDP-fuc in accordance with Example B2.1(c).

$^1$H-NMR (CD$_3$OD, 400.13 MHz) δ=1.13 (d, 6.8 Hz, 3 H); 1.19 (m, 8 H); 1.49 (m, 4 H); 1.74 (broad t, 11.0 Hz, 1 H); 1.96 (s, 3 H); 2.26 (t, 7.6 Hz, 2 H); 2.75 (dd, 11.0 Hz, 3.4 Hz, 1 H); 3.35–3.96 (m, 26 H); 4.16 (t, 9.9 Hz, 1 H); 4.43 (d, 8.6 Hz, 2 H); 4.56 (d, 8.6 Hz, 1 H); 4.74 (broad q, 6.8 Hz, 1 H); 5.03 (d, 4.8 Hz, 1 H); 6.10 (s, 1 H). $^{13}$C-NMR (CD$_3$OD, 126 MHz) δ=16.67; 22.66; 26.00; 27.23; 30.12; 30.34; 30.43; 30.63; 34.79; 41.51; 51.98; 53.97; 58.26; 61.48; 63.16; 64.31; 67.81; 69.70; 69.66; 69.97; 70.05; 70.79; 71.00; 71.13; 72.99; 73.71; 73.85; 74.90; 76.42; 77.42; 77.50; 77.58; 99.55; 100.78; 101.66; 102.12; 104.12; 175.38 (2×C); 176.12; remaining signals not resolved.

Example B2.6

Preparation of Compound No. (80)

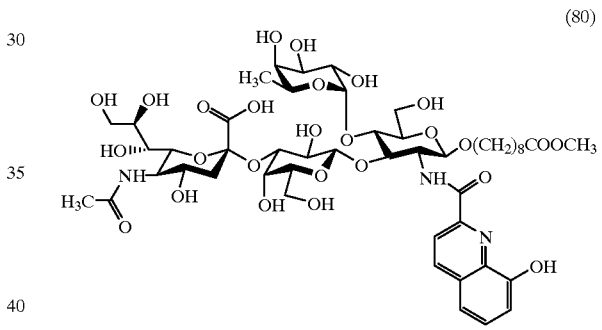

(80)

(a) 162 mg (73%) of compound No. (81) are obtained from 68 mg (360 μmol) of 8-hydroxyquinoline-2-carboxylic acid (Fluka) and 250 mg (327 μmol) of compound No. (64) in accordance with Example B2.1(a).

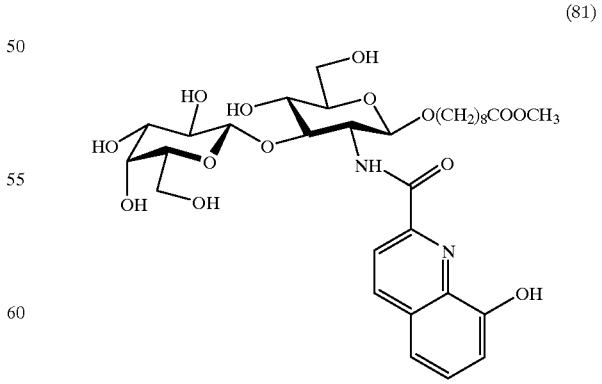

(81)

$^1$H-NMR (CD$_3$OD, 250.13 MHz) δ=0.45–1.46 (m, 12 H); 1.98 (t, 7.5 Hz, 2 H); 3.26 (dd, 4.1 Hz, 11.6 Hz, 1 H); 3.36–4.15 (m, 16 H); 4.34 (d, 8.6 Hz, 1 H); 4.74 (d, 8.6 Hz,

1 H); 7.14 (dd, 0.6 Hz, 7.6 Hz, 1 H); 7.39 (dd, 0.6 Hz, 7.6 Hz, 1 H); 7.50 (t, 7.6 Hz, 1 H); 8.18 (d, 8.3 Hz, 1 H); 8.35 (d, 8.3 Hz, 1 H). $^{13}$C-NMR (CD$_3$OD, 62.90 MHz) δ=25.72; 27.05; 29.84; 30.16 (2×C); 30.4; 34.61; 51.92; 56.67; 62.42; 62.71; 70.07; 70.55; 70.69; 72.20; 74.26; 76.95; 77.58; 84.18; 102.52; 105.00; 112.72; 118.96; 120.25; 130.58; 131.45; 138.31; 138.77; 148.69; 154.89; 167.33; 175.51.

(b) 39 mg (82%) of compound No. (82) are obtained from 33 mg (48 μmol) of compound No. (81) and 38 mg (58 μmol) of CMP-sia in accordance with Example B1.1(c) (in this case, the buffer solution contains approximately 8% DMSO).

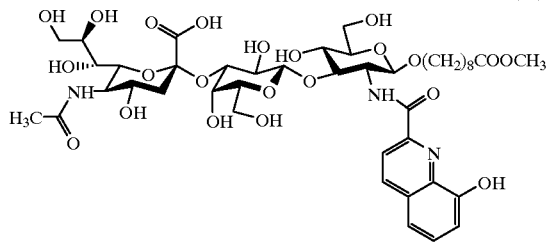

(82)

$^1$H-NMR (CD$_3$OD, 400.13 MHz) δ=0.47–1.43 (m, 12 H); 1.59 (broad t, 11.6 Hz, 1 H); 1.93 (s, 3 H); 1.97 (t, 7.5 Hz, 2 H); 2.67 (dd, 11.6 Hz, 2.8 Hz, 1 H); 3.28–4.13 (m, 25 H); 4.44 (d, 8.6 Hz, 1 H); 4.66 (d, 8.6 Hz, 1 H); 7.14 (dd, 0.9 Hz, 7.6 Hz, 1 H); 7.37 (dd, 0.9 Hz, 7.6 Hz, 1 H); 7.50 (t, 7.6 Hz, 1 H); 8.16 (d, 8.3 Hz, 1 H); 8.38 (d, 8.3 Hz, 1 H). $^{13}$C-NMR (CD$_3$OD, 100.61 MHz) δ=22.66; 25.77; 27.10; 29.89; 30.17; 30.49; 30.88; 34.67; 41.46; 51.92; 53.83; 56.38; 62.60; 62.78; 63.86; 68.99; 69.27; 69.53; 70.66; 70.73; 72.67; 74.76; 76.78; 77.21; 77.60 (2×C); 83.43; 101.20; 102.80; 103.95; 112.92; 118.94; 120.15; 130.75; 131.60; 138.58; 139.02; 148.63; 155.28; 167.30; 175.43; 175.91.

(c) 9 mg (52%) of compound No. (80) are obtained from 14 mg (14.0 μmol) of compound No. (82) and 13 mg (20 μmol) of GDP-fuc in accordance with Example B2.1(c).

$^1$H-NMR (CD$_3$OD, 250.13 MHz) δ=0.40–1.47 (m, 15 H); 1.49 (broad t, 11.0 Hz, 1 H); 1.90 (s, 3 H); 1.95 (t, 7.5 Hz, 2 H); 2.61 (dd, 11.6 Hz, 2.8 Hz, 1 H); 3.25–3.91 (m, 24 H); 4.09 (t, 11.0 Hz, 1 H); 4.49 (d, 8.6 Hz, 1 H); 4.64 (m, 2 H); 5.03 (d, 4.3 Hz, 1 H); 7.09 (dd, 0.9 Hz, 7.6 Hz, 1 H); 7.35 (dd, 0.9 Hz, 7.6 Hz, 1 H); 7.46 (t, 7.6 Hz, 1 H); 8.12 (d, 8.3 Hz, 1 H); 8.47 (d, 8.3 Hz, 1 H). $^{13}$C-NMR (CD$_3$OD, 62.90 MHz) δ=16.72; 22.60; 25.83; 27.12; 29.91; 30.38; 30.17 (2×C); 30.52; 34.69; 41.56; 51.93; 53.77; 57.98; 61.59; 63.24; 63.91; 67.90; 68.80; 69.49 (2×C); 70.05; 70.73; 70.99; 71.15; 72.54; 73.68; 74.05; 74.73; 76.44; 77.40 (2×C); 77.56; 99.56; 101.34; 102.74; 103.49; 113.46; 118.02; 120.55; 129.95; 131.69; 137.71; 139.18; 149.52; 155.82; 167.97; 175.19; 175.31; 175.93.

Example B2.7

Preparation of Compound No. (87)

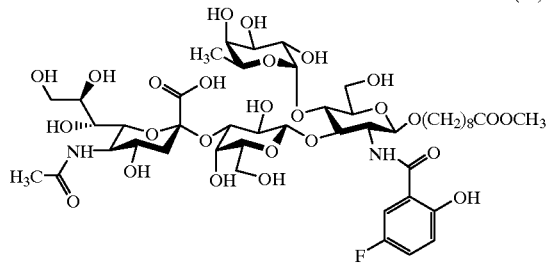

(87)

(a) 62 mg (49%) of amide No. (91) are obtained, in accordance with Example B1.16(a), from 37 mg (235 μmol) of 5-fluorosalicylic acid (Fluka) and 100 mg (195 μmol) of compound No. (90) in the presence of 89 mg (235 μmol) of HBTU and 33 μl (235 μmol) of triethylamine in 3 ml of dry DMF.

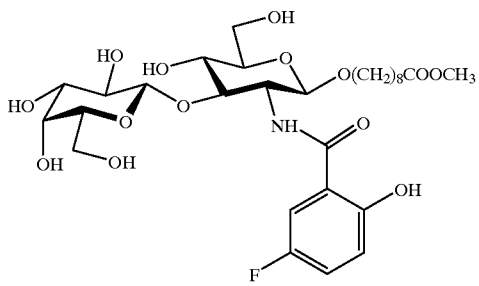

(91)

$^1$H-NMR (CD$_3$OD-CDCl$_3$-D$_2$O, 400.13 MHz) δ=1.36–1.62 (m, 8 H); 1.79–1.93 (m, 4 H); 2.60 (t, 7.5 Hz, 2 H); 3.76–4.39 (m, 17 H); 4.69 (d, 8.6 Hz, 1 H); 5.09 (d, 8.6 Hz, 1 H); 7.26 (dd, 4.9 Hz, 8.0 Hz, 8.3 Hz, 1 H); 7.47 (dt, 3.2 Hz, 8.0 Hz, 1 H); 7.88 (dd, 3.1 Hz, 9.8 Hz, 1 H). $^{13}$C-NMR (CD$_3$OD-CDCl$_3$-D$_2$O, 100.6 MHz) δ=25.29; 26.28; 29.40; 29.50; 29.56; 29.82; 34.50; 52.00; 55.88; 61.71; 61.76; 69.21; 69.56; 70.72; 71.38; 73.34; 75.95; 76.13; 82.52; 101.44; 104.02; 114.06 (d, 25.7 Hz); 116.74 (d, 6.6 Hz); 119.55 (d, 7.7 Hz); 121.26 (d, 23.5 Hz); 155.67 (d, 234.6 Hz); 157.17; 170.00; 175.69.

The compound No. (91) can also be obtained, in a total yield of 82%, from amine No. (64) and 5-fluorosalicylic acid in accordance with Example B2.1(a).

(b) 20 mg (46%) of compound No. (92) are obtained from 30 mg (46 μmol) of compound No. (91) and 40 mg (64 μmol) of CMP-sia in accordance with Example B1.1(c) (in this case, the buffer solution contains 9% DMSO).

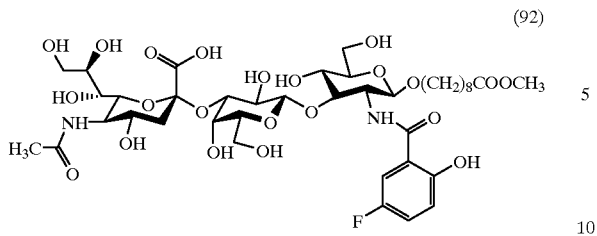

(92)

$^1$H-NMR (CD$_3$OD, 400.13 MHz) δ=0.90–1.21 (m, 8 H); 1.34–1.45 (m, 4 H); 1.62 (t, 11.6 Hz, 1 H); 1.92 (s, 3 H); 2.19 (t, 7.6 Hz, 2 H); 2.71 (dd, 11.6 Hz, 2.8 Hz, 1 H); 3.31 (m, 1 H); 3.37–3.71 (m, 17 H); 3.81–3.99 (m, 6 H); 4.40 (d, 8.6 Hz, 1 H); 4.58 (d, 8.6 Hz, 1 H); 6.83 (dd, 5.5 Hz, 10.3 Hz, 1 H); 7.08 (broad dt, 3.4 Hz, 8.1 Hz, 1 H); 7.48 (dd, 5.5 Hz, 10.3 Hz, 1 H). $^{13}$C-NMR (CD$_3$OD, 100.6 MHz) δ=22.44; 25.87; 26.99; 29.93; 30.14 (2×C); 30.42; 34.65; 41.63; 51.82; 53.74; 56.14; 62.39; 62.67; 63.99; 68.66; 69.29; 69.53; 70.60 (2×C); 70.77; 72.58; 74.72; 76.70; 77.33; 77.42; 81.87; 101.03; 102.54; 104.22; 114.53 (d, 24.5 Hz); 117.50; 119.78 (d, 7.6 Hz); 121.51 (d, 23.7 Hz); 156.49 (d, 235.8 Hz); 170.42; 174.96; 175.29; 175.93; remaining signals not resolved.

(c) 6 mg (100%) of compound No. (87) are obtained from 5 mg (5.3 μmol) of compound No. (92) and 6 mg (10 μmol) of GDP-fuc in accordance with Example B1.1(d).

$^1$H-NMR (CD$_3$OD, 400.13 MHz) δ=0.91–1.48 (m, 15 H); 1.60 (broad t, 11.0 Hz, 1 H); 1.92 (s, 3 H); 2.18 (t, 7.6 Hz, 2 H); 2.70 (dd, 11.6 Hz, 2.8 Hz, 1 H); 3.28 (m, 1 H); 3.34–3.92 (m, 25 H); 4.36 (broad t, 10.3 Hz, 1 H); 4.42 (d, 8.6 Hz, 1 H); 4.69 (m, 2 H); 5.01 (d, 4.9 Hz, 1 H); 6.88 (dd, 5.5 Hz, 10.3 Hz, 1 H); 7.07 (broad dt, 3.4 Hz, 8.1 Hz, 1 H); 7.45 (dd, 5.5 Hz, 10.3 Hz, 1 H). $^{13}$C-NMR (CD$_3$OD, 100.6 MHz) δ=16.70; 22.59; 26.00; 27.13; 30.08; 30.27; 30.29; 30.59; 34.78; 41.88; 51.96; 53.86; 58.34; 61.59; 63.08; 64.11; 67.80; 68.68; 69.49; 69.63; 70.12; 70.72; 71.10; 71.16; 72.62; 73.71; 74.07; 74.85; 76.42; 76.87; 77.32; 77.71; 99.50; 101.25; 102.29; 103.67; 115.05 (d, 24.5 Hz); 118.52 (d, 6.5 Hz); 120.07; 121.62 (d, 24.0 Hz); 155.99 (d, 233.9 Hz); 156.74; 170.14; 175.15; 175.38 (2×C).

Example B2.8

Preparation of Compound No. (93)

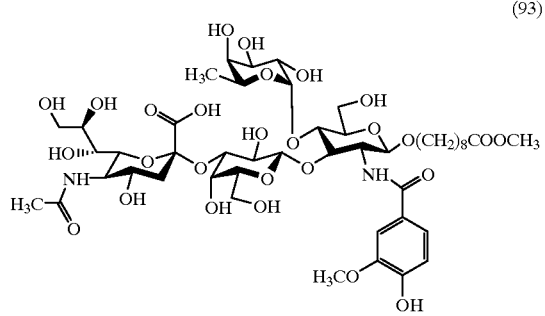

(93)

(a) 42 mg (28%) of amide No. (94) are obtained, in accordance with Example B2.7(a), from 44 mg (258 μmol) of vanillic acid (Fluka) and 100 mg (234 μmol) of compound No. (90) in the presence of 107 mg (282 μmol) of TBTU and 40 μl (282 μmol) of triethylamine in 2 ml of dry DMF.

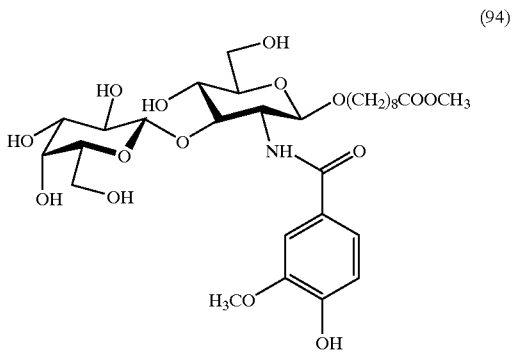

(94)

$^1$H-NMR (CD$_3$OD-CDCl$_3$, 400.13 MHz) δ=0.99–1.60 (m, 12 H); 2.20 (t, 7.5 Hz, 2 H); 3.33–3.92 (m, 19 H); 3.98 (broad t, 9.6 Hz, 1 H); 4.32 (d, 8.3 Hz, 1H); 4.66 (d, 8.2 Hz, 1 H); 6.81 (d, 8.3 Hz, 1 H); 7.36 (dd, 1.2 Hz, 7.2 Hz, 1H); 7.44 (d, 1.2 Hz, 1 H); $^{13}$C-NMR (CD$_3$OD-CDCl$_3$, 100.6 MHz) δ=25.65; 26.19; 29.52; 29.65 (2×C); 29.82; 35.38; 52.29; 56.56; 56.91; 61.21 (2×C); 69.67; 69.80; 71.09; 72.03; 72.13; 74.01; 74.27; 76.95; 83.35; 102.12; 104.73; 112.12; 115.70; 122.06; 126.71; 148.51; 150.81; 170.63; 176.30. Compound No. (94) can also be obtained, in a total yield of 27%, from vanillic acid and amine No. (64) in accordance with Example B2.1(a).

(b) 22 mg (70%) of compound No. (95) are obtained from 22 mg (34 μmol) of compound No. (94) and 58 mg (88 μmol) of CMP-sia in accordance with Example B1.1(c) (in this case, the buffer solution contains 6% DMSO).

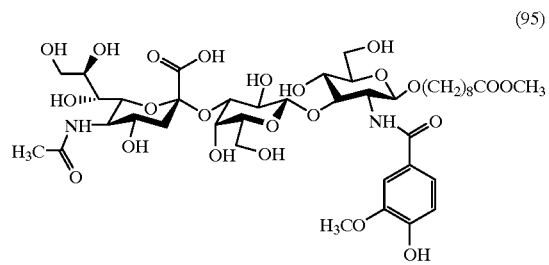

(95)

$^1$H-NMR (CD$_3$OD, 400.13 MHz) δ=0.93–1.29 (m, 8 H); 1.35–1.47 (m, 4 H); 1.65 (broad t, 11.6 Hz, 1 H); 1.95 (s, 3 H); 2.18 (t, 7.6 Hz, 2 H); 2.73 (dd, 11.6 Hz, 2.8 Hz, 1 H); 3.32 (m, 1 H); 3.37–3.71 (m, 18 H); 3.80–3.98 (m, 9 H); 4.37 (d, 8.6 Hz, 1 H); 4.60 (d, 8.6 Hz, 1 H); 6.81 (dd, 5.5 Hz, 10.3 Hz, 1 H); 7.33 (broad dt, 3.4 Hz, 8.1 Hz, 1 H); 7.41 (dd, 5.5 Hz, 10.3 Hz, 1 H). $^{13}$C-NMR (CD$_3$OD, 100.6 MHz) δ=21.33; 24.67; 25.85; 28.77; 29.03 (2×C); 29.33; 33.46; 40.43; 50.66; 52.59; 55.32 (2×C); 61.38; 61.51; 62.74; 67.60; 68.1 1; 68.32; 69.45; 69.54 (2×C); 71.45; 73.55; 75.58; 76.02; 76.22; 82.03; 99.91; 101.51; 102.98; 110.94; 114.62; 120.99; 125.90; 147.44; 149.96; 169.31; 173.79; 174.13; 174.80.

(c) 9 mg (67%) of compound No. (93) are obtained from 12 mg (13 μmol) of compound No. (95) and 12 mg (19 μmol) of GDP-fuc in accordance with Example B1.1(d).

$^1$H-NMR (CD$_3$OD, 400.13 MHz) δ=0.88–1.17 (m, 11 H); 1.29–1.40 (m, 4 H); 1.61 (broad t, 11.0 Hz, 1 H); 1.91 (s, 3 H); 2.13 (t, 7.6 Hz, 2 H); 2.68 (dd, 11.6 Hz, 2.8 Hz, 1 H); 3.31–3.87 (m, 28 H); 4.30 (broad t, 8.5 Hz, 1 H); 4.42 (d, 8.6 Hz, 1 H); 4.66 (d, 8.6 Hz, 1 H); 4.96 (d, 4.3 Hz, 1 H); 6.81 (d, 8.3 Hz, 1 H); 7.29 (dd, 2.1 Hz, 8.3 Hz, 1 H); 7.35 (d, 2.1

Hz, 1 H); $^{13}$C-NMR (CD$_3$OD, 100.6 MHz) δ=16.39; 22.39; 25.62; 26.80; 29.70; 29.93; 29.97; 30.27; 34.47; 41.42; 51.83; 53.47; 56.36; 58.34; 61.23; 62.80; 63.59; 67.56; 68.28; 69.26; 69.67; 70.54; 70.76 (2×C); 72.41; 73.32; 73.82; 74.45; 76.03; 76.66; 76.93; 77.17; 99.18; 101.97; 103.46; 111.90; 115.83; 121.93; 126.79; 148.52; 150.89; 176.19; remaining signals not resolved.

Example B2.9

Preparation of Compound No. (96)

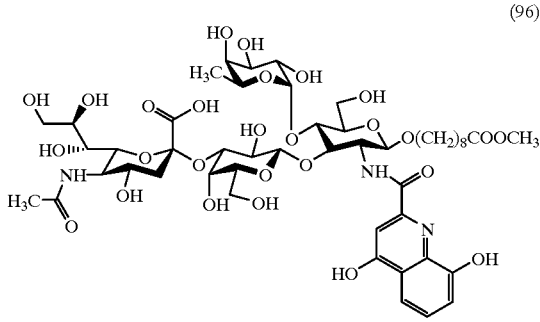

(96)

(a) 85 mg (52%) of amide No. (97) are obtained, in accordance with Example B2.7(a), from 53 mg (258 μmol) of xanthurenic acid (Fluka) and 120 mg (234 μmol) of amine No. (90) in the presence of 107 mg (282 μmol) of HBTU and 40 μl (282 μmol) of triethylamine in 2 ml of DMF.

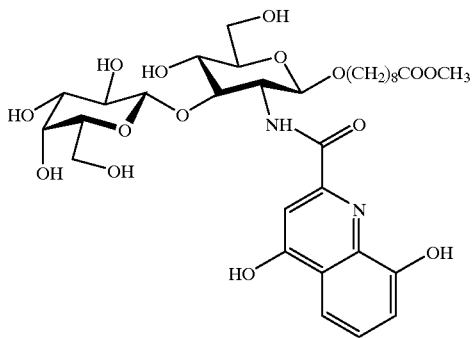

(97)

$^1$H-NMR (CD$_3$OD, 400.13 MHz) δ=0.61–1.40 (m, 12 H); 1.94 (t, 7.6 Hz, 2 H); 3.23–4.03 (m, 17 H); 4.28 (d, 7.6 Hz, 1 H); 4.58 (d, 8.6 Hz, 1 H); 7.02 (d, 8.4 Hz, 1 H); 7.21 (m, 2 H); 7.56 (broad d, 8.4 Hz, 1 H). $^{13}$C-NMR (CD$_3$OD, 100.6 MHz) δ=25.80; 27.21; 29.97; 30.29; 30.36; 30.54; 34.65; 51.90; 57.89; 62.44; 62.67; 70.15; 70.62; 70.82; 72.27; 74.40; 76.99; 77.82; 84.26; 102.44; 105.29; 114.75; 118.66; 126.92; 175.94; remaining not resolved.

(b) 27 mg (94%) of compound No. (98) are obtained from 20 mg (29 μmol) of compound No. (97) and 27 mg (41 μmol) of CMP-sia in accordance with Example B1.1(c).

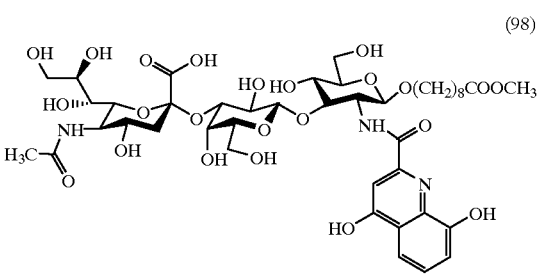

(98)

$^1$H-NMR (CD$_3$OD, 400.13 MHz) δ=0.61–1.40 (m, 12 H); 1.56 (broad t, 11.0 Hz, 1 H); 1.89 (s, 3 H); 1.96 (t, 7.5 Hz, 2 H); 2.67 (dd, 11.6 Hz, 2.8 Hz, 1 H); 3.23–4.03 (m, 24 H); 4.38 (d, 8.6 Hz, 1 H); 4.52 (d, 8.6 Hz, 1 H); 7.03 (broad d, 8.4 Hz, 1 H); 7.21 (broad m, 2 H); 7.59 (broad d, 8.4 Hz, 1 H). $^{13}$C-NMR (CD$_3$OD, 100.6 MHz) δ=22.65; 25.82; 27.22; 30.00; 30.10; 30.35; 30.56; 34.69; 41.69; 51.91; 53.89; 56.45; 62.63; 62.73; 63.93; 68.77; 69.34; 69.69; 70.82 (2×C); 72.79; 74.77; 76.83; 77.37; 77.58 (2×C); 83.88; 101.16; 102.67; 104.49; 115.02; 127.00; 173.14; 173.67; 174.47; 177.22; remaining signals not resolved.

(c) 20 mg (76%) of compound No. (96) are obtained from 23 mg (23 μmol) of compound No. (98) and 22 mg (34 μmol) of GDP-fuc in accordance with Example B1.1(d).

$^1$H-NMR (CD$_3$OD, 400.13 MHz) δ=0.61–1.41 (m, 15 H); 1.61 (broad t, 11.0 Hz, 1 H); 1.90 (s, 3 H); 1.99 (t, 7.5 Hz, 2 H); 2.67 (dd, 11.6 Hz, 2.8 Hz, 1 H); 3.24–3.94 (m, 25 H); 4.09 (broad m 1 H); 4.28 (broad t 8.5 Hz, 1 H); 4.49 (d, 8.6 Hz, 1 H); 4.60 (broad d, 8.6 Hz, 1 H); 5.02 (d, 4.3 Hz, 1 H); 7.02 (broad d, 8.4 Hz, 1 H); 7.15 (broad s, 1 H); 7.22 (t, 8.4 Hz, 1 H); 7.61 (broad d, 8.4 Hz, 1 H). $^{13}$C-NMR (CD$_3$OD, 100.6 MHz) δ=16.71; 22.64; 25.81; 27.24; 30.00; 30.31 (2×C); 30.58; 34.71; 41.70; 51.91; 53.82; 58.14; 61.50; 63.15; 63.86; 67.85; 68.60; 69.48; 69.64; 70.03; 70.84; 70.98; 71.14 (2×C); 72.75; 73.69; 73.98; 74.74; 76.40; 77.39; 77.49; 99.59; 101.23; 102.69; 103.64; 114.84; 127.03; 175.32; remaining signals not resolved.

C. Ligand Binding Assay for Determination of IC$_{50}$ Values-Conserved Use of Positive Controls E-selectin/human IgG chimera [cloned and expressed according to Kolbinger, F., Patton, J. T., Geisenhoff, G., Aenis, A., Li, X., Katopodis, A., Biochemistry 35:6385–6392 (1996)] are incubated in Falcon probind™ microtiter plate (Plate 1) at a concentration of 200 ng/well in 0.01 M Tris, 0.15 M NaCl, 1 mM CaCl$_2$, pH 7.4 (Tris-Ca$^{++}$ buffer). Thus the plating solution is dispensed as 100 μl/well of 2 μg/ml E-chimera. Row 12 is left blank with only buffer. Plate 1 is incubated covered at 37° C. for 2 hours. After incubation 100 μl/well of 2% BSA in Tris Ca$^{++}$ buffer is added and incubated at RT for 1 hour. During incubation the compounds (2× serial dilution) are titrated in 1% BSA in Tris-Ca$^{++}$ using U-shaped low bind microtiter plates (Plate 2). The rows are serially diluted up to row 9. Rows 10, 11, and 12 are just buffer. Final volume is 60 μl/well and the first well contains 10 mM of compound with the exception of the positive controls, A (SLe$^x$-Lemieux) and B are used as positive controls for each plate and the first well contains 5 mM of these compounds. PolySLe$^a$SA-HRP conjugate is prepared in advance by incubating Sialyl Le$^a$-PAA-biotin (cat #01-044, GlycoTech Corp., Rockville, Md.) with Streptavidin-HRP in a molar ratio of 1:2. 60 μl/well of 1 ng/μl of polySL$^a$SA-HRP conjugate in 1% BSA in Tris-Ca$^{++}$ are added to all wells except row 11 in Plate 2. Plate 1 is washed four times with Tris-Ca$^{++}$ in the automatic plate washer. 100 µl/well are transferred from Plate 2 to Plate 1 starting from lowest concentration of compound. Plate 2 is discarded. The plate is incubated while rocking at RT for 2 hours. The plate is washed 4 times with Tris-Ca$^{++}$ using automatic plate washer. 100 µl/well of Substrate [Mix 3,3', 5,5'-tetramethylbenzidine reagent and $H_2O_2$, at 1:1 ratio] are added with an 8 channel pipettor from right to left. The plate is incubated at RT for 2 minutes. The reaction is stopped by adding 100 µl/well of 1 M $H_3PO_4$ using the 8 channel pipettor from right to left. Absorbance of light at 450 nm is measured in a microtiter plate reader.

Control compound A:

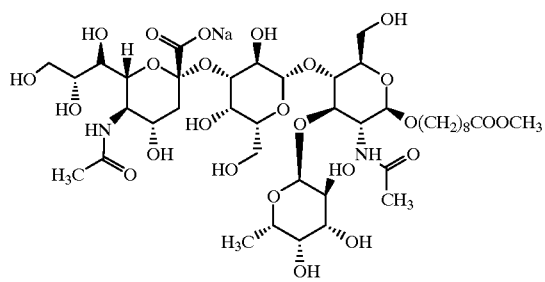

Control compound B:

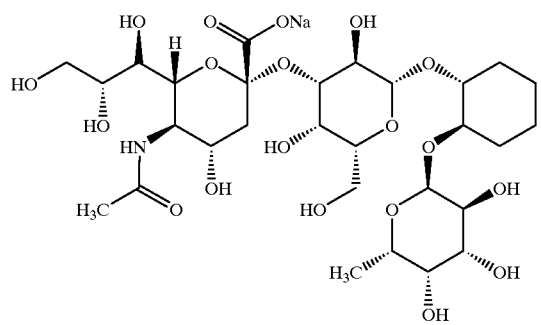

$IC_{50}$ is calculated by determining the concentration of compound required to inhibit maximal binding of the poly-SialylLe$^a$HRP conjugate to immobilized E-selectin/human IgG chimera by 50%. The relative $IC_{50}$ is calculated by determining the ratio of the $IC_{50}$ of an internal control compound to the $IC_{50}$ of the test compound.

In the following table $RIC_{50}$ means $$\frac{IC_{50} \text{ (Test compound)}}{IC_{50} \text{ (Control compound A)}}$$

TABLE 1

| Compound No. | RIC$_{50}$ |
| --- | --- |
| (1) | 0.025 |
| (6) | 0.090 |
| (10) | 0.040 |
| (14) | 0.090 |
| (18) | 0.072 |
| (22) | 0.099 |
| (26) | 0.098 |
| (30) | 0.029 |
| (36) | 0.039 |
| (40) | 0.779 |

TABLE 1-continued

| Compound No. | RIC$_{50}$ |
| --- | --- |
| (44) | 0.693 |
| (48) | 0.173 |
| (49) | 1.472 |
| (53) | 0.013 |
| (56) | 0.075 |
| (65) | 3.834 |
| (68) | 2.836 |
| (74) | 0.979 |
| (77) | 5.256 |
| (83) | 0.032 |

What is claimed is:
1. A compound of the formula I or II

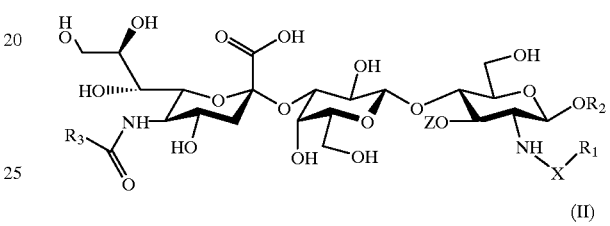

(I)

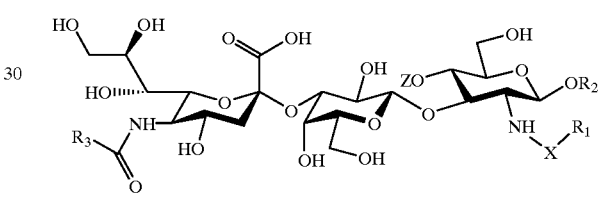

(II)

in which
Z is an α-bonded L-fucose of the formula III

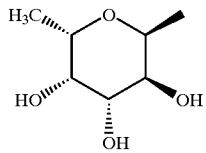

(III)

$R_1$ is a monocyclic or bicyclic $C_6$–$C_{10}$aryl or $C_2$–$C_9$heteroaryl which is substituted by at least one OH and can be substituted, once or more than once, by a substituent selected from the group comprising halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide;

$R_2$ is $C_1$–$C_{18}$alkyl, monosubstituted or polysubstituted $C_1$–$C_{18}$alkyl, $C_3$–$C_8$cycloalkyl or monosubstituted or polysubstituted $C_3$–$C_8$cycloalkyl, where one or more $CH_2$ groups in the alkyl and in the cycloalkyl can be replaced, independently of each other, by oxygen, sulfur or an imino group and the substituents are selected from the group comprising OH, SH, $NH_2$, carboxamide and C(O)OR, in which R is H or $C_1$–$C_{18}$alkyl;

$R_3$ is a methyl group or hydroxymethyl group; and

X is —C(O)—, —C(S)—, —S(O)$_2$—, —C(O)Y— or —C(S)Y—, where Y is NH, O, S, S-$C_1$–$C_6$alkylene, NH-$C_1$–$C_6$alkylene or O-$C_1$–$C_6$alkylene.

2. A compound according to claim 1, wherein $R_1$ is (a) a monohydroxylated, dihydroxylated or trihydroxylated phenyl; (b) a monohydroxylated, dihydroxylated or trihydroxylated monocyclic heteroaryl, in which one or more CH units are replaced, independently of each other, by one or more nitrogen atoms, or (c) a hydroxylated heteroaryl consisting of two six-membered rings in which one or more CH units is/are replaced, independently of each other, by one or more nitrogen atoms.

3. A compound according to claim 1, wherein $R_1$ is a monocyclic aryl or heteroaryl which is substituted by at least one OH and can be substituted, once or more than once, by a substituent selected from the group comprising halogen, trifluoromethyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide.

4. A compound according to claim 1, wherein $R_1$ is a monocyclic or bicyclic $C_6$–$C_{10}$aryl or $C_2$–$C_9$heteroaryl which is substituted, once or twice, by a hydroxyl group and can be substituted, once or more than once, by a substituent selected from the group comprising $C_1$–$C_{18}$alkyl, $C_1$–$C_{18}$alkoxy, halogen, nitro and amino.

5. A compound according to claim 4, wherein the $C_2$–$C_9$heteroaryl is $C_2$–$C_9$-N heteroaryl.

6. A compound according to claim 4, wherein $R_1$ is phenyl, pyrimidinyl, pyridinyl, quinolinyl or pteridinyl which is substituted, once or twice, by a hydroxyl group and can be substituted, once or more than once, by a substituent selected from the group comprising $C_1$–$C_{18}$alkyl, $C_1$–$C_{18}$alkoxy, halogen, nitro and amino.

7. A compound according to claim 6, wherein $R_1$ is phenyl which is substituted, once or twice, by a hydroxyl group and can be substituted, once or twice, by a substituent selected from the group comprising $C_1$–$C_{18}$alkyl, $C_1$–$C_{18}$alkoxy, halogen, nitro and amino; pyrimidinyl which is substituted twice by a hydroxyl group; quinolinyl which is substituted by one or two hydroxyl group(s), pyridinyl which is substituted once by a hydroxyl group; or pteridinyl which is substituted once by a hydroxyl group and can be substituted by an amino group.

8. A compound according to claim 1, wherein $R_1$ is 2-hydroxyphenyl; 2,4-dihydroxyphenyl; 3,4-dihydroxyphenyl; 3,5-dihydroxyphenyl; 4-hydroxy-3-methoxyphenyl; 4-hydroxy-3,5-di-methoxyphenyl; 3-fluoro-6-hydroxyphenyl; 2-hydroxy-5-methylphenyl; 3-hydroxy-4-nitrophenyl; 3-hydroxy-4-aminophenyl; 3,5-dihydroxypyrimidinyl; 3-(6-hydroxy)pyridinyl; 2-(8-hydroxy)quinolinyl; 6-(2-amino-8-hydroxy)pteridinyl; or 2-(4,8-dihydroxy)quinolinyl.

9. A compound according to claim 8, wherein $R_1$ is 2,4-dihydroxyphenyl; 3,4-dihydroxyphenyl; 3,5-dihydroxyphenyl; 3-fluoro-6-hydroxyphenyl; 3,5-dihydroxypyrimidinyl; 2-(8-hydroxy)quinolinyl, 2-(4,8-dihydroxy)quinolinyl or 6-(2-amino-8-hydroxy)pteridinyl.

10. A compound according to claim 9, wherein $R_1$ is 2,4-dihydroxyphenyl; 3,5-dihydroxypyrimidinyl; 2-(8-hydroxy)quinolinyl or 2-(4,8-dihydroxy)quinolinyl.

11. A compound according to claim 1, wherein $R_2$ is $C_1$–$C_{18}$alkyl, monosubstituted or polysubstituted $C_1$–$C_{18}$alkyl, $C_3$–$C_8$cycloalkyl or monosubstituted or polysubstituted $C_3$–$C_8$cycloalkyl, where the substituents are selected from the group comprising OH, SH, $NH_2$, carboxamide and C(O)OR, in which R is H or $C_1$–$C_{18}$alkyl.

12. A compound according to claim 11, wherein $R_2$ is $C_1$–$C_{18}$alkyl or $C_1$–$C_{18}$alkyl which is substituted, once or more than once, independently of each other, by OH, SH, $NH_2$, carboxamide or C(O)O$C_1$–$C_6$alkyl.

13. A compound according to claim 12, wherein $R_2$ is $C_1$–$C_{18}$alkyl which is unsubstituted or substituted by C(O)OCH$_3$.

14. A compound according to claim 13, wherein $R_2$ is —(CH$_2$)$_8$COOCH$_3$.

15. A compound according to claim 1, wherein $R_3$ is methyl.

16. A compound according to claim 1, wherein X is —C(O)—, —C(S)—, —C(O)Y— or —C(S)Y—, where Y is NH, O, NH-$C_1$–$C_6$alkylene or O-$C_1$–$C_6$alkylene.

17. A compound according to claim 16, wherein X is —C(O)—, —C(S)—, —C(O)Y— or —C(S)Y—, where Y is NH— or O—$C_1$–$C_6$alkylene.

18. A compound according to claim 17, wherein X is —C(O)— or —C(O)Y—, where Y is O—$C_1$–$C_6$alkylene.

19. A compound according to claim 18, wherein X is —C(O)— or —C(O)Y—, where Y is O—CH$_2$—.

20. A compound according to claim 1, wherein $R_1$ is a monocyclic aryl or heteroaryl which is substituted by at least one OH and can be substituted, once or more than once, by a substituent selected from the group comprising halogen, trifluoromethyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide; $R_2$ is $C_1$–$C_{18}$alkyl, monosubstituted or polysubstituted $C_1$–$C_{18}$alkyl, $C_3$–$C_8$cycloalkyl or monosubstituted or polysubstituted $C_3$–$C_8$cycloalkyl, where the substituents are selected from the group comprising OH, SH, $NH_2$, carboxamide and C(O)OR, in which R is H or $C_1$–$C_{18}$alkyl; $R_3$ is methyl; and X is —C(O)—, —C(S)—, —S(O)$_2$—, —C(O)Y— or —C(S)Y—, with Y being NH or O—CH$_2$—.

21. A compound according to claim 20, wherein $R_1$ is a monocyclic aryl or heteroaryl which is substituted by at least one OH; $R_2$ is $C_1$–$C_{18}$alkyl or $C_1$–$C_{18}$alkyl which is substituted, once or more than once, independently of each other, by OH, SH, $NH_2$, carboxamide or C(O)OR, in which R is H or $C_1$–$C_{18}$alkyl; $R_3$ is methyl; and X is —C(O)— or —C(O)Y—, with Y being O—CH$_2$—.

22. A compound according to claim 21, wherein $R_1$ is phenyl or pyrimidyl which is substituted once or twice by OH and $R_2$ is $C_1$–$C_{18}$alkyl or $C_1$–$C_{18}$alkyl which is substituted once by C(O)OR.

23. A compound according to claim 22, wherein $R_1$ is phenyl which is substituted once or twice by OH or pyrimidyl which is substituted twice by OH and $R_2$ is —(CH$_2$)$_8$COOCH$_3$ or —(CH$_2$)$_8$COOH.

24. A compound according to claim 1, wherein $R_1$ is a monocyclic or bicyclic $C_6$–$C_{10}$aryl or $C_2$–$C_9$heteroaryl which is substituted, once or twice, by a hydroxyl group and can be substituted, once or more than once, by a substituent selected from the group comprising $C_1$–$C_{18}$alkyl, $C_1$–$C_{18}$alkoxy, halogen, nitro and amino; $R_2$ is $C_1$–$C_{18}$alkyl, monosubstituted or polysubstituted $C_1$–$C_{18}$alkyl, $C_3$–$C_8$cycloalkyl or monosubstituted or polysubstituted $C_3$–$C_8$cycloalkyl, where the substituents are selected from the group comprising OH, SH, $NH_2$, carboxamide and C(O)OR, in which R is H or $C_1$–$C_{18}$alkyl; $R_3$ is methyl and X is —C(O)—, —C(S)—, —C(O)Y— or —C(S)Y—, with Y being NH, O, NH-$C_1$–$C_6$alkylene or O—$C_1$–$C_6$alkylene.

25. A compound according to claim 24, wherein $R_1$ is phenyl, pyrimidinyl, pyridinyl, quinolinyl or pteridinyl which is substituted, once or twice, by a hydroxyl group and can be substituted, once or more than once, by a substituent selected from the group comprising $C_1$–$C_{18}$alkyl, $C_1$–$C_{18}$alkoxy, halogen, nitro and amino; $R_2$ is $C_1$–$C_{18}$alkyl or $C_1$–$C_{18}$alkyl which is substituted, once or more than once, independently of each other, by OH, SH, $NH_2$, carboxamide or $C(O)OC_1-C_6$alkyl; $R_3$ is methyl and X is —C(O)—, —C(S)—, —C(O)Y— or —C(S)Y—, with Y being NH— or O—$C_1-C_6$alkylene.

26. A compound according to claim 25, wherein $R_1$ is phenyl which is substituted, once or twice, by a hydroxyl group and can be substituted, once or twice, by a substituent selected from the group comprising $C_1-C_{18}$alkyl, $C_1-C_{18}$alkoxy, halogen, nitro and amino; pyrimidinyl which is substituted twice by a hydroxyl group; quinolinyl which is substituted by one or two hydroxyl group(s), pyridinyl which is substituted once by a hydroxyl group; or pteridinyl which is substituted once by a hydroxyl group and can be substituted by an amino group; $R_2$ is $C_1-C_{18}$alkyl which is unsubstituted or is substituted by C(O) $OCH_3$; $R_3$ is methyl and X is —C(O)— or —C(O)Y—, where Y is O—$C_1-C_6$alkylene.

27. A compound according to claim 26, wherein $R_1$ is 2-hydroxyphenyl; 2,4-dihydroxyphenyl; 3,4-dihydroxyphenyl; 3,5-dihydroxyphenyl; 4-hydroxy-3-methoxyphenyl; 4-hydroxy-3,5-dimethoxyphenyl; 3-fluoro-6-hydroxyphenyl; 2-hydroxy-5-methylphenyl; 3-hydroxy-4-nitrophenyl; 3-hydroxy4-aminophenyl; 3,5-dihydroxypyrimidinyl; 3-(6-hydroxy)pyridinyl; 2-(8-hydroxy)quinolinyl; 6-(2-amino-8-hydroxy)pteridinyl; or 2-(4,8-dihydroxy)quinolinyl; $R_2$ is —$(CH_2)_8COOCH_3$; $R_3$ is methyl and X is —C(O)— or —C(O)Y—, where Y is O—$CH_2$—.

28. A compound according to claim 27, wherein $R_1$ is 2,4-dihydroxyphenyl; 3,4-dihydroxyphenyl; 3,5-dihydroxyphenyl; 3-fluoro-6hydroxyphenyl; 3,5-dihydroxypyrimidinyl; 2-(8-hydroxy)quinolinyl, 2-(4,8-dihydroxy)quinolinyl or 6-(2-amino-8-hydroxy)pteridinyl.

29. A compound according to claim 28, wherein $R_1$ is 2,4-dihydroxyphenyl; 3,5-dihydroxypyrimidinyl, 2-(8-hydroxy)quinolinyl or 2-(4,8-dihydroxy)quinolinyl.

30. A compound according to claim 1, wherein, in formula I,
(a) $R_2$ is —$(CH_2)_8COOCH_3$, $R_3$ is methyl, X is —C(O)— and $R_1$ is 3,5-dihydroxypyrimidinyl; 2-hydroxyphenyl; 3,4-dihydroxyphenyl; 3,5-dihydroxyphenyl; 4-hydroxy-3-methoxyphenyl; 4-hydroxy-3,5-dimethoxyphenyl; 2,4-dihydroxyphenyl; 3-fluoro-6-hydroxyphenyl; 2-hydroxy-5-methylphenyl; 3-hydroxy-4-nitrophenyl; 3-hydroxy-4-aminophenyl; 3-(6-hydroxy)pyridinyl; 2-(8-hydroxy)quinolinyl; 6-(2-amino-8-hydroxy)pteridinyl; or 2-(4,8-dihydroxy)quinolinyl; or
(b) $R_2$ is —$(CH_2)_8COOCH_3$, $R_3$ is methyl and X is —C(O)Y—, in which Y is O—$CH_2$—, and $R_1$ is 3,5-dihydroxyphenyl.

31. A compound according to claim 1, wherein, in formula II,
(a) $R_2$ is —$(CH_2)_8COOCH_3$, $R_3$ is methyl, X is —C(O)— and $R_1$ is 3,5-dihydroxyphenyl; 4-hydroxy-3,5-dimethoxyphenyl; 3,4-dihydroxyphenyl; 3,5-dihydroxypyrimidinyl; 2-(8-hydroxy)quinolinyl; 3-fluoro-6-hydroxyphenyl; 4-hydroxy-3-methoxyphenyl or 2-(4,8-dihydroxy)quinolinyl; or
(b) $R_2$ is —$(CH_2)_8COOCH_3$, $R_3$ is methyl and X is —C(O)Y—, in which Y is O—$CH_2$—, and $R_1$ is 3,5-dihydroxyphenyl.

32. A process for preparing compounds of formula I

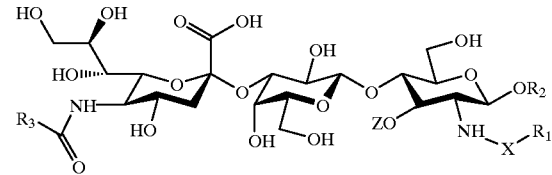

(I)

wherein (a) a compound of the formula V $$R_7—X'—R_1 \quad (V),$$

in which (a') $R_7$ is halogen, X' is —C(O)—, —C(S)—, —$S(O)_2$—, —C(O)Y— or —C(S)Y—, where Y is NH, O, S, S-$C_1-C_6$alkylene, NH-$C_1-C_6$alkylene or O-$C_1-C_6$alkylene; and $R_1$ is a monocyclic or bicyclic $C_6-C_{10}$aryl or $C_2-C_9$heteroaryl which is substituted by at least one OH and can be substituted, once or more than once, by a substituent selected from the group comprising halogen, halo-$C_1-C_{18}$alkyl, nitro, $C_1-C_{18}$alkyl, $C_1-C_{18}$alkoxy, amino, mono-$C_1-C_{18}$alkylamino, di-$C_1-C_{18}$alkylamino, benzylamino, sulfhydryl, thio-$C_1-C_{18}$alkyl and $C_1-C_{18}$alkylcarboxamide; or (a") $R_7$ is C(O) or C(S), X' is —N= and $R_1$ is as defined above, or (a''') $R_7$ is OH, X' has the abovementioned meanings of X and $R_1$ is as already defined above, is reacted, directly after the in-situ activation, with a compound of the formula IV

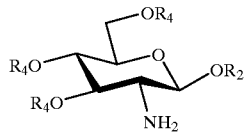

(IV)

in which $R_2$ is $C_1-C_{18}$alkyl, monosubstituted or polysubstituted $C_1-C_{18}$alkyl, $C_3-C_8$cycloalkyl or monosubstituted or polysubstituted $C_3-C_8$cycloalkyl, with it being possible for one or more $CH_2$ groups, in the alkyl or in the cycloalkyl, to be replaced, independently of each other, by oxygen, sulfur or an imino group and with the substituents being selected from the group comprising OH, SH, $NH_2$, carboxamide and C(O)OR, in which R is H or $C_1-C_{18}$alkyl; and the individual $R_4$s are, independently of each other, hydrogen or a protecting group, with the elimination of any protecting groups which are present, to form a compound of the formula VI

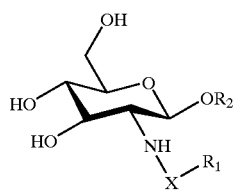

(VI)

in which $R_2$, $R_1$ and X are as previously defined;

(b) the compound of the formula VI is reacted with uridine diphosphate galactose in the presence of β(1→4)galactosyl transferase, and then with cytidine monophosphate sialic acid in the presence of sialyl transferase, to form a compound of the formula VII

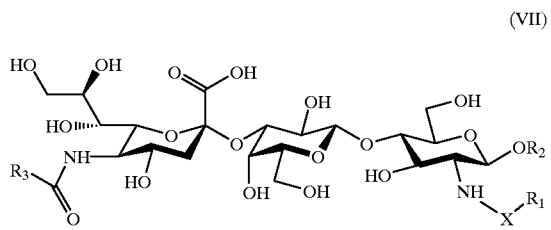

(VII)

in which $R_1$, $R_2$, $R_3$ and X are as previously defined, and (c) the resulting product is reacted with guanosine diphosphate fucose in the presence of fucosyl transferase to form a compound of the formula I.

33. A process for preparing compounds of formula I

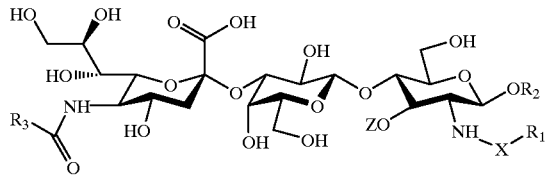

(I)

wherein (a) a compound of the formula VI according to claim 32 is reacted with uridine diphosphate galactose in the presence of β(1→4)galactosyl transferase and then with cytidine monophosphate sialic acid in the presence of sialyl transferase, to form a compound of the formula VII according to claim 32, and (b) the resulting product is reacted with guanosine diphosphate fucose in the presence of fucosyl transferase to form a compound of the formula I.

34. A process for preparing compounds of the formula II

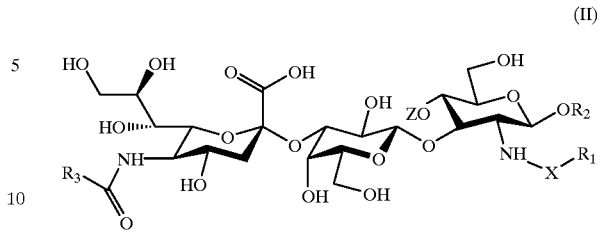

(II)

wherein (a) a compound of the formula VI according to claim 32 is reacted with uridine diphosphate galactose in the presence of β(1→3)galactosyl transferase and then with cytidine monophosphate sialic acid in the presence of sialyl transferase, to form a compound of the formula VIII

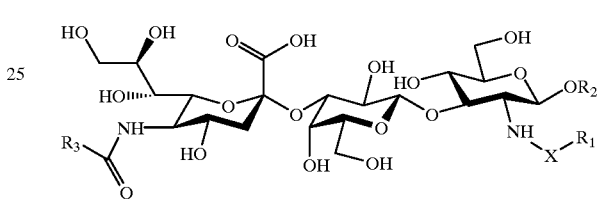

(VIII)

in which $R_1$, $R_2$, $R_3$ and X have the meanings according to claim 32, and (b) the resulting product is reacted with guanosine diphosphate fucose in the presence of fucosyl transferase to form a compound of the formula II.

35. A process for preparing compounds of the formula II

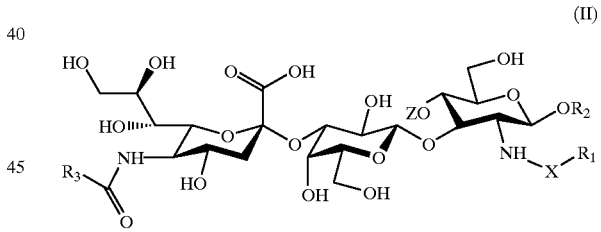

(II)

wherein (a) a compound of the formula V according to claim 32 is reacted, directly after the in-situ activation, with a compound of formula IX

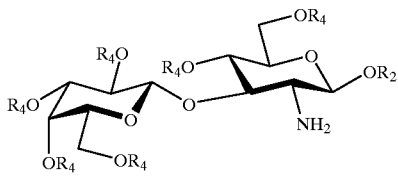

(IX)

in which $R_2$ and the individual $R_4$s have the meanings according to claim 32, with the elimination of any protecting groups which are present, to form a compound of the formula X

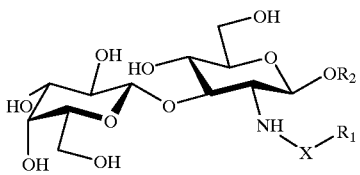

in which $R_2$, $R_1$ and X have the meanings according to claim 32;

(b) the compound of the formula X is reacted with cytidine monophosphate sialic acid in the presence of sialyl transferase to form a compound of the formula VIII

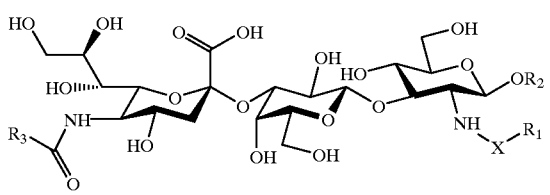

in which $R_1$, $R_2$, $R_3$ and X are as previously defined, and (c) the resulting product is reacted with guanosine diphosphate fucose in the presence of fucosyl transferase to form a compound of the formula II.

36. A process for preparing compounds of the formula II

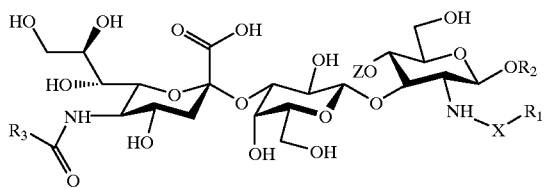

wherein (a) a compound of the formula X according to claim 32 is reacted with cytidine mono-phosphate sialic acid in the presence of sialyl transferase to form a compound of the formula VIII according to claim 32, and (b) the resulting product is reacted with guanosine diphosphate fucose in the presence of fucosyl transferase to form a compound of the formula II.

37. A process according to any one of claims 32 to 36, wherein the enzymic reactions are carried out in the presence of from 0.1 U to 5 U of the enzyme concerned.

38. A process according to any one of claims 32 to 36, wherein the glycosyl donor is employed in excess.

39. A process according to claim 38, wherein from 1.2 to 2 equivalents of uridine diphosphate galactose, from 1.2 to 2.3 equivalents of cytidine monophosphate sialic acid or from 1.2 to 2.5 equivalents of guanosine diphosphate fucose are employed.

40. A process according to any one of claims 32 to 34, wherein the enzymic transfer of galactose and sialic acid is effected either in one single step or in two consecutive steps.

41. A process according to any one of claims 32 to 36, wherein the enzymic syntheses are carried out in the presence of buffers in the pH and temperature ranges which are optional in each case.

42. A process according to claim 41, wherein the buffers are sodium cacodylate tris(hydroxymethyl)aminomethane or 4-(2-hydroxyethyl)piperazine-1-ethanesulfonic acid.

43. A process according to claim 41, wherein the enzymic syntheses are carried out in the range from pH 6 to pH 8 and in the range from 25° C. to 37° C.

44. A process according to any one of claims 32 to 36, wherein the enzymic syntheses are carried out in the presence of salts and of auxiliary enzymes.

45. A process according to claim 44, wherein the enzymic syntheses are carried out in the presence of from 5 to 40 mM manganese II chloride and from 16 to 50 U of calf intestinal alkaline phosphatase.

46. A pharmaceutical composition comprising an anti-adhesion effective amount of a compound of claim 1, and a pharmaceutical excipient, optionally together with other active compounds or auxiliary substances.

* * * * *

UNITED STATES PATENT AND TRADEMARK OFFICE
CERTIFICATE OF CORRECTION

PATENT NO. : 6,187,754 B1
DATED : February 13, 2001
INVENTOR(S) : Reinhold Oehrlein It is certified that error appears in the above-identified patent and that said Letters Patent is hereby corrected as shown below:

Column 69,
Line 25, "3-hydroxy4-aminophenyl;" should read -- 3-hydroxy-4-aminophenyl; --.

Column 74,
Line 33, "from 25° C. to" should read -- from 25°C to --.

Signed and Sealed this

Fourteenth Day of August, 2001

*Attest:*

Nicholas P. Godici

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,187,754 B1
DATED : February 13, 2001
INVENTOR(S) : Reinhold Oehrlein It is certified that error appears in the above-identified patent and that said Letters Patent is hereby corrected as shown below:

Title page, Item [54] and Column 1, line 2,
Title, "EPITODE" should read as -- EPITOPE --

Signed and Sealed this

Thirtieth Day of November, 2004

JON W. DUDAS
*Director of the United States Patent and Trademark Office*